United States Patent [19]

Tanida et al.

[11] Patent Number: 5,478,808

[45] Date of Patent: Dec. 26, 1995

[54] 2-AMINO-6,7-DIHYDROXY-4-THIAHEPTANOIC ACID DERIVATIVES, PRODUCTION AND USE THEREOF

[75] Inventors: Seiichi Tanida, Kyoto; Tsuneaki Hida, Hyogo; Mitsuhiro Wakimasu, Ibaraki; Setsuo Harada, Hyogo; Koichi Yukishige, Osaka, all of Japan

[73] Assignee: Takeda Chemical Industries, Ltd., Osaka, Japan

[21] Appl. No.: 174,374

[22] Filed: Dec. 28, 1993

[30] Foreign Application Priority Data

| Dec. 28, 1992 | [JP] | Japan | 4-349062 |
| Mar. 16, 1993 | [JP] | Japan | 5-056185 |
| Jul. 22, 1993 | [JP] | Japan | 5-181735 |

[51] Int. Cl.$^6$ .......... A61K 38/00; C07K 5/00; C07K 7/00; C07K 17/00

[52] U.S. Cl. .......... 514/15; 514/16; 514/17; 514/18; 514/19; 530/328; 530/329; 530/330; 530/331; 562/426; 562/556

[58] Field of Search .......... 562/426, 556; 514/15–19; 530/328–331

[56] References Cited

U.S. PATENT DOCUMENTS 4,666,886  5/1987  Baschang et al. .......... 514/17

FOREIGN PATENT DOCUMENTS

| 014815 | 9/1980 | European Pat. Off. |
| 0000330 | 8/1981 | European Pat. Off. |
| 0210412 | 2/1987 | European Pat. Off. |
| 0548024 | 6/1993 | European Pat. Off. |
| 4-46194 | 2/1992 | Japan |
| 4-99796 | 3/1992 | Japan |

OTHER PUBLICATIONS

Metzger et al., Int. J. Peptide Protein Res., "Synthesis of N$_\alpha$-Fmoc protected derivatives of S-(2, 3-dihydroxyproply)-cysteine and their application in peptide synthesis", vol. 38, No. 6, pp. 545–554 (1991).

Chem. Pharm. Bull., "Synthesis of Optically Active Lipopeptide Analogs from the Outer Membrane of *Escherichia Coli*" Kurimura et al., 39 (10), pp. 2590–2596 (1991).

Chem. Pharm. Bull., "Synthesis and Mitogenic Activity of Chiral Lipopeptide WS 1279 and Its Derivatives" Kurimura et al., 41 (11), pp. 1965–1970 (1993).

Chem. Pharm. Bull., "Synthesis of Biologically Active Pentapeptide Analogs of the N–Terminal Part of Lipoprotein From the Outer Membrane of *Escherichia coli*" Kurimura et al., 38 (4), pp. 1110–1112 (1990).

Peptide Chemistry 1990: Y. Shimonishi (Ed.), Protein Research Foundation, Osaka, Japan (1990), "Synthesis and Mitogenic Activity of Lipopeptide and Its Analogs" Kurimura et al., pp. 37–42.

Peptide Chemistry 1991: A. Suzuki (Ed.) Protein Research Foundation, Osaka, Japan (1991), "Stereospecific Synthesis and Mitogenic Activity of Lipopeptide WS 1279 and Its Derivatives" Kurimura et al., pp. 361–366.

Int. J. Peptide Protein Res., "Synthesis of Novel Immunologically Active Tripalmitoyl–S–Glycerylcysteinyl Lipopeptides as Useful Intermediates for Immunogen Preparations" Metzger et al., 37, 1991, pp. 46–57.

*Primary Examiner*—Jill Warden
*Assistant Examiner*—Sheela J. Huff
*Attorney, Agent, or Firm*—Wenderoth, Lind & Ponack

[57] ABSTRACT

A compound of the formula:

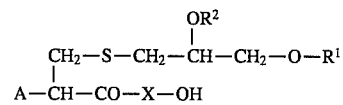

wherein each of $R^1$ and $R^2$ is hydrogen or aliphatic acyl, A is amino which may be protected, X is an amino acid sequence consisting of 1 to 10 amino acid residues which contain at least one amino acid residue having a water-solubility enhancing group, or a salt thereof has an activity of remarkably improving hematopoietic disorder and is useful as an immuno-stimulating agent or an agent for treating thrombocytopenia.

39 Claims, No Drawings

2-AMINO-6,7-DIHYDROXY-4-THIAHEPTANOIC ACID DERIVATIVES, PRODUCTION AND USE THEREOF

BACKGROUND OF THE INVENTION

1. Field of the Invention

This invention relates to 2-amino-6,7-dihydroxy-4-thiaheptanoic acid derivatives, which are useful as therapeutic agents in the treatment of leukocytopenia resulting from various causes such as, diseases due to decrease of leukocytes, diseases requiring, from the therapeutic viewpoint an, increase of bone marrow cells or leukocytes, thrombocytopenia caused by various reasons, diseases due to decrease of thrombocyte, or diseases requiring, from the therapeutic viewpoint, increase of thrombocyte.

2. Description of Related Art

In Hoppe-Seyler's Zeitschrift für Physiologiche Chemie 364, pp 593–606 (1983), a synthetic peptide derived from lipoprotein produced by *E. coli*, which is shown by the formula:

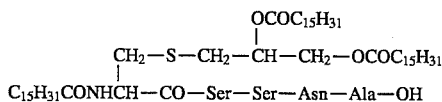

is disclosed.

And, in JPA H4(1992)-046194, WS 1279A substance shown by the formula:

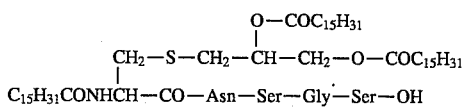

is disclosed.

Achiwa et al. synthesized these compounds as optical active compounds. [cf. JPA H4(1992)-099796, Chem. Pharm. Bull. 39, p 2590 (1991) and Peptide Chemistry, p. 361 (1991)].

However, the compounds of this invention are not described in these references.

Incidentally, abbreviations of amino acid, peptide or the like used in the present invention are based on those in accordance with IUPAC-IUB Commission on Biochemical Nomenclature or those conventionally used in the relevant fields, and, possible optical isomers of amino acid are, unless otherwise specified, L-isomers.

Chemotherapy or radiotherapy of cancers causes serious leukocytopenia or serious thromobocytopenia. The former induces a lowering of resistance against infections or other various diseases so that sufficient therapeutic effects are not expected. The latter induces insufficiency of a hemostatic mechanism so that sufficient therapeutic effects are not expected. These are being taken up as a grave concern in the field of cancer therapy. Under such circumstances, development of drugs, which mitigate the suppression of hematopoietic function caused by these therapeutic methods and are capable of promoting the recovery of leukocyte number or thrombocyte number, has been ardently desired. Further, in the therapy by bone marrow transplantation, drugs capable of promoting the proliferation of bone marrow cells then transplanted and capable of recovering the number of leukocyte promptly are desired. Furthermore, these drugs can be used for therapeutic agents of thrombocytopenia after bone marrow transplantation or autoimmunodisease accompanied by thombocytopenia, such as a plastic anemia and paroxymal thrombocytopenic purpura.

While taking the present circumstances mentioned above into consideration, the present inventors pursued their studies, from a fresh viewpoint, on compounds having the action of increasing the number of leukocytes. As the result, the present inventors found that the novel 2-amino-6,7-dihydroxy-4-thiaheptanoic acid derivatives of this invention promote the proliferation of bone marrow cells of mice and increase the number of peripheral leukocytes. Further, said compounds also stimulate bone marrow cells of mice so as to promote proliferation and differentiation of megakaryocytes. Based on these findings, the present inventors made further studies to complete the present invention.

SUMMARY OF THE INVENTION

This invention provides:

A compound of the formula (I):

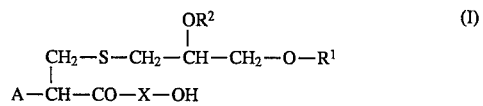

wherein each of $R^1$ and $R^2$ is hydrogen or aliphatic acyl, A is amino which may be protected, X is an amino acid sequence consisting of 1 to 10 amino acid residues which contain at least one amino acid residue having a water-solubility enhancing group, or a salt thereof.

2) A compound according to 1), wherein A is amino.

3) A compound according to 1), wherein A is amino which may be substituted with substituted oxycarbonyl.

4) A compound according to 1), wherein the amino acid residue having a water-solubility enhancing group is an acidic amino acid residue.

5) A compound according to 1), wherein the amino acid residue having a water-solubility enhancing group is a basic amino acid residue.

6) A compound according to 1), wherein aliphatic acyl is $C_{2-30}$ aliphatic acyl.

7) A compound according to 1), wherein at least one of $R^1$ and $R^2$ is aliphatic acyl.

8) A compound according to 1), wherein $R^1$ is aliphatic acyl.

9) A compound according to 1), wherein $R^2$ is aliphatic acyl.

10) A compound according to 1), wherein the compound is (2R,6R)-2-amino-6,7-bis(hexadecanoyloxy)-4-thiaheptanoyl-glycyl-glutamyl-glutamic acid.

11) A compound according to 1), wherein the compound is (2R,6R)-2-amino-6,7-bis(hexadecanoyloxy)-4-thiaheptanoyl-glycyl-glycyl-glutamic acid.

12) A compound according to 1), wherein the compound is (2R,6R)-2-amino-6,7-bis(hexadecanoyloxy)-4-thiaheptanoyl-glutamyl-glycyl-glutamic acid.

13) A compound according to 1), wherein the compound is (2R,6R)-2-amino-6,7-bis(hexadecanoyloxy)-4-thiaheptanoyl-glycyl-D-glutamic acid.

14) An immuno-stimulating composition having a leukocyte-increasing action, which comprises a compound or a salt thereof as defined in 1).

15) An immuno-stimulating composition according to 14), wherein at least one of $R^1$ and $R^2$ is aliphatic acyl.

16) A composition for treating thrombocytopenia, which comprises a compound or a salt thereof as defined in 1).

17) A method of producing the compound or a salt thereof as defined in 1), which comprises subjecting a compound of the formula (II):

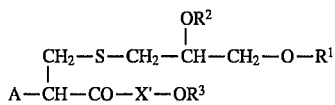

(II)

wherein each of $R^1$ and $R^2$ is hydrogen or aliphatic acyl, $R^3$ is a protecting group, A is amino which may be protected, X' is an amino acid sequence consisting of 1 to 10 optionally protected amino acid residues which contain at least one optionally protected amino acid residue having a water-solubility enhancing group, or its salt, to a deprotection reaction.

DETAILED DESCRIPTION OF THE INVENTION

Referring to the formulae (I) and (II), examples of the aliphatic acyl group shown by $R^1$ or $R^2$ include aliphatic acyl groups derived from aliphatic carboxylic acid. Examples of the aliphatic acyl groups include saturated or unsaturated aliphatic acyl groups having a maximum of 34 carbon atoms (e.g. formyl, acetyl, propionyl, butyryl, isobutyryl, valeryl, isovaleryl, hexanoyl, heptnoyl octanoyl, decanoyl, dodecanoyl, tridecanoyl, tetradecanoyl, pentadecanoyl, hexadecanoyl, heptadecanoyl, octadecanoyl, nonadecanoyl, tetracosanoyl, hexacosanoyl, icosanoyl, heneicosanoyl, docosanoyl, tetracosanoyl, hexacosanoyl, ethyldodecanoyl, methyltridecanoyl, ethyltridecanoyl, methyltetradecanoyl, ethyltetradecanoyl, methylpentadecanoyl, ethylpentadecanoyl, methylhexadecanoyl, ethylhexadecanoyl, methylheptadecanoyl, ethylheptadecanoyl, methyloctadecanoyl, ethylocatadecanoyl, octacosanoyl, triacontanyl, dotriancotanyol, tetratrianiotanoyl, acryloyl, propioloyl, methacryloyl, crotonoyl, isocrotonoyl, myristoleoyl, oleoyl, palmitoleoyl, elaidoyl, cis, cis-9,12-octadecatrienoyl, 9,12,15-octadecatrienoyl, 9,11,13-octadecatrienoyl, 5,8,11,14-icosatetraenoyl, cis-15-tetracosaenoyl, etc.).

Preferable examples of aliphatic acyl groups include $C_{2-30}$ saturated or unsaturated aliphatic acyl groups (e.g. acetyl, propionyl, butyryl, isobutyryl, valeryl, isovaleryl, hexanoyl, heptanoyl, octanoyl, decanoyl, dodecanoyl, tridecanoyl, tetradecanoyl, pentadecanoyl, hexadecanoyl, heptadecanoyl, octadecanoyl, nonadecanoyl, icosanoyl, heneicosanoyl, docosanoyl, ethyldodecanoyl, methyltridecanoyl, ethyltridecanoyl, methyltetradecanoyl, ethyltetradecanoyl, methylpentadecanoyl, ethylpentadecanoyl, methylhexadecanoyl, ethylhexadecanoyl, methylheptadecanoyl, ethylheptadecanoyl, methyloctadecanoyl, ethylocatadecanoyl tetracosanoyl, hexacosanoyl, octacosanyol, triacontanoyl, myristoleoyl, oleoyl, palmitoleoyl, elaidoyl, cis, cis-9,12-octadecatrienoyl, 9,12,15-octadecatrienoyl, 9,11,13-octadecatrienoyl, 5,8,11,14-icosatetraenoyl, cis-15-tetracosaenoyl, etc.).

Especially preferable examples of the aliphatic acyl groups shown by $R^1$ or $R^2$ include $C_{2-16}$ saturated or unsaturated aliphatic acyl groups.

Preferably, at least one of $R^1$ and $R^2$ is an aliphatic acyl group.

More preferably, both $R^1$ and $R^2$ are an aliphatic acyl group.

In the above formulae (I) and (II), examples of protective groups in the optionally protected amino groups shown by A include formyl, C6–14 arylcarbonyl (e.g. phenyl carbonyl), substituted oxycarbonyl [e.g. $C_{1-6}$ alkyloxy carbonyl (e.g. methoxy carbonyl, ethoxycarbonyl, etc.), C6–14 (e.g. aryloxycarbonyl phenyloxy carbonyl, etc.), 9-fluorenylmethyloxy carbonyl, C7–19 aralkyloxy-carbonyl (e.g. benzyloxycarbonyl, etc.), adamantyloxy-carbonyl and so on], C7–19 aralkyl-carbonyl (e.g. benzylcarbonyl, etc.), and C7–19 aralkyl (e.g. benzyl, benzhydryl, trityl, etc.) and phthaloyl. These protective groups other than formyl may be substituted. Examples of the substituents include halogen atoms (e.g. fluoro, chloro, bromo and iodo), $C_{1-6}$ alkyl carbonyl (e.g. acetyl, ethyl carbonyl, butyl carbonyl, etc.) and nitro group. The number of substituents ranges from 1 to 3.

A has preferably the above-mentioned meanings when $R^1$ and $R^2$ are both aliphatic acyl groups.

Preferably, A is an amino group which may be protected by the substituted oxycarbonyl. More preferably, A is an amino group.

In the formula (I), the amino acid in the amino acid sequence shown by X means a compound having in its molecule an amino group and an acidic group (e.g. carboxyl group, sulfonic acid group). Preferable examples of the amino acid include those described in Dai Yuhki Kagaku (Encyclopedia of Organic Chemistry) Vol. 21 "Natural Polymers III" compiled under the supervision of Dr. Munio Kotake, Published by Asakura Shoten in Japan, 1960 and "Amino acids and peptides" by Chapman and Hall, compiled by J. S. Davies, 1985 in USA.

To state more concretely, there may be mentioned, for example, amino acid constituting protein [e.g. aliphatic monoamino monocarboxylic acid such as glycine, alanine, valine, leucine, isoleucine or the like, aliphatic hydroxyamino acid such as serine, threonine or the like, acidic amino acid such as aspartic acid, glutamic acid or the like, acidic amino acid amide such as aspargine, glutamine or the like, aromatic amino acid such as phenylalanine, tyrosine, tryptophane or the like, iminocarboxylic acid such as proline, hydroxyproline or the like, basic amino acid such as arginine, lysine, histidine or the like, and sulfur-containing amino acid such as methionine, cystine, cysteine or the like], amino acid obtained from natural sources as, for example, metabolites of microorganisms or components of animals and plants [e.g. aliphatic monoamino monocarboxylic acid such as L-α-aminobutyric acid, γ-aminobutyric acid, β-aminoisobutyric acid, β-alanine, homoserine, α-methyl-D-serine, O-carbamyl-D-serine, δ-hydroxy-γ-oxo-norvaline, or the like, monoamino dicarboxylic acid such as L-α-aminoadipic acid, L-β-aminoadipic acid, L-theanine, L-γ-methylene glutamic acid, L-γ-methyl glutamic acid or the like, diaminomonocarboxylic acid such as L-ornithine, β-lysine, α,β-diaminopropionic acid, L-α,γ-diaminobutyric acid, or the like, diaminodicarboxylic acid such as diaminopimelic acid or the like, sulfonic acid-containing monoaminomonocarboxylic acid such as cysteic acid or the like, sulfonic acid-containing amino acid such as taurine or the like, aromatic amino acid such as kynurenine, 3,4-dioxyphenyl-L-alanine or the like, heterocyclic amino acid such as 2,3-dicarboxyaziridine, [S]-2-amino-3-(isoxazolin-5-one-4-yl)-propionic acid, anticapsin or the like, basic amino acid such as L-4-oxalysine, L-4-oxolysine, [3R,5R]-3,6-diamino-5-hydroxyhexanoic acid, or the like, sulfur-containing amino acid such as lanthionine, S-methyl-L- cysteine or the like, cyclic amino acid such as pipecolic acid, azetidine-2-carboxylic acid, [1R, 2S]-2-aminocyclopentane-1-carboxylic acid, or the like, amino acid substituted with a specific functional group such as citrulline, alanosine, L-azaserine, or the like], and amino acids obtained by organic synthesis [e.g. 6-aminohexanoic acid, 8-aminooctanoic acid, 12-aminododecanoic acid, 4-aminobenzoic acid, 4-(aminomethyl)benzoic acid, 4-(N-(carboxymethyl)aminomethyl)benzoic acid, etc.]

The amino acid residue means a divalent group which is derived from amino acid and has bonds to the amino group and acidic group, respectively.

Incidentally, even the group is unstable as amino acid, in the case where the amino group is acylated or the acidic group has amido-linkage, the group can be used as an amino acid residual group. Examples of such amino acid include (6-aminohexyl)carbamic acid.

Referring to the formula (I), examples of the amino acid having a water-solubility enhancing group in the amino acid sequence shown by X include the above-mentioned acidic amino acid and basic amino acid, preferably, the acidic amino acid.

Examples of the acidic amino acid include a compound having one or more acidic functional groups (e.g. carboxyl group, sulfonic acid group, etc.) in addition to a carboxyl group and an amino group. Preferable examples of the acidic amino acid include a compound having one amino group and two or more carboxyl groups. To state more concretely, there may be mentioned, for example, amino dicarboxylic acid (e.g. aspartic acid, glutamic acid, L-α-aminoadipic acid, L-β-aminoadipic acid, 2,3-dicarboxyaziridine, etc.), more preferably, α-aminodicarboxylic acid (e.g. aspartic acid, glutamic acid, L-α-aminoadipic acid, etc.), and, among them, aspartic acid and glutamic acid are especially preferable.

Examples of the basic amino acid include a compound having one or more basic functional groups (e.g. amino, a basic nitrogen containing heterocyclic group such as imidazolyl, indolyl, etc., guanidino, and so on). Preferable examples of the basic amino acid include a compound having one amino group, one carboxyl group and one or more said basic functional groups.

To state more concretely, there may be mentioned, for example, a basic amino acid constituting protein (e.g. arginine, lysine, histidine, etc.) and a basic amino acid obtained form natural sources as, for example, metabolites of microorganisms or components of animals and plants (e.g. diamino carboxylic acid such as L-ornithine, β-lysine, α, β-diaminopropionic acid, L-α, γ-diaminobutyric acid, or the like, L-4-oxalysine, L-4-oxolysine, [3R,5R]-3,6-diamino-5-hydroxyhexanoic acid, etc.), more preferably, a basic α-amino acid constituting protein (e.g. arginine, lysine, histidine, etc.) and a basic α-amino acid obtained from natural sources as, for example, metabolites of microorganisms or components of animals and plants (e.g. L-ornithine, β-lysine, α, β-diaminopropionic acid, L-α, γ-diaminobutyric acid, L-4-oxalysine, L-4-oxolysine, etc.), and among them, lysine, arginine and histidine are especially preferable.

In the formula (II), as the protecting groups shown by $R^3$, use is preferably made of protecting groups of carboxyl group described later.

In the formula (II), the amino acid in the optionally protected amino acid residue in the amino acid sequence shown by X' has the same meaning as that in the amino acid residue in the afore-mentioned amino acid sequence shown by X.

In the formula (II), the amino acid in the optionally protected amino acid residue having a group which enhances the water-solubility of the amino acid sequence shown by X' has the same meaning as that in the amino acid residue having a group which enhances the water-solubility of the afore-mentioned amino acid sequence shown by X.

As the protecting group, mention is made of known protecting groups employed for protecting amino group, carboxyl group or hydroxyl group in peptide synthesis. These are protecting groups which can be removed by, for example, hydrolysis, hydrogenolysis, reduction, aminolysis or hydrazinolysis.

Examples of the amino-protecting groups include urethane-type protecting groups (e.g. benzyloxycarbonyl, t-butoxycarbonyl, allyloxycarbonyl, t-amyloxycarbonyl, isobornyloxycarbonyl, 4-methoxybenzyloxycarbonyl, 2-chlorobenzyloxycarbonyl, adamantyloxycarbonyl, 9-fluorenylmethyloxycarbonyl, 2,2,2-trichloroethyloxycarbonyl, or the like), acyl-type protecting groups (e.g. $C_{1-6}$ lower fatty acid residues optionally having such a substituent as halogen, e.g. formyl, acetyl, propyl, trifluoroacetyl, chloroacetyl, or the like, phthalyl, tosyl, 2-nitrosulfenyl, 4-methoxy-2-nitrosulfenyl, benzoyl, or the like), and alkyl-type protecting groups (e.g. trityl, benzyl or the like).

Among these, urethane-type protecting groups are especially preferable.

Carboxyl groups are protected by converting them into, for example, amido group, hydrazido group or ester. Preferable amido groups or hydrazido groups are those substituted with a suitable substituent. Preferable amido groups are those substituted with a $C_{7-19}$ aralkyl group optionally substituted with, for example, alkoxy group (e.g. 3,4-dimethoxybenzyl group or bis-(p-methoxyphenyl)-methyl group). Preferable hydrazido groups are those substituted with, for example, $C_{1-6}$ alkyloxycarbonyl group optionally substituted with halogen (e.g. fluorine, chlorine, bromine, etc.) $C_{6-12}$ aryl group (e.g. phenyl, p-biphenylyl, etc.) (e.g. benzyloxycarbonyl group, trichloroethyloxycarbonyl group, tert-butyloxycarbonyl group, 2-(p-biphenylyl)-isopropyloxycarbonyl, etc.), halogenated $C_{2-6}$ alkanoyl group (e.g. trifluoroacetyl group, etc.) and $C_{7-9}$ aralkyl group (e.g. trityl group, etc.), among others. Further, the carboxyl groups may be protected as esters with an optionally substituted lower alcohol (e.g. methanol, ethanol, cyanomethyl alcohol, benzoylmethyl alcohol, tert-butanol, etc.), aralkanol [e.g. benzyl alcohol or benzhydrols (e.g. benzhydrol, p-nitrobenzyl alcohol, p-methoxybenzyl alcohol, 2,4,6-trimethylbenzyl alcohol, etc.) optionally substituted with, for example, lower alkyl group, lower alkoxy group or or halogen atom], phenol and thiophenol optionally substituted with an electron withdrawing group (e.g. thiophenol, thiocresol, p-nitrothiophenol, 2,4,5- and 2,4,6-trichlorophenol, p-cyanophenol, p-methanesulfonyl phenol, etc.), and further, with N-hydroxyimide (e.g. N-hydroxysuccinimide, N-hydroxyphthalimide, etc.), N-hydroxypiperidine, 8-hydroxyquinoline or the like.

As the special protecting group of carboxyl, which can be removed under neutral reaction conditions, mention is made of a hydrocarbyl-silyl-ethyl group, for example, 2-(trimethylsilyl)-ethyl group (described in German Patent Application Laid-Open No.2,706,490).

Hydroxyl can be protected with, for example, acylation or etherification.

The especially preferable acyl group in the case of acylation is a group derived from carbonic acid (e.g. benzyloxycarbonyl group or ethyloxycarbonyl group). For etherification, benzyl group, tetrahydropyranyl group or tert-butyl group, for example, is preferable. And, for the protection of hydroxyl group, 2,2,2-trifluoro-1-tertbutoxycarbonylamino ethyl group or 2,2,2-trifluoro-1-benzyloxycarbonylamino ethyl group [Chem. Ber., Vol. 100 (1967), pp 3838–3849] is preferably employed.

In the formula (I), in the case where the amino acid residue is possibly an optically active isomer, it can take any of L-, D- and DL-form.

The prefered examples of compound (I) or a salt thereof include (2R,6R)-2-amino-6,7-bis(hexadecanoyloxy)-4-thiaheptanoyl-Gly-Glu-Glu-OH, (2R,6R)-2-amino-6,7-bis(hexadecanoyloxy)-4-thiaheptanoyl-Gly-Gly-Glu-OH, (2R,6R)-2-amino-6,7-bis(hexadecanoyloxy)-4-thiaheptanoyl-Glu-Gly-Glu-OH, (2R,6R)-2-amino-6,7-bis(hexadecanoyloxy)-4-thiaheptanoyl-Gly-D-Glu-OH, or salts thereof.

In the following, description is made on the method of producing the above-mentioned compounds.

Protective groups and reagents frequently used are abbreviated as follows in the subsequent description.

Fmoc: 9-fluorenyl methyloxycarbonyl

Z: benzyloxy carbonyl

Bu: t-butyl

O'Bu: t-butoxyester

TFA: trifluoroacetic acid

TEA: triethylamine

DMF: N,N-dimethylformamide

DCC: N,N'-dicyclohexylcarbodiimide

BOP: benzotriazol-1-yloxy tris (dimethylamino) phosphonium.hexafluorophosphate

DIC: N,N'-diisopropylcarbodiimide

HONB: N-hydroxy-5-norbonen-2,3-dicarboxyimide

DEPC: diethyl phosphorocyanidate

HOBT: 1-hydroxybenzotriazole

DCM: dichloromethane

MeOH: methanol

THF: tetrahydrofuran

WSC: water-soluble carbodiimide.hydrochloride

DMAP: 4-dimethylaminopyridine

Boc: t-butoxycarbonyl

R-: R-configuration

S-: S-configuration

The compound, which is the basic skeleton of the compounds in this specification is 2-amino-6,7-dihydroxy-4-thiaheptanoic acid.

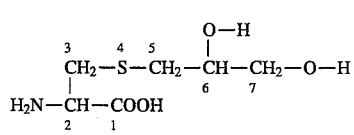

In this specification, thiaheptanoyl is abbreviated as THT, thiaheptanoic acid is abbreviated as THT-OH. And, octadecanoyl is abbreviated as Ste, hexadecanoyl as Pam, tetradecanoyl as Myr, and octadecanoyloxy as SteO, hexadecanoyloxy as PamO tetradecanoyloxy as MyrO.

Compounds represented by the formula (I) or salts thereof can be produced by subjecting a compound represented by the formula (II) or a salt thereof to deprotection reaction.

The deprotection reaction can be conducted by a per se known method, for example, a method conventionally employed in the field of peptide chemistry. [cf. Synthetic Chemistry Series, Peptide Synthesis, authors: IZUMIYA Nobuo, UNO Motonori, KATO Tetsuo & AOYAGI Haruhiko; Published by Maruzen Co. Ltd. 1975 in Japan].

Deprotection reaction on the amino group protected with a urethane-type protecting group is conducted by bringing the amino group into contact with an acid in the absence of solvent or in a solvent which gives no adverse influence on the reaction. As the solvent, use is made of halogenated hydrocarbons (e.g. dichloromethane, chloroform, 1,2-dichloroethane, etc.), alcohols (e.g. methanol, ethanol, etc.), water and a mixture of them in an appropriate ratio. This reaction is conducted by bringing the compound (II) or a salt thereof into contact with an acid. As the acid, use is made of, for example, haloacetic acid (e.g. trifluoroacetic acid, etc.), hydrohalogenic acid (e.g. hydrochloric acid, hydrobromic acid, etc.), among others. It is advantageous that N-benzyloxycarbonyl group and N-4-methoxybenzyloxycarbonyl group are removed by catalytic hydrogenation by using, for example, palladium catalyst (e.g. palladium carbon, palladium-barium sulfate, palladium black, etc.) or rhodium catalyst. In this case, a known solvent, for example, cyclic ether (e.g. tetrahydrofuran, etc.), alcohols (e.g. methanol, ethanol, etc.) etc., or, depending on cases, a mixture of cyclic ether and other inert solvents [e.g. lower aliphatic acid amide (e.g. dimethylformamide, etc.) etc.] is used.

N-9-Fluorenylmethyloxycarbonyl group is removed advantageously by using an organic amine, for example, diethylamine, piperidine, morpholine, 4-dimethylaminopyridine or dicyclohexylamine. The reaction is conducted in a solvent which gives no adverse reaction on the reaction. As the solvent, use is made of, for example, amides (e.g. dimethylformamide, acetamide, etc.), alcohols (e.g. methanol, ethanol, etc.), halogenated hydrocarbons (e.g. chloroform, dichloromethane, 1,2-dichloroethane, etc.), etc., or a mixture of them in an appropriate ratio.

It is advantageous that, N-2,2,2-trichloroethyloxycarbonyl group is removed by using a metal (e.g. zinc, etc.) together with an organic carboxylic acid (e.g. acetic acid, propionic acid, etc.). The reaction is conducted in a solvent which gives no adverse influence on the reaction. As the solvent, use is made of the above-mentioned carboxylic acid, alcohols (e.g. methanol, ethanol, etc.) water or a mixture of them in an appropriate ratio.

Deprotection reaction (deacylation reaction) of acylated hydroxy group is conducted by bringing it into contact with an acid in a solvent which gives no adverse influence. As the solvent, use is made of halogenated hydrocarbons (e.g. dichloromethane, chloroform, 1,2-dichloroethane, etc.), alcohols (e.g. methanol, ethanol, etc.), water and a mixture of them in an appropriate ratio. This reaction is conducted by bringing the compound (II) or a salt thereof into contact with an acid. As the acid, use is made of, for example, haloacetic acid (e.g. trifluoroacetic acid, etc.), hydrohalogenic acid (e.g. hydrochloric acid, hydrobromic acid, etc.), etc.

Elimination of O-benzyl group is performed advantageously by catalytic hydrogenation with, for example, a palladium catalyst such as palladium carbon, palladium/barium sulfate and palladium black, or a rhodium catalyst, using, in this case, a known solvent, for example, cyclic ether (e.g. tetrahydrofuran, etc.) as a mixture with other inactive solvents [e.g. lower aliphatic acid amide (dimethylformamide or the like) etc.].

Elimination of O-tetrahydropyranyl group or O-tert-butyl group can be performed, like in the above-mentioned deacylation, by hydrolysis with an acid.

Elimination of a carboxyl-protecting group can be performed, like in the above-mentioned case, by hydrolysis with an acid. And, benzyl ester, for example, can be deprotected by catalytic hydrogenation like in the case of the above-mentioned deprotection of the O-benzyl group elimination. The above-mentioned 2-(trimethylsilyl)-ethyl group can be eliminated by the action of, for example, a salt of hydrofluoric acid, for example, especially a salt of quaternary nitrogen base with hydrofluoric acid (e.g. tetraethyl ammonium fluoride, etc.) in a suitable solvent under neutral conditions.

The compound represented by the general formula (II) or a salt thereof, which is the starting compound used for the production of the afore-mentioned general formula (I) or a salt thereof, can be produced by subjecting a material having a reactive carboxyl group corresponding to one of the two fragments separated at an optional position of the peptide linkage and a material having a reactive amino group corresponding to the other fragment to condensation by a conventional means employed in peptide synthesis.

As the conventional means of peptide synthesis, mention is made of, for example, anyone of liquid-phase synthetic method and solid-phase synthetic method. Such means of peptide synthesis as mentioned above include, for example, methods described in "Peptide Synthesis" written by M. Bondosky and M. Ondetti, Interscience, New York, 1966; "The Proteins" written by F. M. Finn and K. Hoffmann, Vol.2, edited by H. Nenrath and R. L. Hill, Academic Press Inc. New York, 1976; "Base & Experiment of Peptide Synthesis" written by IZUMIYA Nobuo, Maruzen Co. Ltd., 1985; "Seikagaku Jikken Koza 1" written by YAJIMA Haruaki, SAKAKIBARA Shunpei, et al. compiled by Japan Biochemistry Society, Tokyo Kagaku Dojin, 1977, "Zoku Seikagaku Jikken Koza 2" written by KIMURA Shun et al. compiled by Japan Biochemistry Society, Tokyo Kagaku Dojin, 1987; "Solid Phase Peptide Synthesis" written by J. M. Slewart and J. D. Young, Pizs chemical company, Illinois, 1984, or methods analogous to them. Practical examples of such methods as above includes, for example, azide method, chloride method, acid anhydride method, mixed acid anhydrides method, DCC method, active ester method, method using Woodword reagent K, carbonyl imidazole method, redoc method, DCC/HONB method, DIC/HONB method, DCC/HONB method, method using BOP reagent, method using DEPC reagent or the like.

As preferable practical examples of one of the starting fragments, in the case of producing the above-mentioned compound (II) or a salt thereof, mention is made of, for example, a compound represented by the general formula (III):

H—X'—OR³     (III)

wherein X' and R³ are of the same meaning as defined above or salts thereof.

The compound (III) or salts thereof can be produced by, far example, the above-mentioned conventional means for peptide synthesis.

Preferable examples of the compound (III) include the following compounds.

| Compound No. | Structural Formula |
|---|---|
| P-1 | H—Gly—Gly—Gly—Glu(O$^t$Bu)-Thr($^t$Bu)-Thr($^t$Bu)-O$^t$Bu |
| P-2 | H—Gly—Gly—Gly—Glu(O$^t$Bu)-Thr(O$^t$Bu)-O$^t$Bu |
| P-3 | H—Glu(O$^t$Bu)-Gly—Glu(O$^t$Bu)-Gly-D-Glu(O$^t$Bu)- |

-continued

| Compound No. | Structural Formula |
|---|---|
| P-4 | O$^t$Bu<br>H—Gly—Gly—Gly—Glu(O$^t$Bu)-O$^t$Bu |
| P-5 | H—Gly—Gly—Gly-D-Glu(O$^t$Bu)-O$^t$Bu |
| P-6 | H—Glu(O$^t$Bu)-Gly-D-Glu(O$^t$Bu)-O$^t$Bu |
| P-7 | H—Gly—Gly—Glu(O$^t$Bu)-O$^t$Bu |
| P-8 | H—Gly—Gly—Gly—Asp(O$^t$-Bu)-O$^t$Bu |
| P-9 | H—Gly—Gly-D-Glu(O$^t$Bu)-O$^t$Bu |
| P-10 | H—Gly-D-Glu(O$^t$Bu)-O$^t$Bu |
| P-11 | H—Gly—Glu(O$^t$Bu)-Glu(O$^t$Bu)-O$^t$Bu |
| P-12 | H—Gly—Glu(O$^t$Bu)-D-Glu(O$^t$Bu)-O$^t$Bu |
| P-13 | H—Glu(O$^t$Bu)-Gly—Glu(O$^t$Bu)-O$^t$Bu |
| P-14 | H—Glu(O$^t$Bu)-D-Glu(O$^t$Bu)-O$^t$Bu |
| P-15 | H—Glu(O$^t$Bu)-Glu(O$^t$Bu)-Glu(O$^t$Bu)-O$^t$Bu |
| P-16 | H—Glu(O$^t$Bu)-Glu(O$^t$Bu)-D-Glu(O$^t$Bu)-O$^t$Bu |
| P-17 | NH$_2$(CH$_2$)$_7$CO—Glu(O$^t$Bu)-O$^t$Bu |
| P-18 | NH$_2$(CH$_2$)$_{11}$CO—Glu(O$^t$Bu)-O$^t$Bu |
| P-19 | 4-aminobenzoyl-Glu(O$^t$Bu)-O$^t$-Bu |
| P-20 | 4-(glycylamino) benzoyl-Glu(O$^t$Bu)-O$^t$Bu |
| P-21 | NH$_2$(CH$_2$)$_5$CO—Glu(O$^t$Bu)-O$^t$Bu |
| P-22 | NH$_2$(CH$_2$)$_6$NHCO—Glu(O$^t$Bu)-O$^t$Bu |
| P-23 | 4-(aminomethyl)benzoyl-Glu(O$^t$Bu)-O$^t$Bu hydrochloride |
| P-24 | 4-(N-(t-butyloxycarbonylmethyl)aminomethyl)benzoyl-Glu(O$^t$Bu)-O$^t$Bu |
| P-25 | H—Gly—Lys(Boc)—Gly—O$^t$Bu |

As the starting fragment for producing the compound (II) by combination with the above-mentioned compound (III), use is made of a compound represented by the formula (IV):

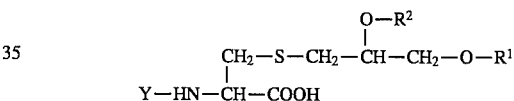

wherein Y stands for an amino-protecting group; R$^1$ and R$^2$ are of the same meaning as defined above.

The amino-protecting group represented by Y in the above-mentioned general formula (IV) has the same meaning as defined for the afore-described amino-protecting group.

The compound (IV) or a salt thereof, wherein R$^1$ and R$^2$ stand for one and the same group, can be produced by adequately applying a per se known method [e.g. International Journal of Peptide and Protein Research, ,38 1991 pp.545–554; Chemical and Pharmaceutical Bulletin, 39 pp.2590–2596].

In the case where R$^1$ and R$^2$ are different groups from each other, the most common production route is described below.

First, the monoacyl compound of a glycerin derivative, for example, glycidol or epichlorohydrin, is prepared. On the other hand, the disulfide linkage of cystine in which amino group and carboxyl group are protected is opened reductively to give a cysteine derivative.

By subjecting this cysteine derivative to addition reaction to the above-mentioned monoacyl glycerine derivative, 2-amino-6-hydroxy-7-acyloxy-4-thiaheptanoic acid in which the amino group and carboxyl group are protected.

In this reaction, use of R-(+)-glycidol gives a (6R)-2-amino-6-hydroxy-7-acyloxy-4-thiaheptanoic acid derivative, while use of S-(–)-glycidol gives a (6S)-2-amino-6-hydroxy-7-acyloxy-4-thiaheptanoic acid derivative.

By conventional acylation of the hydroxyl group at 6-position of 2-amino-6-hydroxy-7-acyloxy-4-thiaheptanoic acid obtained by the above-mentioned reaction, a 2-amino-6,7-bis(acyloxy)-4-thiaheptanoic acid derivative having a different O-acyl group can be obtained.

By directly using, for example, glycidol instead of an acyl glycerine derivative, 2-amino-6,7-dihydroxy-4-thiaheptanoic acid derivative is obtained, and, acylation of this product by a conventional method conveniently gives 2-amino-6,7-bis(acyloxy)-4-thiaheptanoic acid derivative having the same O-acyl group.

By removing, in the above-mentioned manner, the protecting group of the carboxyl group of the 2-amino-6,7-bis(acyloxy)-4-thiaheptanoic acid derivative thus obtained, 2-amino-6,7-bis(acyloxy)-4-thiaheptanoic acid having protected amino group can be prepared.

Preferable examples of the compound (IV) include 2-amino-6,7-bis(acyloxy)-4-thiaheptanoic acid having protected amino group.

Further examples are shown below:

| Compound No. | Structural Formula |
|---|---|
| GC-1 | (2R,6S)-2-Fmoc-amino-6,7-bis(PamO)-4-THT-OH |
| GC-2 | (2R,6R)-2-Fmoc-amino-6,7-bis(PamO)-4-THT-OH |
| GC-3 | (2S,6R)-2-Fmoc-amino-6,7-bis(PamO)-4-THT-OH |
| GC-4 | (2S,6S)-2-Fmoc-amino-6,7-bis(PamO)-4-THT-OH |
| GC-5 | (2R,6R)-2-Fmoc-amino-6-hexanoyloxy-7-PamO-4-THT-OH |
| GC-6 | (2R,6R)-2-Fmoc-amino-6,7-bis(SteO)-4-THT-OH |
| GC-7 | (2R,6R)-2-Fmoc-amino-6,7-bis(MyrO)-4-THT-OH |

The starting fragments obtained thus above are subjected to condensation in the following manner, and then, if necessary, the amino-protecting group shown by Y is removed to give the compound (II) or a salt thereof.

As the compound produced by activating the carboxyl group of the starting compound, mention is made of, for example, corresponding acid anhydrides, azides, active esters [e.g. esters with alcohol (e.g. pentachlorophenol, 2,4,5-trichlorophenol, 2,4-dinitrophenol, cyanomethyl alcohol, p-nitrophenol, N-hydroxy- 5-norbornene-2,3-dicarboxyimde, N-hydroxysuccinimide, N-hydroxyphalimide, N-hydroxybenzotriazole)]. As the starting compound whose amino group is activated, mention is made of, for example, the corresponding phosphoric acid amide.

The condensation can be conducted in the presence of a solvent. The solvent can be selected from those known as being employable for peptide condensation reaction. Examples of the solvent include amides such as anhydrous or water-containing formamide, dimethylformamide, N-methyl pyrrolidone, etc., sulfoxides such as dimethyl sulfoxide, etc., aromatic amines such as pyridine, etc., halogenated hydrocarbons such as chloroform, dichloromethane, etc., ethers such as tetrahydrofuran, dioxane, etc., nitriles such as acetonitrile, etc., esters such as ethyl acetate, ethyl formate, etc., or a mixture of them in an appropriate ratio.

The reaction temperatures can be adequately selected from the range known as being employable for peptide linkage forming reaction, specifically, for example, usually from about −20° C. to 40° C.

The reaction time can be adequately selected from the range known as being required for peptide linkage formation reaction, specifically, for example, from about several minutes to about 48 hours.

Removal of the amino-protecting group shown by Y is conducted in substantially the same manner as described above.

The compound (I) or a salt thereof thus produced can be recovered, after completion of the reaction, by means for separating peptide, for example, extraction, partition, reprecipitation, crystallization, various chromatographic processes, high performance liquid chromatography, etc.

A salt of the compound (I) of this invention with a base, especially with a pharmaceutically acceptable base, can be obtained by a per se known method. Examples of the base include an alkali metal such as sodium, potassium, etc., an alkaline earth metal such as calcium, magnesium, etc., an organic base such as triethylamine, pyridine, etc. and so on. A salt of the compound (I) with an acid, especially a pharmaceutically acceptable acid can be obtained by a per se known method. Examples of the acid include an inorganic acid (e.g. hydrochloric acid, sulfuric acid, phosphoric acid, etc.), an organic acid (e.g. acetic acid, propionic acid, citric acid, tartaric acid, malic acid, oxalic acid, etc.) and so on.

And, as salts of the compounds (II) to (IV), use is made of those substantially the same as salts of the compound (I).

The compound (I) or salts thereof have activities of remarkably improving the state of hematopoiesis-insufficieney, which can be used as therapeutic or prophylactic agents of leukocytopenia caused by radiotherapy or chemotherapy of cancers in mammals (e.g. dog, pig, cow, horse, monkey, man, etc), as hematopoietic stimulating agents in the case of bone marrow transplantation, as immuno-stimulating agents having leucocyte-increasing action, and, further, as a therapeutic agent of thrombocytopenia.

The compound (I) or salts thereof are low in toxicity and can be used safely.

In the case of administering the compound (I) or a salt thereof to, for example, man, it can be safely administered orally or non-orally alone or as a pharmaceutical composition by mixing with a suitable pharmaceutically acceptable carrier, excipient or diluent.

Examples of the above-mentioned pharmaceutical composition include injections, orally administrable compositions (e.g. powder, granules, capsules, tablets), Topical Compositions (e.g. transnasal agent, transdermal agent, etc.), and suppositories (e.g. rectal suppositories, vaginal suppositories).

These pharmaceutical compositions can be prepared by per se known methods generally employed in the processes of pharmaceutical preparation.

For example, the compound (I) or a salt thereof of this invention can be prepared into aqueous injections together with a dispersant (e.g. Tween 80 (manufactured by Atlas Powder Co., USA), HCO 60 (manufactured by Nikko Chemicals), polyethylene glycol, carboxymethyl cellulose, sodium alginate or the like), a preservative (e.g. methylparaben, propylparaben, benzyl alcohol, chlorobutanol or the like) and an isotonicating agent (e.g. sodium chloride, glycerin, sorbitol, glucose or the like), among others, or into oleagenous injections by dissolving, suspending or emulsifying in a vegetable oil such as olive oil, sesame oil, peanut oil, cotton seed oil, corn oil or the like, propylene glycol, among others.

For preparing the compound (I) or a salt thereof of this invention into compositions for oral administration, it is subjected to compression molding, in accordance with a per se known method, together with an excipient (e.g. lactose, sucrose, starch or the like), a disintegrator (e.g. starch, calcium carbonate or the like), a binding agent (e.g. starch, gum arabica, carboxymethyl cellulose, polyvinyl pyrrolidone, hydroxypropyl cellulose or the like) or a lubricant (e.g. talc, magnesium stearate, polyethylene glycol 6000), etc., followed by, upon necessity, masking the taste or coating by a per se known process for the purpose of enteric coating or of making the compositions to be of sustained-release. Examples of the coating agent include hydroxypropyl methyl cellulose, ethyl cellulose, hydroxymethyl cellulose, hdyroxypropyl cellulose, polyoxyethylene glycol, Tween 80, Brulonick F68, cellulose acetate phthalate, hdyroxypropyl methyl cellulose phthalate, hydroxymethyl cellulose acetate succinate, Eudragit (manufactured by Rohm, Germany, methacrylic acid.acrylic acid copolymer) and a pigment such as titanium oxide, red iron oxide, etc. Subcoating layer may be provided between the enteric coating and the core according to per se known method.

For preparing the compound (I) or a salt thereof into, for example, solid, semi-solid or liquid compositions for topical use, a per se known method can be resorted to. For preparing solid compositions, for example, the compound (I) or a salt thereof is prepared into powdery compositions singly or in admixture with an excipient (e.g. glycol, mannitol, starch, microcrystalliine cellulose or the like), a thickening agent (e.g. natural rubbers, cellulose derivatives, acrylic acid polymers or the like). As the above-mentioned liquid composition, almost like in the case of injections, mention is made of oleaginous or aqueous suspensions. As the semi-solid composition, aqueous or oleagenous gel compositions or ointments are preferably counted. These compositions may be supplemented with a pH regulator (e.g. carbonic acid, phosphoric acid, citric acid, hydrochloric acid, sodium hydroxide, etc.), a preservative (e.g. para-hydroxybenzoic acid esters, chlorobutanol, benzalkonium chloride, etc.), among others.

In the case of preparing suppositories for example, the compound (I) or a salt thereof of the present invention can be prepared into oleagenous or water-soluble solid, semi-solid or liquid suppositories. As the oleagenous base for the above-mentioned compositions, any one which does not dissolve the compound (I) or a salt thereof can be employed, as exemplified by glyceride of higher fatty acid [e.g. cacao butter, Witteosols (manufactured by Dynamite Nobel, Inc.), etc.], middle class fatty acid [e.g. Migliols (manufactured by Dynamite Nobel, Inc.), etc.] or vegetable oil (e.g. sesame oil, soybean oil, cotton seed oil, etc.), among others. And, examples of the water-soluble base include polyethylene glycols and propylene glycols, and, examples of the water-soluble gel base include natural rubbers, cellulose derivatives, vinyl polymers, acrylic acid polymers, etc.

While the dosage of the compound (I) or a salt thereof when administered to man as injections varies with diseases, administration routes, ages of individual patients and states of disease, it ranges from about 0.01 µg to 20 mg in terms of the effective component, preferably from about 0.1 µg to 0.2 mg, more preferably from about 0.5 µg to 50 µg in the case of a common adult patient (50 kg body weight).

[EXAMPLES]

By the following reference examples, working examples, experimental examples and formulation examples, the present invention will be described in further detail, but they are not intended to limit the invention in any manner. The numerals showing the mixing ratio in mixed solvents mean the volume ratio of each solvent. Percent (%) means w/w%, unless specified otherwise.

$^1$H-NMR spectrum is determined by a Varian Gemini200 (200 MHz) type spectrometer using tetramethyl silane as the internal standard, expressing all the δ values as ppm.

Symbols used in the reference examples and working examples are of the following meaning.

s; singlet, d: doublet, t: triplet, q: quartet, dd: double doublet, dt: double triplet, m: multiplet, br: broad.

Reference Example 1

Production of H-Gly-Gly-Gly-Glu(O$^t$Bu)-Thr($^t$Bu)-Thr($^t$Bu)-O$^t$Bu (P-1)

H-Gly-Gly-Gly-OH (10.0 g, 52.9 mmol, prepared by Peptide Research Labs) was dissolved in a 4N aqueous solution of sodium hydroxiede (13.3 ml). To the solution were added, under ice-cooling, a 4N aqueous solution of sodium hydroxide (15.9 ml) and benzyloxycarbonylchloride (9.31 ml), then the mixture was stirred overnight at 20° C. The reaction mixture was washed with ether. To the aqueous layer was added, under ice-cooling, 5M HCl to adjust its pH to 3, which was left standing overnight at a cool place. Resulting crystalline precipitates were collected by filtration, washed with cold water and dried. The crystals thus obtained were used without purification. The yield was 13.4 g (78.5%).

Z-Gly-Gly-Gly-OH (3.04 g, 9.41 mmol) obtained thus above was dissolved in DMF (200 ml). To the solution were added, under ice-cooling, HONB (1.86 g, 10.4 mmol) and DCC (2.14 g, 10.4 mmol). The mixture was stirred for two hours under ice-cooling, then insolubles were filtered off.

Z-Glu(O$^t$Bu)-Thr($^t$Bu)-Thr($^t$Bu)-O$^t$Bu (6.66 g, 9.41 mmol) was dissolved in methanol (300 ml). To the solution was added 10% (w/w, hereinafter in the same way) palladium-carbon. The mixture was stirred for two hours in hydrogen streams at ordinary temperature under normal pressure. The catalyst was filtered off, and the solvent was distilled off. The residue was dissolved in DMF (150 ml). To the solution was added, under ice-cooling, diisopropylethylamine (1.80 ml, 10.4 mmol). The mixture was stirred, to which was added the solution prepared as above, and the mixture was stirred overnight at 20° C. then the solvent was distilled off To the residue were added chloroform and water, which was subjected to extraction with chloroform. The chloroform layer was washed with a 10% (w/v) aqueous solution of citric acid, water, a saturated aqueous solution of sodium hydrogencarbonate and water, successively, which was dried over anhydrous sodium sulfate. Then, the solvent was distilled off. The residue was purified by means of a silica-gel column chromatography [5% (v/v) methanol-chloroform], followed by recrystallization from ethyl acetate-acetonitrile to afford Z-Gly-Gly-Gly-Glu(O$^t$Bu)-Thr($^t$Bu)-Thr($^t$Bu)-O$^{Bu}$ as crystals. The yield was 5.74 g (75.4%)

m.p. 167.5°–168.0° C. $[\alpha]_D^{25}$+7.28° (c=1.03 in DMF) Elemental Analysis for $C_{43}H_{70}N_6O_{13}$: Calcd.: C, 58.75; H, 8.03; N, 9.56 Found : C, 58.52; H, 7.78; N, 9.35

Amino acid analysis [6N HCl, 110° C., hydrolysis for 24 hours; values in parentheses show theoretical ones]: Glu 1.00(1); Thr 1.81(2); Gly 2.84(3)

Z-Gly-Gly-Gly-Glu(O$^t$Bu)-Thr($^t$Bu)-Thr($^t$Bu)-O$^t$Bu obtained above (1.97 g, 2.24 mmol) was dissolved in methanol (60 ml). To the solution was added 10% palladium-carbon (120 mg). The mixture was stirred for two hours in hydrogen streams at ordinary temperature under normal pressure. The catalyst was removed, then the solvent was distilled off to leave P-1 as a solid product. The yield was 1.64 g (98%).

FAB-MS (M+H)=879 (theoretical value=879)

Reference Example 2

Production of H-Gly-Gly-Gly-Glu (O$^t$BU)-Thr($^t$Bu)-O$^t$Bu (P-2)

a) H-Glu(O$^t$Bu)-Thr($^t$Bu)-O$^t$Bu (1.27 g, 3.05 mmol) and Z-Gly-Gly-Gly-OH (0.99 g, 3.05 mmol) were dissolved in DMF (20 ml). To the solution were added HOBT (453 mg, 3.35 mmol) and WSC (643 mg, 3.35 mmol). The mixture was stirred for 8 hours at 20° C. The reaction mixture was concentrated, which was suspended in 0.2M aqueous solution of citric acid (70 ml), followed by extraction with ethyl acetate (100 ml, 70 ml). The ethyl acetate layers were combined and washed with a 10% (w/v) aqueous solution of ammonium chloride, 5% (w/v) aqueous solution of sodium hydrogencarbonate, water and a saturated aqueous saline solution, successively, which was dried over anhydrous sodium sulfate, followed by concentration. To the concentrate was added ether-hexane. Resulting precipitates were collected by filtration to afford Z-Gly-Gly-Gly-Glu(O$^t$Bu)-Thr($^t$Bu)-O$^t$Bu (Z-P-2) as a while powdery product (1.87 g, 85%).

$[\alpha]_D^{23}$+6.9° (c=0.55 in chloroform) Elemental Analysis for $C_{35}H_{55}N_5O_{11}$: Calcd.: C, 58.24; H, 7.68; N, 9.70 Found : C, 57.87; H, 7.64; N, 9.97 b) This powdery product (1.09 g) was dissolved in methanol (36 ml), to which was added 10% palladium-carbon (109 ml). The mixture was stirred for two hours in hydrogen streams at ordinary temperature under normal pressure. The catalyst was removed, and the solvent was distilled off to leave P-2 as a powdery product (861 mg).

$[\alpha]_D^{23}$+9.1° (c=0.53 in chloroform) Elemental Analysis for $C_{27}H_{49}N_5O_9$: Calcd.: C, 55.18; H, 8.40; N, 11.92 Found: C, 54.88; H, 8.57; N, 11.68

Reference Example 3

Production of H-Glu(O$^t$Bu)-Gly-Glu(O$^t$Bu)-Gly-D-Glu-(O$^t$Bu)-O$^t$Bu (P-3)

In substantially the same manner as in Reference Example 2, H-Glu(O$^t$Bu)-Gly-Glu(O$^t$Bu)-Gly-D-Glu(O$^t$Bu)-O$^t$Bu (P-3) was produced

| | Materials | Reaction Conditions | Products |
|---|---|---|---|
| a) | 1) Z-Glu(O$^t$Bu)-OH (568 mg) | DCC HOBT OMF | 287 mg X-P-3 188 mg (550 mg) 25 ml |
| | 2) H—Gly—Glu(O$^t$Bu)-Gly-D-Glu(O$^t$Bu)-O$^t$Bu (710 mg) | 20° C. 16 h | |
| b) | Z-P-3 (550 mg) | 10% Pd—C MeOH 20° C. | 100 mg P-3 (470 mg) 18 ml 4 h |

Compound Z-P-3: $[\alpha]_D^{20}$+5.0° (C=0.54, in chloroform) 20 Elemental Analysis for $C_{43}H_{67}N_5O_{14}$: Calcd.: C, 58.82; H, 7.69; N, 7.98 Found : C, 58.67; H, 7.67; N, 8.26

Compound P-3: $[\alpha]_D^{20}$6.1 (C=0.51, in chloroform) Elemental Analysis for $C_{35}H_{61}N_5O_{12}$: Calcd.: C, 56.51; H, 8.27; N, 9.42 Found : C, 56.66; H, 8.30; N, 9.63

Reference Example 4

Production of H-Gly-Gly-Gly-Glu (O$^t$Bu)-O$^t$Bu (P-4)

In substantially the same manner as in Reference Example 2, H-Gly-Gly-Gly-Glu(O$^t$Bu)-O$^t$Bu (P-4) was produced.

| | Materials | Reaction Conditions | Products |
|---|---|---|---|
| a) | 1) Z-Gly—Gly—Gly—OH (0.84 g) | WSC HOBT DMF | 548 mg Z-P-4 386 mg (0.81 g) 15 ml |
| | 2) H—Glu(O$^t$Bu)-O$^t$Bu (0.68 g) | 20° C. 18 h | |
| b) | Z-P-4 (735 mg) | 10% Pd—C MeOH 20° C. | 73 mg P-4 (543 mg) 25 ml 2 h |

Compound Z-P-4: $[\alpha]_D^{23}$+9.6° (c=0.56, in chloroform) Elemental Analysis for $C_{27}H_{40}N_4O_9$: Calcd.: C, 57.43; H, 7.14; N, 9.92 Found : C, 57.60; H, 7.12; N, 9.88

Compound P-4: $[\alpha]_D^{23}$+13.1° (c=0.51, in chloroform) Elemental Analysis for $C_{19}H_{34}N_4O_7 \cdot 0.5H_2O$: Calcd.: C, 51.92; H, 8.03; N, 12.75 Found : C, 52.09; H, 7.89; N, 12.56

Reference Example 5

Production of H-Gly-Gly-Gly-D-Glu(O$^t$Bu)-O$^t$Bu (P-5)

In substantially the same manner as in Reference Example 2, H-Gly-Gly-Gly-D-Glu(O$^t$Bu)-O$^t$Bu (P-5) was produced.

| | Materials | Reaction Conditions | Products |
|---|---|---|---|
| a) | 1) Z-Gly—Gly—Gly—OH (1.62 g) | WSC HOBT DMF | 1.06 g Z-P-5 744 mg (1.93 g) 25 ml |
| | 2) H-D-Glu(O$^t$Bu)-O$^t$Bu (1.30 g) | 20° C. 16 h | |
| b) | Z-P-5 (1.92 g) | 10% Pd—C MeOH 20° C. | 192 mg P-5 (1.53 g) 64 ml 1.3 h |

Compound Z-P-5: $[\alpha]_D^{23}$−9.1° (c=0.54, in chloroform) Elemental Analysis for $C_{27}H_{40}N_4O_9$: Calcd.: C, 57.43; H, 7.14; N, 9.92 Found : C, 57.38; H, 7.06; N, 10.02

Compound P-5: $[\alpha]_D^{23}$−13.5° (c=0.54, in chloroform) Elemental Analysis for $C_{19}H_{34}N_4O_7 \cdot 0.5H_2O$ Calcd.: C, 51.92; H, 8.03; N, 12.75 Found : C, 51.98; H, 7.93; N, 12.68

Reference Example 6

Production of H-Glu(O$^t$Bu)-Gly-D-Glu(O$^t$Bu)-O$^t$Bu (P-6)

In substantially the same manner as in Reference Example 2, H-Glu(O$^t$Bu)-Gly-D-Glu(O$^t$Bu)-O$^t$Bu (P-6) was produced.

| | Materials | Reaction Conditions | Products |
|---|---|---|---|
| a) | 1) Fmoc-Glu(O$^t$Bu)-OH (2.78 g) | WSC HOBT DCM | 1.24 g Fmoc-P-6 876 mg (3.73 g) 85 ml |

2) H-Gly-D-Glu(O$^t$Bu)-O$^t$Bu 20° C. 16 h (1.86 g) $[\alpha]_D^{23}$−12° (C=0.54, in chloroform) Elemental Analysis for $C_{39}H_{53}N_3O_{10}$: Calcd.: C, 64.71; H, 7.38; N, 5.80 Found : C, 64.55; H, 7.43; N, 6.09 c) This powdery product (2.10 g) was dissolved in dichloromethane (63 ml), to which was added piperidine (7.0 ml), and the mixture was stirred for one hour at room temperatures. To the reaction mixture was added ethyl acetate (300 ml), which was subjected to extraction with 1N HCl (70 ml) and 0.03N HCl (100 ml× 2). The aqueous layer was adjusted to pH 6.0, which was washed with a mixture of hexane:ether (=1:1) (100 ml×5). Then, the pH was adjusted to 8.6, followed by extraction with ethyl acetate (150 ml×2). The extract was dried over anhydrous sodium sulfate, followed by concentration to afford P-6 as a colorless oily product (1.31 g).

$[\alpha]_D^{23}$ –17° (c=0.47, in chloroform) Elemental Analysis for $C_{24}H_{43}N_3O_8$: Calcd.: C, 57.47; H, 8.64; N, 8.38 Found : C, 57.40; H, 8.73; N, 8.60

Reference Example 7

Production of H-Gly-Gly-Glu(O$^t$Bu)-O$^t$Bu (P-7)

In substantially the same manner as in Reference Example 2, H-Gly-Gly-Glu (O$^t$Bu)-O$^t$Bu (P-7) was produced.

| | Materials | Reaction Conditions | Products |
|---|---|---|---|
| a) | 1) Z-Gly—Gly—OH (2.05 g) | WSC 1.63 g<br>HOBT 1.15 g<br>DMF 40 ml | Z-P-7 (3.34 g) |
| | 2) H—Glu(O$^t$Bu)-O$^t$Bu (2.00 g) | 20° C.<br>17 h | |
| b) | Z-P-7 (2.00 g) | 10% Pd—C<br>MeOH 60 ml<br>20° C. 3 h | 200 mg P-7 (colorless oily product) (1.45 g) |

Compound Z-P-7: Elemental Analysis for $C_{25}H_{37}N_3O_8 \cdot 0.5H_2O$ Calcd.: C, 58.13; H, 7.41; N, 8.13 Found : C, 58.44; H, 7.37; N, 8.33

Reference Example 8

Production of H-Gly-Gly-Gly-Asp(O$^t$Bu)-O$^t$Bu (P-8)

In substantially the same manner as in Reference Example 2, H-Gly-Gly-Gly-Asp(O$^t$Bu)-O$^t$Bu (P-8) was produced.

| | Materials | Reaction Conditions | Products |
|---|---|---|---|
| a) | 1) Z-Gly—Gly—Gly—OH (6.67 g) | WSC 3.44 g<br>HOBT 2.42 g<br>DMF 100 ml | Z-P-8 (8.30 g) |
| | 2) H—Asp(O$^t$Bu)-O$^t$Bu (4.00 g) | 20° C.<br>15 h | |
| b) | Z-P-8 (1.87 g) | 10% Pd—C<br>MeOH 60 ml<br>20° C. 2 h | 187 mg P-8 (1.35 g) |

Compound z-P-8: Elemental Analysis for $C_{39}H_{38}N_4O_9$: Calcd.: C, 56.72; H, 6.96; N, 10.18 Found : C, 56.48; H, 6.88; N, 10.23

Compound P-8: Elemental Analysis for $C_{18}H_{32}N_4O_7$: Calcd.: C, 51.91; H, 7.74; N, 13.45 Found : C, 51.80; H, 8.11; N, 13.50

Reference Example 9

Production of H-Gly-Gly-D-Glu(O$^t$Bu)-O$^t$Bu (P-9)

In substantially the same manner as in Reference Example 2, H-Gly-Gly-D-Glu(O$^t$Bu)-O$^t$Bu (P-9) was produced.

| | Materials | Reaction Conditions | Products |
|---|---|---|---|
| a) | 1) Z-Gly—Gly—OH (790 mg) | WSC 569 mg<br>HOBT 401 mg<br>DMF 23 ml | Z-P-9 (1.18 g) |
| | 2) H-D-Glu(O$^t$Bu)-O$^t$Bu (700 mg) | 20° C.<br>16 h | |
| b) | Z-P-9 (1.10 g) | 10% Pd—C<br>MeOH 40 ml | 110 mg P-9 (850 mg) |

Compound Z-P-9: $[\alpha]_D^{24}$ –9.3° (c=0.53, in chloroform) Elemental Analysis for $C_{25}H_{37}N_3O_8 \cdot 0.5H_2O$: Calcd.: C, 58.13; H, 7.41; N, 8.13 Found : C, 58.31, H, 7.42; N, 8.24

Compound P-9: $[\alpha]_D^{23}$ –11.9° (c=0.37, in chloroform) Elemental Analysis for $C_{17}H_{31}N_3O_6 \cdot 0.25H_2O$: Calcd.: C, 54.02; H, 8.40; N, 11.12 Found : C, 53.84, H, 8.58; N, 11.24

Reference Example 10

Production of H-Gly-D-Glu(O$^t$Bu)-O$^t$Bu (P-10)

In substantially the same manner as in Reference Example 2, H-Gly-D-Glu(O$^t$Bu)-O$^t$Bu (P-10) was produced.

| | Materials | Reaction Conditions | Products |
|---|---|---|---|
| a) | 1) Z-Gly—OH (620 mg) | WSC 569 mg<br>HOBT 401 mg<br>DCM 23 ml | Z-P-10 (1.23 g) |
| | 2) H-D-Glu(O$^t$Bu)-O$^t$Bu (700 mg) | 20° C.<br>16 h | |
| b) | Z-P-10 (1.23 g) | 10% Pd—C<br>MeOH 40 ml<br>20° C. 1.5 h | 120 mg P-10 (830 mg) |

Compound Z-P-10: $[\alpha]_D^{20}$ – 10.3° (C=0.52, in chloroform) Elemental Analysis for $C_{23}H_{34}N_2O_7 \cdot 0.25H_2O$: Calcd.: C, 60.71; H, 7.64; N, 6.16 Found : C, 60.79, H, 7.68; N, 6.28

Compound P-10: $[\alpha]_D^{20}$ – 17.9° (C=0.52, in chloroform) Elemental Analysis for $C_{15}H_{28}N_2O_5$: Calcd.: C, 56.94; H, 8.92; N, 8.85 Found : C, 56.81, H, 8.95; N, 9.04

Reference Example 11

Production of H-Gly-Glu(O$^t$Bu)-Glu(O$^t$Bu)-O$^t$Bu (P-11)

In substantially the same manner as in Reference Example 2, H-Gly-Glu(O$^t$Bu)-Glu(O$^t$Bu)-O$^t$Bu (P-11) was produced.

| | Materials | Reaction Conditions | Products |
|---|---|---|---|
| a) | 1) Z-Gly—OH (347 mg) | WSC 318 mg<br>HOBT 224 mg<br>DCM 22 ml | Z-P-11 (930 mg) |
| | 2) H—Glu(O$^t$Bu)-Glu(O$^t$Bu)-O$^t$Bu (670 mg) | 20° C.<br>16 h | |
| b) | Z-P-11 (870 mg) | 10% Pd—C<br>MeOH 30 ml<br>20° C. 2 h | 90 mg P-11 (650 mg) |

Compound Z-P-11: m.p. 92.4°–92.7° C. $[\alpha]_D^{24}$ –3.5° (C=0.51, in chloroform) Elemental Analysis for $C_{32}H_{49}N_3O_{10} \cdot 0.25H_2O$: Calcd.: C, 60.03; H, 7.79; N, 6.56 Found : C, 60.18, H, 7.81; N, 6.26

Compound P-11: $[\alpha]_D^{24}$ – 6.8° (C=0.54, in chloroform) Elemental Analysis for $C_{24}H_{43}N_3O_8 \cdot 0.25H_2O$: Calcd.: C, 56.95; H, 8.66; N, 8.30 Found : C, 56.92, H, 8.74; N, 8.06

Reference Example 12

Production of H-Gly-Glu(O$^t$Bu)-D-Glu(O$^t$Bu)-O$^t$Bu (P- 12)

In substantially the same manner as in Reference Example 2, H-Gly-Glu(O$^t$Bu)-D-Glu(O$^t$Bu)-O$^t$Bu (P-12) was produced.

| | Materials | Reaction Conditions | Products |
|---|---|---|---|
| a) | 1) Z-Gly—OH | WSC | 334 mg Z-P-12 |

-continued

| Materials | Reaction Conditions | Products |
|---|---|---|
| (364 mg) | HOBT 235 mg<br>DCM 23 ml<br>20° C. 16 h | (760 mg) |
| 2) H—Glu(O$^t$Bu)-D-Glu(O$^t$Bu)-O$^t$Bu<br>(700 mg) | | |
| b) Z-P-12<br>(700 mg) | 10% Pd—C 70 mg<br>MeOH 23 ml<br>20° C. 2 h | P-12<br>(550 mg) |

Compound Z-P 12: $[\alpha]_D^{23}$ −11.5° (C=0.53, in chloroform) Elemental Analysis for $C_{32}H_{49}N_3O_{10}$: Calcd.: C, 60.46; H, 7.77; N, 6.61 Found : C, 60.47, H, 7.88; N, 6.53

Compound P-12: $[\alpha]_D^{23}$ −19.8° (C=0.51, in chloroform) Elemental Analysis for $C_{24}H_{43}N_3O_8 \cdot 0.5H_2O$: Calcd.: C, 56.45; H, 8.69; N, 8.23 Found : C, 56.52, H, 8.77; N, 8.25

Reference Example 13

Production of H-Glu(O$^t$Bu)-Gly-Glu(O$^t$Bu)-O$^t$Bu (P-13)

In substantially the same manner as in Reference Example 2, H-Glu(O$^t$Bu)-Gly-Glu(O$^t$Bu)-O$^t$Bu (P-13) was produced.

| Materials | Reaction Conditions | Products |
|---|---|---|
| a) 1) Z-Glu(O$^t$Bu)-OH<br>(785 mg) | WSC 447 mg<br>HOBT 315 mg<br>DCM 22 ml<br>20° C. 16 h | Z-P-13<br>(1.20 g) |
| 2) H—Gly—Glu(O$^t$Bu)-O$^t$Bu<br>(670 mg) | | |
| b) Z-P-13<br>(1.10 g) | 10% Pd—C 110 mg<br>MeOH 40 ml<br>20° C. 2 h | P-13<br>(840 mg) |

Compound Z-P-13: $[\alpha]_D^{24}$ +4.2° (C=0.53, in chloroform) Elemental Analysis for $C_{32}H_{49}N_3O_{10}$: Calcd.: C, 60.46; H, 7.77; N, 6.61 Found : C, 60.48, H, 7.78; N, 6.88

Compound P-13: $[\alpha]_D^{24}$ +7.0° (C=0.52, in chloroform) Elemental Analysis for $C_{24}H_{43}N_3O_8 \cdot 0.25H_2O$: Calcd.: C, 56.95; H, 8.66; N, 8.30 Found : C, 56.94, H, 8.60; N, 8.04

Reference Example 14

Production of H-Glu(O$^t$Bu)-D-Glu(O$^t$Bu)-O$^t$Bu (P-14)

In substantially the same manner as in Reference Example 2, H-Glu(O$^t$Bu)-D-Glu(O$^t$Bu)-O$^t$Bu (P-14) was produced.

| Materials | Reaction Conditions | Products |
|---|---|---|
| a) 1) Z-Glu(O$^t$Bu)-OH<br>(1.86 g) | WSC 1.06 g<br>HOBT 746 mg<br>DCM 43 ml<br>20° C. 16 h | Z-P-14<br>(3.09 g) |
| 2) H-D-Glu(O$^t$Bu)-O$^t$Bu<br>(1.30 g) | | |
| b) Z-P-14<br>(3.00 g) | 10% Pd—C 500 mg<br>MeOH 67 ml<br>20° C. 3 h | P-14<br>(2.24 g) |

Compound Z-P-14: $[\alpha]_D^{23}$ −7.9° (c=0.56, in chloroform) Elemental Analysis for $C_{30}H_{46}N_2O_9$: Calcd.: C, 62.27; H, 8.01; N, 4.84 Found: C, 62.49, H, 8.14; N, 5.07

Compound P-14: $[\alpha]_D^{23}$ +2.3° (c=0.61, in chloroform) Elemental Analysis for $C_{22}H_{40}N_2O_7 \cdot 1.5H_2O$: Calcd.: C, 56.03; H, 9.19; N, 5.94 Found: C, 56.04, H, 8.96; N, 5.92

Reference Example 15

Production of H-Glu(O$^t$Bu)-Glu(O$^t$Bu)-Glu(O$^t$Bu)-O$^t$Bu (P-15)

In substantially the same manner as in Reference Example 2, H-Glu(O$^t$Bu)-Glu(O$^t$Bu)-Glu(O$^t$Bu)-O$^t$Bu (P-15) was produced.

| Materials | Reaction Conditions | Products |
|---|---|---|
| a) 1) Z-Glu(O$^t$Bu)-OH<br>(559 mg) | WSC 318 mg<br>HOBT 224 mg<br>DCM 22 ml<br>20° C. 16 h | Z-P-15<br>(1.06 g) |
| 2) H-Glu(O$^t$Bu)-Glu(O$^t$Bu)-O$^t$Bu<br>(670 mg) | | |
| b) Z-P-15<br>(1.00 g) | 10% Pd—C 100 mg<br>MeOH 33 ml<br>20° C. 2 h | P-15<br>(800 mg) |

Compound Z-P-15: $[\alpha]_D^{24}$ −11.7° (C=0.53, in chloroform) Elemental Analysis for $C_{39}H_{61}N_3O_{12}$: Calcd.: C, 61.32; H, 8.05; N, 5.50 Found : C, 61.40, H, 8.13; N, 5.28

Compound Z-15: $[\alpha]_D^{24}$ −13.9° (C=0.49, in chloroform) Elemental Analysis for $C_{31}H_{55}N_3O_{10}$: Calcd.: C, 59.12; H, 8.80; N, 6.67 Found : C, 58.96, H, 8.91; N, 6.80

Reference Example 16

Production of H-Glu(O$^t$Bu)-Glu(O$^t$Bu)-D-Glu(O$^t$Bu)-O$^t$Bu (P-16)

In substantially the same manner as in Reference Example 2, H-Glu(O$^t$Bu)-Glu(O$^t$Bu)-D-Glu(O$^t$Bu)-O$^t$Bu (P-16) was produced.

| Materials | Reaction Conditions | Products |
|---|---|---|
| a) 1) Z-Glu(O$^t$Bu)-OH<br>(586 mg) | WSC 334 mg<br>HOBT 235 mg<br>DCM 23 ml<br>20° C. 16 h | Z-P-16<br>(880 mg) |
| 2) H-Glu(O$^t$Bu)-D-Glu(O$^t$Bu)-O$^t$Bu<br>(700 mg) | | |
| b) Z-P-16<br>(800 mg) | 10% Pd—C 80 mg<br>MeOH 27 ml<br>20° C. 2 h | P-16<br>(640 mg) |

Compound Z-P-16: $[\alpha]_D^{24}$ −20.6° (C=0.52, in chloroform) Elemental Analysis for $C_{39}H_{61}N_3O_{12}$: Calcd.: C, 61.32; H, 8.05; N, 5.50 Found : C, 61.20, H, 8.26; N, 5.31

Compound P-16: $[\alpha]_D^{24}$ −25.5° (c=0.54, in chloroform) Elemental Analysis for $C_{31}H_{55}N_3O_{10} \cdot 0.25H_2O$: Calcd.: C, 58.70; H, 8.82; N, 6.63 Found : C, 58.76, H, 8.91; N, 6.45

Reference Example 17

Production of $NH_2(CH_2)_7CO$-Glu(O$^t$Bu)-O$^t$Bu (P-17)

a) To a solution of 8-(benzyloxycarbonylamino)octanoic acid (1.55 g) and H-Glu(O$^t$Bu)-O$^t$Bu hydrochloride (1.88 g) in DMF (50 ml) were added TEA (1.76 ml) and DEPC (1.29 g), and the mixture was stirred for 24 hours at 20° C. To the reaction mixture was added water, which was subjected to extraction with ethyl acetate. The extract was washed with a 5% (w/v, hereinafter in the same way) aqueous solution of citric acid, a saturated aqueous solution of sodium hydrogencarbonate and a saturated aqueous saline solution, which was dried over anhydrous sodium sulfate. The solvent was distilled off, and the residue was purified by means of a silica gel column chromatography (hexane:ethyl acetate=2:1) to give Z-NH(CH$_2$)$_7$CO-Glu(O$^t$Bu)-O$^t$Bu (Z-P-17) (2.40 g. yield 85%) as a colorless oily product.

IR (neat) ν: 3310, 1720, 1650 cm$^{-1}$ $^1$H-NMR (CDCl$_3$) δ1.10–1.37 (8H,m), 1.44 (9H,s), 1.47 (9H,s), 1.48–2.43 (8H,m), 3.18 (2H,q,J=6.6 Hz), 4.41–4.54 (1H,m), 4.70–4.88 (1H,m), 5.10 (2H,s), 6.15 (1H,d,J=8.0 Hz), 7.27–7.37 (5H, m)

b) To a solution of the compound Z-P-17 (1.19 g) obtained as above in ethanol (20 ml) was added 10% palladium-carbon (100 mg). The mixture was stirred for 2 hours at 20° C. in hydrogen streams. The reaction mixture was subjected to filtration to obtain P-17 (739 mg, yield 83%) as a colorless oily product.

IR (neat) ν: 3280, 1720, 1660 cm$^{-1}$ $^1$H-NMR (CDCl$_3$) δ: 1.20–1.40 (6H,m), 1.44 (9H,s), 1.47 (9H,s), 1.52–2.38 (10H, m), 2.38–2.65 (2H,m), 2.73 (2H,t,J=7.0 Hz), 4.42–4.55 (1H,m), 6.21 (1H,d,J=8.2 Hz)

Reference Example 18

Production of NH$_2$(CH$_2$)$_{11}$CO-Glu(O$^t$Bu)-O$^t$Bu (P-18)

In substantially the same manner as in Reference Example 17, NH$_2$(CH$_2$)$_{11}$CO-Glu(O$^t$Bu)-O$^t$Bu (P-18) was synthesized.

|   | Materials | Reaction Conditions | | Products |
|---|---|---|---|---|
| a) | 1) Z-NH(CH$_2$)$_{11}$COOH (3.49 g) | DEPC TEAT DMF | 2.45 g 3.5 ml 100 ml | Z-P-18 (2.32 g) |
|   | 2) H-Glu(O$^t$Bu)-O$^t$Bu.HCl (2.96 g) | 20° C. | 24 h | |
| b) | Z-P-18 (2.31 g) | 10% Pd/C EtOH 20° C. | 230 mg 50 ml 2 h | P-18 (1.78 g) |

Compound Z-P-18: IR (neat) ν: 3310, 1725, 1650 cm$^{-1}$ $^1$H-NMR (CDCl$_3$) δ: 1.10–1.41 (16H,m), 1.44 (9H,s), 1.47 (9H,s), 1.41–2.44 (8H,m), 3.19 (2H,dt,J=7.0, 7.0 Hz), 4.42–4.56 (1H,m), 5.10 (2H,s), 6.13 (1H,d,J=7.6 Hz), 7.23–7.40 (5H,m)

Compound P-18: IR (neat) ν: 3280, 1730, 1650 cm$^{-1}$ $^1$H-NMR (CDCl$_3$) δ: 1.05–1.40 (16H,m), 1.44 (9H,s), 1.47 (9H,s), 1.55–1.72 (4H,m), 1.72–2.50 (10H,m), 2.68. (2H,t, J=7.0 Hz), 3.19 (2H,t,J=7.6 Hz), 4.43–4.57 (1H,m), 6.14 (1H,d,J=7.8 Hz)

Reference Example 19

Production of 4-aminobenzoyl-Glu(O$^t$Bu)-O$^t$Bu (P-19)

To a solution of 4-aminobenzoic acid (6.86 g) and H-Glu-(O$^t$Bu)-O$^t$Bu hydrochloride (14.8 g) in DMF (200 ml) were added TEA (17 ml) and DEPC (12.2 g). The mixture was stirred for 48 hours at 20° C. To the reaction mixture was added water, which was subjected to extraction with ethyl acetate. The extract was washed with a 5% aqueous solution of citric acid, a saturated aqueous solution of sodium hydrogencarbonate and a saturated aqueous saline solution, followed by drying over anhydrous sodium sulfate. The solvent was distilled off, and the residue was washed with ether to give the compound P-19 (16.2 g, yield 86%) as a white powdery product.

IR (KBr) ν: 3450, 3390, 3370, 1715, 1625, 1610 cm$^{-1}$ $^1$H-NMR (CDCl$_3$) δ: 1.42 (9H,s), 1.49 (9H,s), 1.90–2.53 (4H,m), 3.99 (2H,br s), 4.60–4.73 (1H,m), 6.61–6.72 (2H, m), 6.76 (1H,d,J=7.6 Hz), 7.60–7.71 (2H,m)

Reference Example 20

Production of 4-(glycylamino)benzoyl-Glu(O$^t$Bu)-O$^t$Bu (P-20)

a) To a solution of the compound P-19 (568 mg) obtained in Reference Example 19 in pyridine (2 ml) was added phosphorus trichloride (0.087 ml), and the mixture was stirred for 2 hours at room temperature. To the mixture was further added Z-glycine (209 mg), which was stirred for 18 hours at 20° C. To the reaction mixture was added water, which was subjected to extraction with ethyl acetate, followed by drying over anhydrous sodium sulfate. The solvent was distilled off, and the residue was purified by means of a silica gel column chromatography (hexane: ethyl acetate= 1:1) to give the compound Z-P-20 (414 mg, yield 73%) as a white powdery product.

IR (KBr) ν: 3310, 1700, 1640, 1600 cm$^{-1}$ $^1$H-NMR (CDCl$_3$) δ: 1.42 (9H,s), 1.49 (9H,s), 1.95–2.55 (4H,m), 4.02 (2H,d,J=5.8 Hz), 4.59–4.72 (1H,m), 5.17 (2H,s), 5.59–5.75 (1H,m), 7.09 (1H,d,J=7.8 Hz), 7.30– 7.42 (5H,m), 7.53 (2H,d,J=8.0 Hz), 7.77 (2H,d,J=8.0 Hz), 8.30–8.50 (1H,m)

b) To a solution of the compound Z-P-20 (414 mg) in ethanol (4 ml) was added 10% palladium-carbon (40 mg). The mixture was stirred for 2 hours at 20° C. in hydrogen streams. The reaction mixture was subjected to filtration to give the compound P-20 (296 mg, yield 94%) as a white powdery product.

IR (KBr) ν: 3425, 3400, 1740, 1720, 1680, 1640, 1610 cm$^{-1}$ $^1$H-NMR (CDCl$_3$) δ: 1.41 (9H,s), 1.48 (9H,s), 1.90–2.55 (4H,m), 3.59 (2H,br s), 4.58–4.72 (1H,m), 7.02–7.15 (1H,m), 7.65 (2H,d,J=8.8 Hz), 7.77 (2H,d,J=8.8 Hz), 9.65–9.77 (1H,m)

Reference Example 21

Production of NH$_2$(CH$_2$)$_5$CO-Glu(O$^t$Bu)-O$^t$Bu (P-21)

In substantially the same procedure as in Reference Example 17, NH$_2$(CH$_2$)$_5$CO-Glu(O$^t$Bu)-O$^t$Bu (P-21) was synthesized.

|   | Materials | Reaction Conditions | | Products |
|---|---|---|---|---|
| a) | 1) Z-NH(CH$_2$)$_5$COOH (2.92 g) | DEPC TEA DMF | 2.45 g 4.9 ml 50 ml | Z-P-21 (5.30 g) |
|   | 2) H-Glu(O$^t$Bu)-O$^t$Bu.HCl (2.95 g) | 0° C. | 30 min | |
| b) | Z-P-21 (5.30 g) | 10% Pd/C MeOH 20° C. | 0.5 g 100 ml 2 h | P-21 (3.89 g) |

Compound P-21: $^1$H-NMR (CDCl$_3$) δ: 1.389 (2H,m), 1.444 (9H,s), 1.50–1.75 (4H,m), 1.75–2.15 (2H,m), 2.15–2.38 (4H,m), 2,796 (2H,t,J=6.6 Hz), 3,320 (2H,bs), 4,460 (1H,m), 6.400 (1H,d,J=7.4 Hz) IR (neat) ν: 3270, 3040, 2970, 2920, 2855, 1725, 1645. 1540, 1470, 1450, 1390, 1360, 1320, 1290, 1250, 1220, 1150 cm$^{-1}$ Reference Example 22

Production of NH$_2$(CH$_2$)$_6$NHCO-Glu(O$^t$Bu)-O$^t$Bu (P-22)

a) Hexamethylenediamine (2.32 g, 20 mmol) was dissolved in methanol (20 ml). To the solution were added a 1N aqueous solution of sodium hydroxide (22 ml) and a solution of carbobenzoxy chloride (3.4 g, 20 mmol) in THF (20 ml) simultaneously. The mixture was stirred for one hour at 20° C. The reaction mixture was concentrated to dryness, and the concentrate was dissolved in chloroform (100 ml). The solution was washed with water and a saturated aqueous saline solution. The organic layer was dried over anhydrous sodium sulfate, which was concentrated to dryness under reduced pressure. The concentrate was allowed to be adsorbed on a silica gel column (20 g) processed with ammonia. Elution was then conducted with chloroform-methanol-water (65:25:4) to give a colorless oily product. This product was dissolved in TEA (1.34 ml, 9.64 mmol) and DCM (10 ml). To the solution was added, under ice-cooling, 4-nitrophenyl chloroformate (971 mg, 4.82 mmol), and the mixture was stirred for one hour. To the reaction mixture was added chloroform (20 ml), which was washed with water and a saturated aqueous saline solution. The organic layer was dried over anhydrous sodium sulfate, which was concentrated to dryness under reduced pressure. The concentrate was washed with ethyl ether to give 6-benzyloxy-carbonylamino-1-(p-nitrophenyloxycarbonyl)aminohexane as colorless crystals (1.16 g, yield 14.5%)

$^1$H-NMR (CDCl$_3$) δ: 1.25–2.70 (8H,m), 3.225 (4H,m), 4.742 (1H,br s), 5.099 (2H,s), 5.25 (1H,br s), 7.284 (2H,d, J=9.0 Hz), 8.237 (2H,d,J=9.0 Hz)

b) The compound obtained as above (1.16 g, 2.79 mmol) and H-Glu(O$^t$Bu)-O$^t$Bu hydrochloride (825 mg, 2.79 mmol) were dissolved DCM (10 ml). To the solution were added DMAP (680 mg, 5.58 mmol) and TEA (0.77 ml, 5.58 mmol), and the mixture was stirred for 2 hours at 20° C. To the reaction mixture was added chloroform (20 ml). The mixture was washed with water at pH 3.5, followed by washing with a saturated aqueous solution of sodium hydrogencarbonate. The organic layer was dried over anhydrous sodium sulfate, which was concentrated under reduced pressure. The concentrate was purified by means of a silica gel column [20 g, ethyl acetate-n-hexane (2:3)] to give Z-NH(CH$_2$)$_6$NHCO-Glu(O$^t$Bu)-O$^t$Bu (Z-P- 22) as a white solid product (1.50 g, yield 100%). $^1$H-NMR (CDCl$_3$) δ: 1.20–1.38(8H,m), 1.436 (9H,s), 1.453 (9H,s), 1.70–2.22 (2H,m), 2.326 (2H,m), 3.169 (4H,m), 4.340 (1H,m), 4.626 (1H,br s), 4.869 (1H,br s), 5.045 (1H,d,J=7.6 Hz), 5.103 (2H,s), 7.352 (5H,s) IR (neat) ν: 3350, 2980, 2940, 2855, 1730, 1640, 1560, 1455, 1395, 1370, 1330, 1255, 1150, 1100, 1030, 850, 750, 735, 700 cm$^{-1}$ c) 10% Palladium-carbon (250 mg) was suspended in methanol (20 ml). The suspension was stirred for 30 minutes in hydrogen streams, to which was added the compound Z-P-22 (1.50 g, 2.79 mmol), followed by stirring for 1.5 hour at 20° C. in hydrogen streams. From the reaction mixture was removed insolubles by filtration. The filtrate was concentrated to dryness under reduced pressure to give P-22 as a colorless solid product (1.12 g, yield 100%).

$^1$H-NMR (CDCl$_3$) δ: 1.391 (10H,m), 1,431 (9H,s), 1.451 (9H,s), 1.747 (2H,m), 1.60–2.15 (2H,m), 2.90–3.20 (4H,m), 4.321 (1H,m), 6.013 (2H,m) IR (neat) ν: 3350, 2980, 2930, 2860, 1730, 1640, 1560, 1500, 1475, 1455, 1390, 1365, 1250, 1150 cm$^{-1}$ Reference Example 23

Production of 4-(aminomethyl)benzoyl-Glu(O$^t$Bu)-O$^t$Bu hydrochloride (P-23)

a) To a solution of 4-(aminomethyl)benzoic acid (25 g) in a 2N aqueous solution of sodium hydroxide (100 ml) was added dropwise, under ice-cooling, a solution of benzyloxycarbonyl chloride (33.8 g) in THF (50 ml), and the mixture was stirred for 2 hours. Resultant precipitate was collected by filtration, which was washed with water, 1N HCl and ether, followed by drying under reduced pressure to give 4-(Z-aminomethyl)benzoic acid as a white powdery product (10.5 g, yield 22%).

IR (neat) ν: 3313, 1684, 1612, 1529, 1430, 1322, 1292, 1253, 1054, 761, 696 cm$^{-1}$ $^1$H-NMR (CDCl$_3$) δ: 4.26 (2H,d,J=6.2 Hz), 5.05 (2H,s), 7.31 (2H,d,J=8.0 Hz), 7.36 (5H,s), 7.87 (2H,d,J=8.0 Hz)

b) To a solution of 4-(Z-aminomethyl)benzoic acid (1.0 g) synthesized as above, H-Glu(O$^t$Bu)-O$^t$Bu hydrochloride (1.15 g) and DEPC (860 mg) in DMF (20 ml) was added dropwise TEA (1.06 g). The mixture was stirred for one hour at 20° C. The solvent was distilled off under reduced pressure, and the residue was purified by means of a silica gel column (n-hexane:ethyl acetate=2:1) to give 4-(Z-aminomethyl)benzoyl-Glu(O$^t$Bu)-O$^t$Bu (1.86 g, yield 100%) as a colorless waxy product.

IR (neat) ν: 1720, 1700, 1640, 1530, 1500, 1360, 1250, 1145 cm$^{-1}$ $^1$H-NMR (CDCl$_3$) δ: 1.42 (9H,s), 1.49 (9H,s), 1.90–2.55 (4H,m), 4.43 (2H,d,J=6.0 Hz), 4.66 (1H,m), 5.15 (3H,s), 7.01 (1H,d,J=7.0 Hz), 7.30–7.40 (7H,m), 7.79 (2H, d,J=8.4 Hz)

c) A suspension of the compound obtained as above (1.85 g) and 10% palladium-carbon (200 mg) in methanol (13 ml) was subjected to catalytic reduction to consume hydrogen (80 ml). The catalyst was filtered off, and to the filtrate was added a 4N HCl ethyl acetate solution (0.88 ml). The solution was concentrated to give 4-(aminomethyl)benzoyl-Glu(O$^t$Bu)-O$^t$Bu hydrochloride (P-23) as an amorphous product.

IR (neat) ν: 3400, 3000, 1731, 1650, 1540, 1506, 1369, 1235, 1151 cm$^{-1}$ $^1$H-NMR (CDCl$_3$) δ: 1.41 (9H,s), 1.48 (9H,s), 1.90–2.40 (4H,m), 4.13 (2H,s), 4.59 (1H,m), 7.48 (2H,d,J=8.0 Hz), 7.69 (3H,d,J=8.0 Hz)

Reference Example 24

Production of 4-(N-(t-butyloxycarbonylmethyl)-aminomethyl)benzoyl-Glu (O$^t$Bu)-O$^t$Bu (P-24)

a) To a solution of methyl terephthalaldehydate (3.0 g), H-Gly-O$^t$Bu hydrochloride (3.0 g), TEA (1.81 g), and acetic acid (1.08 g) was added, under ice-cooling, sodium cyanoborohydride (1.15 g), and the mixture was stirred for one hour at 20° C. The reaction mixture was concentrated, which was dissolved in ethyl acetate. The solution was washed with a saturated aqueous solution of sodium hydrogencarbonate, followed by drying. The resultant mixture was concentrated, and the concentrate was purified by means of a silica gel column (n-hexane:ethyl acetate=9:1–5:1) to give methyl 4-(N-t-butyloxycarbonylmethyl)aminomethyl)benzoate (1.98 g, yield 39%).

IR (neat) ν: 2975, 1720, 1605, 1455, 1430, 1410, 1390, 1360, 1280, 1225, 1150, 1100 cm$^{-1}$ $^1$H-NMR (CDCl$_3$) δ: 1.47 (9H,s), 3.30 (2H,s), 3.85 (2H,s), 3.91 (3H,s), 7.41 (2H,d,J=8.4 Hz), 8.00 (2H,d,J=8.4 Hz)

b) To a solution of the compound synthesized as above (1.03 g) and TEA (445 mg) in DCM (20 ml) was added dropwise, under ice-cooling, benzyloxycarbonyl chloride (690 mg). The mixture was stirred for 2 hours. The solvent was distilled off under reduced pressure. The residue was dissolved in a mixture of THF (6 ml)-MeOH(10 ml)-H$_2$O (1 ml). To the solution was added LiOH.H$_2$O (400 mg), and the mixture was stirred for 4 hours at 20° C. The solvent was distilled off under reduced pressure. The residue was made acidic with a 5% aqueous solution of KHSO$_4$, followed by extraction with chloroform. The extract solution was dried, then the solvent was distilled off under reduced pressure. The residue was purified by means of a silica gel column (n-hexane:ethyl acetate=1:1) to give 4-(N-benzyloxycarbonyl-N-(t-butyloxycarbonylmethyl) aminomethyl)benzoic acid (337 mg, yield 23%).

IR (neat) ν: 1735, 1705, 1700, 1450, 1410, 1360, 1290, 1230, 1220, 1150 cm$^{-1}$ $^1$H-NMR (CDCl$_3$) δ: 1.37 (1/2×9H,s), 1.45 (1/2×9H,s), 3.81 (1/2×2H,s), 3.92 (1/2×2H,s), 4.60–4.75 (2H,m), 5.20 (2H,s), 7.25–7.45 (7H,m), 8.05 (1/2×2H,d,J=8.0 Hz), 8.08 (1/2×2H,d,J=8.0 Hz)

c) A solution of the compound obtained as above (335 mg), H-Glu(O$^t$Bu)-O$^t$Bu hydrochloride (273 mg), DEPC (205 mg) and TEA (255 mg) in DMF (8 ml) was stirred for one hour at 20° C. The solvent was distilled off under reduced pressure, and the residue was purified by means of a silica gel column (n-hexane:ethyl acetate=4:1) to give 4-(N-benzyloxycarbonyl-N-(t-butyloxycarbonylmethyl) aminomethyl)benzoyl-Glu(O$^t$Bu-O$^t$Bu (504 mg, yield 94%).

IR (neat) ν: 3350, 2970, 1730, 1710, 1660, 1530, 1495, 1450, 1360, 1240, 1220, 1150 cm$^{-1}$ $^1$H-NMR (CDCl$_3$) δ: 1.37 (1/2×9H,s), 1.42 (9H,s), 1.45 (1/2×9H,s), 1.50 (9H,s), 1.95–2.50 (4H,m), 3.77 (1/2×2H,s), 3.88 (1/2×2H,s), 4.60–4.75 (3H,m), 5.20 (2H,s), 7.02 (1H,d ,J=7.4 Hz ), 7.20–7.40 (7H,m), 7.77 (1/2×2H,d,J=8.0 Hz) , 7.80 (1/2× 2H,d,J=8.0 Hz)

d) A solution of the compound obtained as above (500 mg) and 10% Pd—C (200 mg) in MeOH (8 ml) was subjected to catalytic reduction to allow 20 ml of hydrogen to be consumed. The catalyst was removed, then the solvent was distilled off under reduced pressure. The residue was pulverized from n-hexane-ethyl acetate (3:1) to give the compound P-24 (265 mg, yield 67%) as a white powdery product.

IR (neat) ν: 3400, 2970, 1730, 1650, 1535, 1525, 1360, 1245, 1150 cm$^{-1}$ $^1$H-NMR (CDCl$_3$) δ: 1.43 (9H,s), 1.47 (9H,s), 1.49 (9H,s), 1.90–2.50 (4H,m), 3.53 (2H,s), 4.41 (2H,s), 4.65 (1H,m), 7.18 (1H,d,J=7.2 Hz), 7.70 (2H,d,J=8.0 Hz), 7.88 (2H,d,J=8.0 Hz)

Reference Example 25

Production of H-Gly-Lys(Boc)-Gly-O$^t$Bu (P-25)

In substantially the same manner as in Reference Example 2, H-Gly-Lys(Boc)-Gly-O$^t$Bu (P-25) was produced.

| | Materials | Reaction Conditions | | Products |
|---|---|---|---|---|
| a) | 1) Z-Gly-OH (813 mg) | WSC HOBT DMF | 745 mg 525 mg 20 ml | Z-P-25 (1.90 g) |
| | 2) H-Lys(Boc)-Gly-O$^t$Bu (1.27 g) | 20° C. | 13 h | |
| b) | Z-P-25 (1.54 g) | 10% Pd/C MeOH 20° C. | 154 mg 40 ml 5 h | P-25 (1.15 g) |

Compound Z-P-25: $[α]_D^{24}$ –13.4° (C=0.58, in chloroform) Elemental Analysis for C$_{27}$H$_{42}$N$_4$O$_8$.0.5H$_2$O: Calcd.: C, 57.95; H, 7.74; N, 10.01 Found : C, 57.73, H, 7.44; N, 10.03

Compound P-25: $[α]_D^{24}$ –23.8° (C=0.58, in chloroform) Elemental Analysis for C$_{19}$H$_{36}$N$_4$O$_6$.H$_2$O: Calcd.: C, 52.52; H, 8.81; N, 12.89 Found : C, 52.72, H, 8.81; N, 12.86

Example 1

Production of (Fmoc-(S)-Cys-O$^t$Bu)$_2$

D-cysteine (5.00 g, 20.8 mmol) was dissolved in 60% perchloric acid (10.2 ml), to which was added, under ice-cooling, t-butyl acetate (117 ml), and the mixture was stirred for two days at 20° C. The reaction mixture was subjected to filtration to collect crystals. The crystals were washed with ether (150 ml), then suspended in a saturated aqueous solution of sodium hydrogencarbonate (100 ml). The suspension was subjected to extraction with ethyl acetate (2×150 ml). Ethyl acetate layers were combined, washed with water and dried over anhydrous sodium sulfate, followed by concentration to given a colorless oily product (4.16 g). This oily product was dissolved in THF (60 ml). To the solution were added, under ice-cooling, N-(9-fluorenylmethyloxycarbonyloxy)succinimide (8.16 g, 24.2 mmol) and N-ethylmorpholine (3.08 ml, 24.2 mmol) dissolved in THF (10 ml), and the mixture was stirred for 2.5 hours at room temperature. The reaction mixture was concentrated, and the concentrate was suspended in a 10% aqueous solution of citric acid (200 ml). The suspension was subjected to extraction with chloroform (2×200 ml). Chloroform layers were combined, washed with water, and then dried over anhydrous sodium sulfate, followed by concentration. The concentrate was crystallized from ethyl acetate to afford (Fmoc-(S)-Cys-O$^t$Bu)$_2$ as colorless crystals (8.68 g, yield 52% ) , m.p. 149.5°–150° C.

$[α]_D^{23}$+5.9° (c=0.52, in chloroform) Elemental Analysis for C$_{44}$H$_{48}$N$_2$O$_8$S$_2$: Calcd.: C, 66.31; H, 6.07; N, 3.51; S, 8.05 Found : C, 66.55; H, 6.13; N, 3.43; S, 7.97

Example 2

Production of (2R,6S)-2-Fmoc-amino-6,7-bis(PamO)-4-THT-OH (GC-1)

a) (Fmoc-(R)-Cys-O$^t$Bu)$_2$ (10.0 g, 12.5 mmol) prepared by the method described in a literature reference (J. W. Metzger et al., Int. J. Peptide Protein Res. 38, p.545, 1991) was dissolved in DCM (80 ml). To the solution were added, under ice-cooling, powdery zinc (3.27 g, 50.0 mmol) and amixture of MeOH-36%HCl-conc.H$_2$SO$_4$ (100:7:1) (hereinafter simply referred to as "acid mixture solution" (40 ml). The resultant mixture was stirred for 30 minutes at 20° C. To the reaction mixture was added (S)-(−)-glycidol (8.29 ml, 125 mmol), which was stirred for two hours at 40° C. The reaction mixture was concentrated until its volume is reduced to 40 ml, then insolubles were filtered off. To the filtrate was added a saturated aqueous saline solution (200 ml), and the mixture was subjected to extraction with DCM (2×300 ml). DCM layers were combined, dried over anhydrous sodium sulfate, and then concentrated. The concentrate was subjected to a silica-gel column chromatography, eluting with ethyl acetate-hexane (1:1, 2:1). Fractions containing the object compound were combined and concentrated to give (2R,6S)-2-Fmoc-amino- 6,7-dihydroxy-4-THT-O$^t$Bu (GC-1a) as a white powdery product (10.9 g, yield 92%).

$[α]_D^{21}$+6.70° (c=0.56, in chloroform) Elemental Analysis for C$_{25}$H$_{31}$NO$_6$.H$_2$O: Calcd.: C, 61.08; H, 6.77; N, 2.85; S, 6.52 Found : C, 60.95; H, 6.62; N, 2.70; S, 6.31.

b) The compound, GC-1a (11.0 g, 23.2 mmol) was dissolved in THF (200 ml), to which were added palmitic acid (19.1 g, 74.3 mmol), DIC (11.6 ml, 74.3 mmol) and 4-dimethylaminopyridine (DMAP, 1.13 g, 9.26 mmol). The mixture was stirred for 12 hours at 20° C. The reaction mixture was concentrated, and the concentrate was suspended in 10% (w/v) aqueous solution of citric acid (400 ml). The suspension was subjected to extraction with ethyl acetate (800 ml). The ethyl acetate layer was washed with water, and then concentrated. The concentrate was subjected to a silica-gel column chromatography, eluting with ethyl acetate-hexane (1:20, 1:10), successively. Fractions containing the object compound were combined and concentrated. The concentrate was crystallized from hexane to give (2R, 6S)-2-Fmoc-amino-6,7-bis(PamO)-4-THT-O$^t$Bu (GC-1b) as colorless crystals. (14.4 g, yield 65%).

m.p. 62.5–63.5° C. Elemental Analysis for $C_{57}H_{91}NO_8S$: Calcd.: C, 72.03; H, 9.65; N, 1.47; S, 3.37 Found : C, 71.94; H, 9.85; N, 1.51; S, 3.23 c) The compound GC-1b (14.4 g, 15.2 mmol) was dissolved in TFA (200 ml), and the solution was left standing for 30 minutes at 20° C. The reaction mixture was concentrated, and the concentrate was dissolved in ethyl acetate (500 ml). This solution was washed with water, dried over anhydrous sodium sulfate, followed by concentration. Resulting crystals were recrystallized from ethyl acetate-hexane to afford GC-1 as colorless crystals (12.4 g, yield 91%)

m.p. 82.5°–83.5° C. $[\alpha]_D^{23}$+14.9° (c=0.55, in chloroform) Elemental Analysis for $C_{53}H_{83}NO_8S$: Calcd.: C, 71.18; H, 9.35; N, 1.57; S, 3.59 Found : C, 70.96; H, 9.36; N, 1.57; S, 3.58

Example 3

Production of (2R, 6R)-2-Fmoc-amino-6,7-dihydroxy-4-THT-O$^t$Bu (GC-2a), (2R, 6R)-2-Fmoc-amino-6,7-bis-(PamO)-4-THT-O$^t$Bu (GC-2b), and (2R, 6R)-2-Fmoc-amino-6,7-bis (PamO)-4-THT-OH (GC-2)

In substantially the same manner as in Example 2, (2R, 6R)-2-Fmoc-amino-6,7-dihydroxy-4-THT-O$^t$Bu (GC-2a), (2R,6R)-2-Fmoc-amino-6,7-bis(PamO)-4-THT-O$^t$Bu (GC-2b), and (2R,6R)-2-Fmoc-amino-6,7-bis(PamO)-4-THT-OH (GC-2) were produced.

| Materials (g) | Reaction Conditions | | Products (g) |
|---|---|---|---|
| a) (Fmoc-(R)-Cys-O$^t$Bu)$_2$ (10.0) | 1) Zinc acid mixt. soln. DCM 20° C. 2) (R)-(+)-glycidol supplemented 40° C. | 3.27 g 40 ml 80 ml 20 min 8.29 ml 2.5 h | GC-2a (10.9) |
| b) GC-2a (3.90) | palmitic acid DIC DMAP THF 20° C. | 6.33 g 3.87 ml 402 mg 70 ml 13 h | GC-2b (4.76) |
| c) GC-2b (2.50) | TFA 20° C. | 50 ml 1.5 h | GC-2 (2.20) |

Compound GC-2a: $[\alpha]_D^{21}$–8.8° (c=0.65, Elemental Analysis for $C_{25}H_{31}NO_6S\cdot0.5H_2O$ Calcd.: C, 62.22; H, 6.68; N, 2.90; S, 6.64 Found : C, 62.14; H, 6.66; N, 2.81; S, 6.54

Compound GC-2b: m.p. 58.0° C. Elemental Analysis for $C_{57}H_{91}NO_8S$: Calcd.: C, 72.03; H, 9.65; N, 1.47; S, 3.37 Found : C, 71.94; H, 9.58; N, 1.43; S, 3.36.

Compound GC-2: m.p. 90.0° C. $[\alpha]_D^{20}$+12.9° (c=0.73, in chloroform) Elemental Analysis for $C_{53}H_{83}NO_8S$: Calcd.: C, 71.18; H, 9.35; N, 1.57; S, 3.59 Found : C, 71.23; H, 9.12; N, 1.54; S, 3.47

Example 4

Production of (2S, 6R)-2-Fmoc-amino-6,7-bis(PamO)-4-THT-O$^t$Bu (GC-3a), (2S,6R)-2-Fmoc-amino-6,7-bis-(PamO)- 4-THT-O$^t$Bu (GC-3b), and (2S, 6R)-2-Fmoc-amino-6,7-bis (PamO)-4-THT-OH (GC-3)

In substantially the same manner as in Example 2, (2S, 6R)-2-Fmoc-amino-6,7-bis(PamO)-4-THT-O$^t$Bu (GC-3a), (2S,6R)-2-Fmoc-amino-6,7-bis(PamO)-4-THT-O$^t$Bu (GC-3b), and (2S,6R)-2-Fmoc-amino-6,7-bis(PamO)-4-THT-OH (GC-3) were produced.

| Materials (g) | Reaction Conditions | | Products (g) |
|---|---|---|---|
| a) (Fmoc-(S)-Cys-O$^t$Bu)$_2$ (2.00) | 1) Zinc acid mixt. soln. DCM 20° C. 2) (S)-(–)-glycidol supplemented 40° C. | 656 mg 8.0 ml 16 ml 30 min 0.67 ml 5 h | GC-3a (2.18) |
| b) GC-3a (1.50) | palmitic acid DIC DMAP THF 20° C. | 2.60 g 1.59 ml 154 mg 30 ml 13 h | GC-3b (2.44) |
| c) GC-3b (2.00) | TFA 20° C. | 40 ml 1.5 h | GC-3 (1.80) |

Compound GC-3a: $[\alpha]_D^{23}$–7.6° (c=0.67, in chloroform) Elemental Analysis for $C_{25}H_{31}N_O6$: Calcd.: C, 63.40; H, 6.60; N, 2.96; S, 6.67 Found : C, 63.12; H, 6.55; N, 2.90; S, 6.81

Compound GC-3b: m.p. 62.5°–63.0° C. Elemental Analysis for $C_{57}H_{91}NO_8S$: Calcd.: C, 72.03; H, 9.65; N, 1.47; S, 3.37 Found : C, 72.04; H, 9.78; N, 1.49; S, 3.38

Compound GC-3: m.p. 82.5°–83.0° C. $[\alpha]_D^{23}$–16.0° (c=0.51, in chloroform) Elemental Analysis for $C_{53}H_{83}NO_8S$: Calcd.: C, 71.18; H, 9.35; N, 1.57; S, 3.59 Found : C, 71.20; H, 9.38; N, 1.45; S, 3.53

Example 5

Production of (2S,6S)-2-Fmoc-amino-6,7-dihydroxy-4-THT-O$^t$Bu (GC-4a), (2S,6S)-2-Fmoc-amino-6,7-bis-(PamO)-4-THT-O$^t$Bu (GC-4b), and (2S,6S)-2-Fmoc-amino-6,7-bis (PamO)-4-THT-OH (GC-4)

In substantially the same manner as in Example 2, (2S, 6S)-2-Fmoc-amino-6,7-dihydroxy-4-THT-O$^t$Bu (GC-4a), (2S,6S)-2-Fmoc-amino-6,7-bis(PamO)-4-THT-O$^t$Bu (GC-4b), and (2S,6S)-2-Fmoc-amino-6,7-bis(PamO)-4-THT-OH (GC-4) were produced.

| Materials (g) | Reaction Conditions | | Products (g) |
|---|---|---|---|
| a) (Fmoc-(S)-Cys-O$^t$Bu)$_2$ (4.00) | 1) Zinc acid mixt. soln. DCM 20° C. 2) (S)-(–)-glycidol supplemented 40° C. | 1.31 g 16 ml 32 ml 20 min 3.33 ml 2.5 h | GC-4a (4.01) |
| b) GC-4a (2.94) | palmitic acid DIC DMAP THF 20° C. | 4.78 g 2.92 ml 303 mg 50 ml 15 h | GC-4b (4.22) |
| c) GC-4b (2.50) | TFA 20° C. | 50 ml 1.5 h | GC-4 (2.24) |

Compound GC-4a: $[\alpha]_D^{23}$+8.4° (C=0.67, in chloroform) Elemental Analysis for $C_{25}H_{31}NO_6S$ Calcd.: C, 63.40; H, 6.60; N, 2.96; S, 6.77 Found : C, 63.15; H, 6.47; N, 2.88; S, 6.67

Compound GC-4b: m.p. 58.0° C. Elemental Analysis for $C_{57}H_{91}NO_8S$: Calcd.: C, 72.03; H, 9.65; N, 1.47; S, 3.37 Found : C, 72.01; H, 9.55; N, 1.34; S, 3.36

Compound GC-4: m.p. 88.5°–89.0° C. $[\alpha]_D^{23}$ –13.1° (C=0.56, in chloroform) Elemental Analysis for $C_{53}H_{83}NO_8S$: Calcd.: C, 71.18; H, 9.35; N, 1.57; S, 3.59 Found : C, 71.20; H, 9.23; N, 1.46; S, 3.56

Example 6

Production of (2R,6S)-2-amino-6,7-bis(PamO)-4-THT-Gly-Gly-Gly-Gly-Glu-Thr -Thr-OH (Compound 1)

a) The compound GC-1 (1.79 g) synthesized in Example 2) was dissolved in DMF (20 ml), to which were added, under ice-cooling, HONB (394 mg), DIC (344 μl) and H-Gly-Gly-Gly-Glu(O$^t$Bu)-Thr($^t$Bu)-Thr($^t$Bu)-O$^t$Bu (P-1) (1.64 g) obtained in Reference Example 1. The mixture was stirred for 24 hours at 20° C. The reaction mixture was concentrated, which was then dissolved in chloroform. The solution was washed with a 10% (w/v) aqueous solution of citric acid, water, a saturated aqueous solution of sodium hydrogencarbonate and water, successively. The chloroform layer was dried over anhydrous sodium sulfate, which was then concentrated. To the concentrate was added acetonitrile. Resulting precipitations were collected by filtration to obtain (2R,6S)-2-Fmoc-amino-6,7-bis(PamO)-4-THT-Gly-Gly-Gly-Gly-Glu-(O$^t$Bu)-Thr($^t$Bu)-Thr($^t$Bu)-O$^t$Bu (1a) as a white powdery product (3.16 g, yield 97%).

$[\alpha]_D^{18}$ +6.5° (c=0.54, in chloroform) Elemental Analysis for $C_{88}H_{145}N_7O_{18}S$: Calcd.: C, 65.20; H, 9.02; N, 6.05; S, 1.98 Found : C, 64.90; H, 8.83; N, 5.86; S, 1.78 Amino acid analysis [6N HCl 110° C., hydrolysis for 20 hours; Values in parentheses show theoretical ones.]: Glu 1.00 (1); Thr 1.93 (2); Gly 2.96 (3) FAB-MS (M+Na)=1643 (theoretical value=1643)

b) The compound 1a (2.70 g) was dissolved in DMF (27 ml). To the solution was added piperidine (2.7 ml), and the mixture was stirred for one hour at 20° C. The reaction mixture was concentrated and subjected to a silica-gel column chromatography, eluting with chloroform-methanol (50:1, 20:1), successively. Fractions containing the object compound were combined and concentrated to leave (2R, 6S)-2-amino-6,7-bis (PamO)-4-THT-Gly-Gly-Gly-Glu-(O$^t$Bu)-Thr($^t$Bu)-Thr($^t$Bu)-O$^t$Bu (1b) as a white powdery product (2.10 g, yield 90%).

$[\alpha]_D^{18}$ +7.1° (c=0.49, in chloroform) Elemental Analysis for $C_{73}H_{135}N_7O_{16}S$: Calcd.: C, 62.67; H, 9.73; N, 7.01; S, 2.29 Found : C, 62.55; H, 9.85; N, 6.95; S, 2.21 Amino acid analysis [6N HCl, 110° C., hydrolysis for 20 hours; Values in parentheses show theoretical ones.]: Glu 1.00 (1); Thr 1.92 (2); Gly 2.95 (3) FAB-MS (M+Na)=1399 (theoretical value=1399)

c) The compound 1b (200 mg) was dissolved in TFA (2.0 ml), which was left standing for 1.5 hour at 20° C. The reaction mixture was concentrated, to which was added acetonitrile. Resulting precipitates were collected by filtration to obtain the compound 1 as a white powdery product (164 mg).

Elemental Analysis for $C_{57}H_{103}N_7O_{16}S \cdot 1.5H_2O$: Calcd.: C, 56.98; H, 8.89; N, 8.16; S, 2.67 Found : C, 57.04; H, 8.80; N, 8.11; S, 2.72

Example 7

Production of (2R,6R)-2-amino-6,7-bis(PamO)-4-THT-Gly-Gly-Gly-Glu-Thr Thr-OH (Compound 2)

In substantially the same manner as in Example 6, (2R, 6R)-2-Fmoc-amino-6,7-bis(PamO)-4-THT-Gly-Gly-Gly-Glu(O$^t$Bu)-Thr($^t$Bu)-Thr($^t$Bu)-O$^t$Bu (2a), (2R,6R)-2-amino-6,7-bis(PamO)-4-THT-Gly-Gly-Gly-Glu(O$^t$Bu)-Thr($^t$Bu)-Thr($^t$Bu)-O$^t$Bu(2b), and (2R,6R)-2-amino-6,7-bis(PamO)-4-THT-Gly-Gly-Gly-Glu-Thr-Thr-OH (Compound 2) were produced.

| Materials (mg) | Reaction Conditions | | Products (mg) |
|---|---|---|---|
| a) GC-2 (500) | P-1 HONB DIC DMF 20° C. | 458 mg 110 mg 96 μl 5.0 ml 15 h | 2a (873) |
| b) 2a (770) | piperidine DMF 20° C. silica-gel (chloroform-methanol) 50:1, 20:1 | 0.70 ml 7.0 ml 1 h | 2b (623) |
| c) 2b (150) | TFA 20° C. | 1.5 ml 1.5 h | 2 (125) |

Compound 2a: $[\alpha]_D^{20}$ +3.4° (c=0.66, in chloroform) Elemental Analysis for $C_{88}H_{145}N_7O_{18}S \cdot 0.5H_2O$: Calcd.: C, 64.84; H, 9.03; N, 6.01; S, 1.97 Found: C, 64.88; H, 9.18; N, 6.08; S, 1.95

Compound 2b: $[\alpha]_D^{20}$ +4.90° (c=0.55, in chloroform) Elemental Analysis for $C_{73}H_{135}N_7O_{16}S \cdot 0.5H_2O$: Calcd.: C, 62.27; H, 9.74; N, 6.96; S, 2.28 Found : C, 62.31; H, 9.73; N, 6.99; S, 2.19

Compound 2: $[\alpha]_D^{21}$ –2.3° (c=0.58, in 5% TFA-chloroform) Elemental Analysis for $C_{53}H_{103}N_7O_{16}S \cdot 1.5H_2O$: Calcd.: C, 56.98; H, 8.89; N, 8.16; S, 2.67 Found : C, 56.72; H, 8.62; N, 8.11; S, 2.63

Example 8

Production of (2S,6R)-2-amino-6,7-bis(PamO)-4-THT-Gly-Gly-Glu-Thr-Thr-OH (Compound 3)

In substantially the same manner as in Example 6, (2S, 6R)-2-Fmoc-amino-6,7-bis(PamO)-4-THT-Gly-Gly-Gly-Glu(O$^t$Bu)-Thr($^t$Bu)-Thr($^t$Bu)-O$^t$Bu (3a), (2S,6R)-2-amino-6,7-bis(PamO)-4-THT-Gly-Gly-Gly-Glu(O$^t$Bu)-Thr($^t$Bu)-Thr-($^t$Bu)-O$^t$Bu (3b), and (2S,6R)-2-amino-6,7-bis(PamO)-4-THT-Gly-Gly-Gly-Glu-Thr-Thr-OH (Compound 3) were produced.

| Materials (mg) | Reaction Conditions | | Products (mg) |
|---|---|---|---|
| a) GC-3 (500) | P-1 HONB DIC DMF 20° C. | 458 mg 110 mg 96 μl 5.0 ml 15 h | 3a (885) |
| b) 3a (830) | piperidine DMF 20° C. silica-gel (chloroform-methanol) 50:1, 20:1 | 0.80 ml 8.0 ml 1.5 h | 3b (624) |
| c) 3b (160) | TFA 20° C. | 1.6 ml 1.5 h | 3 (130) |

Compound 3a: $[\alpha]_D^{20}$ +15.9° (C=0.51, in chloroform) Elemental Analysis for $C_{88}H_{145}N_7O_{18}S \cdot 0.5H_2O$: Calcd.: C, 64.84; H, 9.03; N, 6.01; S, 1.97 Found : C, 64.63; H, 9.07; N, 5.80; S, 2.21

Compound 3b: $[\alpha]_D^{20}$ +21.4° (c=0.64, in chloroform) Elemental Analysis for $C_{73}H_{135}N_7O_{16}S$: Calcd.: C, 62.68; H, 9.73; N, 7.01; S, 2.29 Found : C, 62.75; H, 9.41; N, 7.05; S, 2.40

Compound 2: $[\alpha]_D^{21}$ –21.7° (c=0.63, in 5% TFA-chloroform) Elemental Analysis for $C_{57}H_{103}N_7O_{16}S \cdot H_2O$: Calcd.: C, 57.41; H, 8.88; N, 8.22; S, 2.69 Found : C, 57.38; H, 8.66; N, 8.27; S, 2.59

Example 9

Production of (2S,6S)-2-amino-6,7-bis(PamO)-4-THT-Gly-Gly-Glu-Thr-Thr-OH (Compound 4)

In substantially the same manner as in Example 6, (2S,6S)-2-Fmoc-amino-6,7-bis(PamO)-4-THT-Gly-Gly-Gly-Glu-(O$^t$Bu)-Thr($^t$Bu)-Thr($^t$Bu)-O$^t$Bu (4a), (2S,6S)-2-amino-6,7-bis(PamO)-4-THT-Gly-Gly-Gly-Glu(O$^t$Bu)-Thr($^t$Bu)-Thr($^t$Bu)-O$^t$Bu (4b), and (2S,6S)-2-amino-6,7-bis(PamO)-4-THT-Gly-Gly-Gly-Glu-Thr-Thr-OH (Compound 4) were produced.

| Materials (mg) | Reaction Conditions | Products (mg) |
| --- | --- | --- |
| a) GC-4 (500) | P-1<br>HONB<br>DIC<br>DMF<br>20° C. | 458 mg 4a<br>110 mg (879)<br>96 µl<br>5.0 ml<br>15 h |
| b) 4a (820) | piperidine<br>DMF<br>20° C.<br>silica-gel<br>(chloroform-methanol)<br>50:1, 20:1 | 0.80 ml 4b<br>8.0 ml (651)<br>1 h |
| c) 4b (160) | TFA<br>20° C. | 1.6 ml 4<br>1.5 h (131) |

Compound 4a: $[\alpha]_D^{20}$+15.3° (C=0.65, in chloroform) Elemental Analysis for $C_{88}H_{145}N_7O_{18}S$: Calcd.: C, 65.20; H, 9.02; N, 6.05; S, 1.98 Found: C, 65.05; H, 9.05; N, 6.07; S, 1.86

Compound 4b: $[\alpha]_D^{20}$+24.4° (C=0.62, in chloroform) Elemental Analysis for $C_{73}H_{135}N_7O_{16}S$: Calcd.: C, 62.68; H, 9.73; N, 7.01; S, 2.29 Found: C, 62.53; H, 9.48; N, 6.93; S, 2.31

Compound 4: $[\alpha]_D^{21}$−15.6° (c=0.5, in 5% TFA-chloroform) Elemental Analysis for $C_{53}H_{103}N_7O_{16}S \cdot 1.5H_2O$: Calcd.: C, 56.98; H, 8.89; N, 8.16; S, 2.67 Found: C, 56.74; H, 8.57; N, 8.03; S, 2.72

Example 10

Production of (2R,6R)-2-amino-6,7-bis(PamO)-4-THT-Gly-Gly-Gly-Glu-Thr-OH (Compound 5)

In substantially the same manner as in Example 6, (2R,6R)-2-Fmoc-amino-6,7-bis(PamO)-4-THT-Gly-Gly-Gly-Glu(O$^t$Bu)-Thr($^t$Bu)-O$^t$Bu (5a), (2R,6R)-2-amino-6,7-bis(PamO)-4-THT-Gly-Gly-Gly-Glu(O$^t$Bu)-Thr($^t$Bu)-O$^t$Bu (5b) and (2R,6R)-2-amino-6,7-bis(PamO)-4-THT-Gly-Gly-Gly-Glu-Thr-OH (Compound 5) were produced.

| Materials (g) | Reaction Conditions | Products (g) |
| --- | --- | --- |
| a) GC-2 (1.23) | P-2<br>HONB<br>DIC<br>DMF<br>20° C. | 809 mg 5a<br>271 mg (1.91)<br>0.24 ml<br>20 ml<br>19 h |
| b) 5a (1.30) | piperidine<br>DCM<br>20° C.<br>silica-gel<br>(chloroform-methanol)<br>49:1, 19:1, 14:1 | 1.3 ml 5b<br>13 ml (0.99)<br>1.3 h |
| c) 5b (0.49) | TFA<br>20° C. | 2 ml 5<br>2 h (0.43) |

Compound 5a: $[\alpha]_D^{23}$−6.9° (C=0.51, in chloroform) Elemental Analysis for $C_{80}H_{130}N_6O_{16}S$: Calcd.: C, 65.63; H, 8.95; N, 5.74; S, 2.19 Found: C, 65.59; H, 9.16; N, 5.94; S, 2.27

Compound 5b: $[\alpha]_D^{23}$−6.9° (C=0.50, in chloroform) Elemental Analysis for $C_{65}H_{120}N_6O_{14}S$: Calcd.: C, 62.87; H, 9.74; N, 6.77; S, 2.58 Found: C, 62.96; H, 9.57; N, 6.89; S, 2.42

Compound 5: $[\alpha]_D^{23}$+4.9° (c=0.49 in 5% TFA-chloroform) Elemental Analysis for $C_{53}H_{96}N_6O_{14}S \cdot 0.5H_2O$: Calcd.: C, 58.81; H, 9.03; N, 7.76; S, 2.96 Found: C, 58.94; H, 8.82; N, 7.70; S, 2.99

Example 11

Production of (2R,6R)-2-amino-6,7-bis(PamO)-4-THT-Glu-Gly-Glu-Gly-D-Glu-OH (Compound 6)

In substantially the same manner as in Example 6, (2R,6R)-2-Fmoc-amino-6,7-bis(PamO)-4-THT-Glu(O$^t$Bu)-Gly-Glu(O$^t$Bu)-Gly-D-Glu(O$^t$Bu)-O$^t$Bu (6a), (2R,6R)-2-amino-6,7-bis(PamO)-4-THT-Glu(O$^t$Bu)-Gly-Glu(O$^t$Bu)-Gly-D-Glu(O$^t$Bu)-(O$^t$Bu) (6b) and (2R,6R)-2-amino-6,7-bis(PamO)-4-THT-Glu-Gly-Glu-Gly-D-Glu-OH (Compound 6) were produced.

| Materials (g) | Reaction Conditions | Products (g) |
| --- | --- | --- |
| a) GC-2 (0.51) | P-3<br>HONB<br>DIC<br>DMF<br>20° C. | 470 mg 6a<br>113 mg (0.71)<br>0.10 ml<br>5 ml<br>16 h |
| b) 6a (0.66) | piperidine<br>DCM<br>20° C.<br>silica-gel<br>(chloroform-methanol)<br>50:1, 20:1 | 0.7 ml 6b<br>6.3 ml (0.56)<br>1.0 h |
| c) 6b (0.25) | TFA<br>20° C. | 3.0 ml 6<br>3 h (0.20) |

Compound 6a: $[\alpha]_D^{23}$+1.8° (c=0.50, in chloroform) Elemental Analysis for $C_{88}H_{142}N_6O_{19}S$: Calcd.: C, 65.24; H, 8.83; N, 5.19; S, 1.98 Found: C, 65.05; H, 8.87; N, 5.15; S, 1.91

Compound 6b: $[\alpha]_D^{23}$+1.0° (c=0.50, in chloroform) Elemental Analysis for $C_{73}H_{132}N_6O_{17}S \cdot 0.5H_2O$: Calcd.: C, 62.32; H, 9.53; N, 5.97; S, 2.28 Found: C, 62.30; H, 9.53; N, 5.77; S, 2.19

Compound 6: $[\alpha]_D^{21}$+3.8° (c=0.53 in 5% TFA-chloroform) Elemental Analysis for $C_{50}H_{90}N_4O_{13}S \cdot H_2O$: Calcd.: C, 57.46; H, 8.63; N, 7.05; S, 2.69 Found: C, 57.56; H, 8.60; N, 7.24; S, 2.54

Example 12

Production of (2R,6R)-2-amino-6,7-bis(PamO)-4-THT-Gly-Gly-Gly-Glu-OH (Compound 7)

In substantially the same manner as in Example 6, (2R,6R)-2-Fmoc-amino-6,7-bis(PamO)-4-THT-Gly-Gly-Gly-Glu (O$^t$Bu)-O$^t$Bu (7a), (2R,6R)-2-amino-6,7-bis(PamO)-4-THT-Gly-Gly-Gly-Glu (O$^t$Bu)-O$^t$Bu (7b) and (2R,6R)-2-amino-6,7-bis(PamO)-4-THT-Gly-Gly-Gly-Glu-OH (Compound 7) were produced.

| Materials (g) | Reaction Conditions | Products (g) |
| --- | --- | --- |
| a) GC-2 (1.31) | P-4<br>HONB<br>DIC | 630 mg 7a<br>288 mg (1.64)<br>0.25 ml |

| Materials (g) | | Reaction Conditions | Products (g) |
|---|---|---|---|
| | | -continued | |
| | | DCM | 19 ml |
| | | 20° C. | 15 h |
| b) 7a | | piperidine | 1.2 ml 7b |
| (1.18) | | DCM | 12 ml (0.92) |
| | | 20° C. | 1.3 h |
| | | silica-gel | |
| | | (chloroform-methanol) | |
| | | 49:1, 19:1, 14:1 | |
| c) 7b | | TFA | 2 ml 7 |
| (0.45) | | 20° C. | 2 h (0.38) |

Compound 7a: $[\alpha]_D^{23} -6.4°$ (C=0.50, in chloroform) Elemental Analysis for $C_{72}H_{115}N_5O_{14}S$: Calcd.: C, 66.18; H, 8.87; N, 5.36; S, 2.45 Found : C, 66.03; H, 8.87; N, 5.31; S, 2.22

Compound 7b: $[\alpha]_D^{23} -6.7°$ (c=0.63, in chloroform) Elemental Analysis for $C_{57}H_{105}N_5O_{12}S \cdot H_2O$: Calcd.: C, 62.09; H, 9.78; N, 6.35; S, 2.91 Found : C, 62.12; H, 9.59; N, 6.36; S, 2.87

Compound 7: $[\alpha]_D^{23} +8.30°$ (c=0.60 in 5% TFA-chloroform) Elemental Analysis for $C_{49}H_{89}N_5O_{12}S \cdot H_2O$: Calcd.: C, 59.43; H, 9.26; N, 7.07; S, 3.24 Found : C, 59.19; H, 8.96; N, 6.96; S, 3.26

Example 13

Production of (2R,6R)-2-amino-6,7-bis(PamO)-4-THT-Gly-Gly-Gly-D-Glu-OH (Compound 8)

In substantially the same manner as in Example 6, (2R, 6R)-2-Fmoc-amino-6,7-bis(PamO)-4-THT-Gly-Gly-Gly-D-Glu(O'Bu)-O'Bu (8a), (2R,6R)-2-amino-6,7-bis(PamO)-4-THT-Gly-Gly-D-Glu (O'Bu)-O'Bu (8b) and (2R,6R)-2-amino-6,7-bis(PamO)-4-THT-Gly-Gly-Gly-D-Glu-OH (Compound 8) were produced.

| Materials (g) | Reaction Conditions | Products (g) |
|---|---|---|
| a) GC-2 | P-5 | 1.53 g 8a |
| (1.92) | HONB | 684 mg (3.93) |
| | DIC | 0.59 ml |
| | DMF | 33 ml |
| | 20° C. | 15 h |
| b) 8a | piperidine | 0.82 ml 8b |
| (0.82) | DCM | 8.2 ml (0.64) |
| | 20° C. | 2 h |
| | silica-gel | |
| | (chloroform-methanol) | |
| | 49:1, 19:1, 14:1 | |
| c) 8b | TFA | 2 ml 8 |
| (0.58) | 20° C. | 2 h (0.45) |

Compound 8a: $[\alpha]_D^{23} -7.1°$ (c=0.49, in chloroform) Elemental Analysis for $C_{72}H_{115}N_5O_{14}S$: Calcd.: C, 66.18; H, 8.87; N, 5.36; S, 2.45 Found : C, 66.12; H, 8.77; N, 5.52; S, 2.45

Compound 8b: $[\alpha]_D^{23} -14.5°$ (c=0.53, in chloroform) Elemental Analysis for $C_{57}H_{105}N_5O_{12}S$: Calcd.: C, 63.13; H, 9.76; N, 6.46; S, 2.96 Found : C, 63.10; H, 9.83; N, 6.44; S, 2.77

Compound 8: $[\alpha]_D^{23} +8.1°$ (c=0.62 in 5% TFA-chloroform) Elemental Analysis for $C_{49}H_{89}N_5O_{12}S \cdot 0.5H_2O$: Calcd.: C, 59.97; H, 9.24; N, 7.14; S, 3.27 Found : C, 59.82; H, 9.14; N, 6.96; S, 3.38

Example 14

Production of (2R,6S)-2-amino-6,7-bis(PamO)-4-THT-Gly-Gly-Gly-Glu-OH (Compound 9)

In substantially the same manner as in Example 6, (2R, 6S)-2-Fmoc-amino-6,7-bis(PamO)-4-THT-Gly-Gly-Gly-Glu (O'Bu)-O'Bu (9a), (2R,6S)-2-amino-6,7-bis(PamO)-4-THT-Gly-Gly-Gly-Glu(O'Bu)-O'Bu (9b) and (2R,6S)-2-amino- 6,7-bis(PamO)-4-THT-Gly-Gly-Gly-Glu-OH (Compound 9) were produced.

| Materials (g) | Reaction Conditions | Products (g) |
|---|---|---|
| a) GC-1 | P-4 | 490 mg 9a |
| (1.02) | HONB | 229 mg (1.25) |
| | DIC | 0.20 ml |
| | DMF | 15 ml |
| | 20° C. | 18 h |
| b) 9a | piperidine | 1.10 ml 9b |
| (1.10) | DCM | 11 ml (0.777) |
| | 20° C. | 1.5 h |
| | silica-gel | |
| | (chloroform-methanol) | |
| | 49:1, 19:1 | |
| c) 9b | TFA | 3.0 ml 9 |
| (0.300) | 20° C. | 1.5 h (0.266) |

Compound 9a: $[\alpha]_D^{24} -3.3°$ (C=0.51, in chloroform) Elemental Analysis for $C_{72}H_{115}N_5O_{14}S \cdot H_2O$: Calcd.: C, 66.18; H, 8.87; N, 5.36; S, 2.45 Found : C, 66.10; H, 8.89; N, 5.46; S, 2.58

Compound 9b: $[\alpha]_D^{21} -5.5°$ (C=0.73, in chloroform) Elemental Analysis for $C_{57}H_{105}N_5O_{12}S$: Calcd.: C, 63.13; H, 9.76; N, 6.46; S, 2.96 Found : C, 62.84; H, 9.61; N, 6.42; S, 2.96

Compound 9: $[\alpha]_D^{21} +13.5°$ (C=0.67 in 5% TFA-chloroform) Elemental Analysis for $C_{49}H_{89}N_5O_{12}S \cdot 2.5H_2O$: Calcd.: C, 57.85; H, 9.31; N, 6.88; S, 3.15 Found : C, 57.89; H, 8.82; N, 6.88; S, 3.05

Example 15

Production of (2R,6S)-2-amino-6,7-bis(PamO)-4-THT-Gly-Gly-Gly-D-Glu-OH (Compound 10)

In substantially the same manner as in Example 6, (2R, 6S)-2-Fmoc-amino-6,7-bis(PamO)-4-THT-Gly-Gly-Gly-D-Glu (O'Bu)-O'Bu (10a), (2R,6S)-2-amino-6,7-bis(PamO)-4-THT-Gly-Gly-D -Glu(O'Bu)-O'Bu (10b) and (2R,6S)-2-amino- 6,7-bis(PamO)-4-THT-Gly-Gly-Gly-D-Glu-OH (Compound 10) were produced.

| Materials (g) | Reaction Conditions | Products (g) |
|---|---|---|
| a) GC-1 | P-5 | 1.61 g 10a |
| (2.41) | HONB | 541 mg (3.45) |
| | DIC | 0.47 ml |
| | DMF | 25 ml |
| | 20° C. | 19 h |
| b) 10a | piperidine | 1.10 ml 10b |
| (1.10) | DMF | 11 ml (0.783) |
| | 20° C. | 1.5 h |
| | silica-gel | |
| | (chloroform-methanol) | |
| | 49:1, 19:1 | |
| c) 10b | TFA | 3.0 ml 10 |
| (0.300) | 20° C. | 1.5 h (0.262) |

Compound 10a: $[\alpha]_D^{24}$ –5.1° (c=0.57, in chloroform) Elemental Analysis for $C_{72}H_{115}N_5O_{14}S.H_2O$: Calcd.: C, 66.18; H, 8.87; N, 5.36; S, 2.45 Found : C, 66.07; H, 8.94; N, 5.48; S, 2.49

Compound 10b: $[\alpha]_D^{21}$ –10.7° (C=0.57, in chloroform) Elemental Analysis for $C_{57}H_{105}N_5O_{12}S$: Calcd.: C, 63.13; H, 9.76; N, 6.46; S, 2.96 Found : C, 63.13; H, 9.51; N, 6.46; S, 2.96

Compound 10: $[\alpha]_D^{21}$ +13.2° (C=0.67 in 5% TFA-chloroform) Elemental Analysis for $C_{49}H_{89}N_5O_{12}S.2H_2O$: Calcd.: C, 58.36; H, 9.29; N, 6.95; S, 3.18 Found : C, 58.30; H, 8.90; N, 6.76; S, 3.25

Example 16

Production of (2R,6R)-2-amino-6,7-bis(PamO)-4-THT-Glu-Gly-D-Glu-OH (Compound 11)

In substantially the same manner as in Example 6, (2R, 6R)-2-Fmoc-amino-6,7-bis(PamO)-4-THT-Glu(O$^t$Bu)-Gly-D-Glu (O$^t$Bu)-O$^t$Bu (11a), (2R,6R)-2-amino-6,7-bis-(PamO)-4-THT-Glu(O$^t$Bu)-Gly-D-Glu (O$^t$Bu)-O$^t$Bu (11b) and (2R,6R)- 2-amino-6,7-bis(PamO)-4-THT-Glu-Gly-D-Glu-OH (Compound 11) were produced.

| Materials (g) | | Reaction Conditions | Products (g) | |
|---|---|---|---|---|
| a) | GC-2 (2.04) | P-6 HONB DIC DMF 20° C. | 1.31 g 453 mg 0.40 ml 20 ml 16 h | 11a (2.72) |
| b) | 11a (2.00) | piperidine DCM 20° C. silica-gel (ethylacetate-methanol) 10:0, 9:1 | 2.0 ml 18 ml 1 h | 11b (1.75) |
| c) | 11b (0.80) | TFA 20° C. | 8.0 ml 2 h | (0.56) |

Compound 11a: $[\alpha]_D^{23}$ –7.0° (c=0.56, in chloroform) Elemental Analysis for $C_{77}H_{124}N_4O_{15}S$: Calcd.: C, 67.12; H, 9.07; N, 4.07; S, 2.33 Found : C, 67.01; H, 9.19; N, 4.01; S, 2.31

Compound 11b: $[\alpha]_D^{23}$ –18° (C=0.53, in chloroform) Elemental Analysis for $C_{62}H_{114}N_4O_{13}S$: Calcd.: C, 64.44; H, 9.94; N, 4.85; s, 2.77 Found : C, 64.23; H, 9.95; N, 4.94; S, 2.64

Compound 11: $[\alpha]_D^{21}$ +2.1° (C=0.53 in 5% TFA-chloroform) Elemental Analysis for $C_{50}H_{90}N_4O_{13}S.H_2O$: Calcd.: C, 59.73; H, 9.22; N, 5.57; s, 3.19 Found : C, 59.56; H, 9.05; N, 5.48; s, 3.15

Example 17

Production of (2R,6R)-2-amino-6,7-bis(PamO)-4-THT-Gly-Gly-Glu-OH (Compound 12)

In substantially the same manner as in Example 6, (2R, 6R)-2-Fmoc-amino-6,7-bis(PamO)-4-THT-Gly-Gly-Glu-(O$^t$Bu)-O$^t$Bu (12a), (2R,6R)-2-amino-6,7-bis(PamO)-4-THT-Gly-Gly-Glu (O$^t$Bu)-O$^t$Bu (12b) and (2R,6R)-2-amino-6,7-bis(PamO)-4-THT-Gly-Gly-Glu-OH (Compound 12) were produced.

| Materials (g) | | Reaction Conditions | Products (g) | |
|---|---|---|---|---|
| a) | GC-2 (2.00) | P-7 HONB DIC DMF 20° C. | 918 mg 441 mg 0.39 ml 20 ml 15 h | 12a (1.81) |
| b) | 12a (1.75) | piperidine DCM 20° C. silica-gel (chloroform-methanol) 50:1, 20:1 | 1.8 ml 18 ml 1.5 h | 12b (1.32) |
| c) | 12b (0.60) | TFA 20° C. | 5 ml 2 h | 12 (0.52) |

Compound 12a: $[\alpha]_D^{23}$ –5.2° (c=0.58, in chloroform) Elemental Analysis for $C_{70}H_{112}N_4O_{13}S$: Calcd.: C, 67.28; H, 9.03; N, 4.48; S, 2.57 Found : C, 67.22; H, 8.84; N, 4.55; S, 2.51

Compound 12b: $[\alpha]_D^{23}$ –7.9° (C=0.60, in chloroform) Elemental Analysis for $C_{55}H_{102}N_4O_{11}S.0.5H_2O$: Calcd.: C, 63.73; H, 10.02; N, 5.41; S, 3.09 Found : C, 63.88; H, 10.22; N, 5.48; S, 3.09

Compound 12: $[\alpha]_D^{23}$ +14.8° (c=0.68 in 5% TFA-chloroform) Elemental Analysis for $C_{47}H_{86}N_4O_{11}S.2.5H_2O$: Calcd.: C, 58.78; H, 9.55; N, 5.83; S, 3.34 Found : C, 58.91; H, 8.83; N, 5.67; S, 3.06

Example 18

Production of (2R,6R)-2-amino-6,7-bis(PamO)-4-THT-Gly-Gly-Gly-OH (Compound 13)

In substantially the same manner as in Example 6, (2R, 6R)-2-Fmoc-amino-6,7-bis(PamO)-4-THT-Gly-Gly-Gly-O$^t$Bu (13a), (2R,6R)-2-amino-6,7-bis(PamO)-4-THT-Gly-Gly-Gly-O$^t$Bu (13b) and (2R,6R)-2-amino-6,7-bis(PamO)-4-THT-Gly-Gly-Gly-OH (Compound 13) were produced.

| Materials (g) | | Reaction Conditions | Products (g) | |
|---|---|---|---|---|
| a) | GC-2 (2.18) | H—Gly—Gly—Gly-O$^t$Bu HONB DIC DMF 20° C. | 660 mg 482 mg 0.42 ml 20 ml 17 h | 13a (2.50) |
| b) | 13a (1.80) | piperidine DCM 20° C. silica-gel (chloroform-methanol) 50:1, 20:1 | 1.8 ml 18 ml 1.3 h | 13b (1.30) |
| c) | 13b (0.60) | TFA 20° C. | 5 ml 2 h | 13 (0.55) |

Compound 13a: $[\alpha]_D^{23}$ –11.0° (c=0.60, in chloroform) Elemental Analysis for $C_{63}H_{100}N_4O_{11}S$: Calcd.: C, 67.47; H, 8.99; N, 5.00; S, 2.86 Found : C, 67.47; H, 8.86; N, 4.92; S, 2.89

Compound 13b: $[\alpha]_D^{23}$ 14.3° (c=0.48, in chloroform) Elemental Analysis for $C_{48}H_{90}N_4O_9S$: Calcd.: C, 64.11; H, 10.09; N, 6.23; S, 3.57 Found : C, 63.97; H, 10.01; N, 6.21; S, 3.44

Compound 13: $[\alpha]_D^{23}$ +12.2° (c=0.63 in 5% TFA-chloroform) Elemental Analysis for $C_{44}H_{82}N_4O_9S.2.5H_2O$: Calcd.: C, 59.50; H, 9.87; N, 6.31; S, 3.61 Found : C, 59.21; H, 9.17; N, 6.16; S, 3.34

Example 19

Production of (2R,6R)-2-amino-6,7-bis(PamO)-4-THT-Gly-Glu-OH (Compound 14)

In substantially the same manner as in Example 6, (2R,6R)-2-Fmoc-amino-6,7-bis(PamO)-4-THT-Gly-Glu(O$^t$Bu)-O$^t$Bu (14a), (2R,6R)-2-amino-6,7-bis(PamO)-4-THT-Gly-Glu (O$^t$Bu)-O$^t$Bu (14b) and (2R,6R)-2-amino-6,7-bis(PamO)-4-THT-Gly-Glu-OH (Compound 14) were produced.

| Materials (g) | Reaction Conditions | Products (g) |
|---|---|---|
| a) GC-2 (2.03) | H—Gly—Glu(O$^t$Bu)-O$^t$Bu<br>HONB<br>DIC<br>DMF<br>20° C. | 777 mg 14a<br>441 mg (2.20)<br>0.39 ml<br>20 ml<br>16 h |
| b) 14a (1.40) | piperidine<br>DCM<br>20° C.<br>silica-gel<br>(chloroform-methanol)<br>50:1, 20:1 | 1.4 ml 14b<br>14 ml (0.90)<br>1.0 h |
| c) 14b (0.40) | TFA<br>20° C. | 4.0 ml 14<br>2 h (0.29) |

Compound 14a: $[\alpha]_D^{23}$ −2.0° (c=0.50, in chloroform) Elemental Analysis for $C_{68}H_{109}N_3O_{12}S$: Calcd.: C, 68.48; H, 9.21; N, 3.52; S, 2.69 Found : C, 68.62; H, 9.26; N, 3.60; S, 2.68

Compound 14b $[\alpha]_D^{23}$ −5.6° (C=0.57, in chloroform) Elemental Analysis for $C_{53}H_{99}N_3O_{10}S$: Calcd.: C, 65.60; H, 10.28; N, 4.33; S, 3.30 Found : C, 65.51; H, 10.31; N, 4.20; S, 3.25

Compound 14: $[\alpha]_D^{21}$ +2.1° (c=0.53 in 5% TFA-chloroform) Elemental Analysis for $C_{45}H_{83}N_3O_{10}S \cdot 0.5H_2O$: Calcd.: C, 62.32; H, 9.76; N, 4.85; S, 3.70 Found : C, 62.16; H, 9.64; N, 4.61; S, 3.67

Example 20

Production of (2R,6R)-2-amino-6,7-bis(PamO)-4-THT-Glu-OH (Compound 15)

In substantially the same manner as in Example 6, (2R,6R)-2-Fmoc-amino-6,7-bis(PamO)-4-THT-Glu(O$^t$Bu)-O$^t$Bu (15a), (2R,6R)-2-amino-6,7-bis(PamO)-4-THT-Glu-(O$^t$Bu)-O$^t$Bu (15b) and (2R,6R)-2-amino-6,7-bis(PamO)-4-THT-Glu-OH (Compound 15) were produced.

| Materials (g) | Reaction Conditions | Products (g) |
|---|---|---|
| a) GC-2 (4.00) | H—Glu(O$^t$Bu)-O$^t$Bu<br>HONB<br>DIC<br>DMF<br>20° C. | 1.27 g 15a<br>882 mg (4.80)<br>0.77 ml<br>30 ml<br>17 h |
| b) 15a (2.30) | piperidine<br>DCM<br>20° C.<br>silica-gel<br>(chloroform-methanol)<br>50:1, 20:1 | 2.3 ml 15b<br>23 ml (1.14)<br>1.3 h |
| c) 15b (0.48) | TFA<br>20° C. | 5 ml 15<br>2 h (0.41) |

Compound 15a: $[\alpha]_D^{23}$ −2.0° (c=0.58, in chloroform) Elemental Analysis for $C_{66}H_{106}N_2O_{11}S$: Calcd.: C, 69.81; H, 9.41; N, 2.47; S, 2.82 Found : C, 69.79; H, 9.26; N, 2.44; S, 2.74

Compound 15b: $[\alpha]_D^{23}$ −10.1° (C=0.56, in chloroform) Elemental Analysis for $C_{51}H_{96}N_2O_9S$: Calcd.: C, 67.06; H, 10.59; N, 3.07; S, 3.51 Found : C, 67.04; H, 10.36; N, 3.09; S, 3.45

Compound 15: $[\alpha]_D^{23}$ +3.7° (c=0.60 in 5% TFA-chloroform) Elemental Analysis for $C_{43}H_{80}N_2O_9S \cdot 0.5H_2O$: Calcd.: C, 63.75; H, 10.08; N, 3.46; S, 3.96 Found : C, 63.70; H, 9.75; N, 3.31; S, 3.88

Example 21

Production of (2R,6R)-2-amino-6,7-bis(PamO)-4-THT-Gly-Gly-Gly-Asp-OH (Compound 16)

In substantially the same manner as in Example 6, (2R,6R)-2-Fmoc-amino-6,7-bis(PamO)-4-THT-Gly-Gly-Gly-Asp (O$^t$Bu)-O$^t$Bu (16a), (2R,6R)-2-amino-6,7-bis(PamO)-4-THT-Gly-Gly-Gly-Asp (O$^t$Bu)-O$^t$Bu (16b) and (2R,6R)-2-amino- 6,7-bis(PamO)-4-THT-Gly-Gly-Gly-Asp-OH (Compound 16) were produced.

| Materials (g) | Reaction Conditions | Products (g) |
|---|---|---|
| a) GC-2 (2.28) | P-8<br>HONB<br>DIC<br>DMF<br>20° C. | 1.17 g 16a<br>502 mg (3.13)<br>0.44 ml<br>20 ml<br>15 h |
| b) 16a (2.94) | piperidine<br>DCM<br>20° C.<br>silica-gel<br>(chloroform-methanol)<br>50:1, 20:1 | 3.0 ml 16b<br>30 ml (1.83)<br>2 h |
| c) 16b (0.83) | TFA<br>20° C. | 9 ml 16<br>2 h (0.74) |

Compound 16a: $[\alpha]_D^{22}$ +37° (C=0.61, in chloroform) Elemental Analysis for $C_{71}H_{113}N_5O_{14}S$: Calcd.: C, 65.97; H, 8.81; N, 5.42; S, 2.48 Found : C, 65.61; H, 9.13; N, 5.90; S, 2.24

Compound 16b: $[\alpha]_D^{22}$ −1.5° (C=0.55, in chloroform) Elemental Analysis for $C_{56}H_{103}N_5O_{12}S$: Calcd.: C, 62.83; H, 9.70; N, 6.54; S, 3.00 Found : C, 62.77; H, 9.92; N, 6.75; S, 2.94

Compound 16: $[\alpha]_D^{25}$ +19.2° (C=0.64 in 5% TFA-chloroform) Elemental Analysis for $C_{48}H_{87}N_5O_{12}S \cdot 1.5H_2O$: Calcd.: C, 58.51; H, 9.21; N, 6.87; S, 3.25 Found : C, 58.68; H, 9.00; N, 6.87; S, 3.25

Example 22

Production of (2R,6R)-2-amino-6,7-bis(PamO)-4-THT-Gly-Gly-D-Glu-OH (Compound 17)

In substantially the same manner as in Example 6, (2R,6R)-2-Fmoc-amino-6,7-bis(PamO)-4-THT-Gly-Gly-D-Glu (O$^t$Bu)-O$^t$Bu (17a), (2R,6R)-2-amino-6,7-bis(PamO)-4-THT-Gly-Gly-D-Glu(O$^t$Bu)-O$^t$Bu (17b) and (2R,6R)-2-amino- 6,7-bis(PamO)-4-THT-Gly-Gly-D-Glu-OH (Compound 17) were produced.

| Materials (g) | Reaction Conditions | Products (g) |
|---|---|---|
| a) GC-2 | P-9 | 780 mg 17a |

-continued

| Materials (g) | Reaction Conditions | Products (g) |
|---|---|---|
| (1.68) | HONB | 374 mg (1.97) |
| | DIC | 327 μl |
| | DMF | 18 ml |
| | 20° C. | 16 h |
| b) 17a | piperidine | 2.0 ml 17b |
| (1.80) | DCM | 18 ml (1.52) |
| | 20° C. | 1 h |
| | silica-gel | |
| | (chloroform-methanol) | |
| | 25:1 | |
| c) 17b | TFA | 10.0 ml 17 |
| (1.00) | 20° C. | 3 h (0.76) |

Compound 17a: $[\alpha]_D^{24} -10.0°$) (c=0.54, in chloroform) Elemental Analysis for $C_{70}H_{112}N_4O_{13}S$-.$0.5H_2O$: Calcd.: C, 66.79; H, 9.05; N, 4.45; S, 2.55 Found : C, 66.59; H, 8.75; N, 4.75; S, 2.53

Compound 17b: $[\alpha]_D^{24} -15.7°$ (C=0.49, in chloroform) Elemental Analysis for $C_{55}H_{102}N_4O_{11}S.0.5H_2O$: Calcd.: C, 63.73; H, 10.02; N, 5.41; S, 3.09 Found : C, 63.67; H, 10.23; N, 5.28; S, 3.07

Compound 17: $[\alpha]_D^{24} +6.0°$ (C=0.51, in 5% TFA-chloroform) Elemental Analysis for $C_{47}H_{86}N_4O_{11}S.2H_2O$: Calcd.: C, 59.34; H, 9.54; N, 5.89; S, 3.37 Found : C, 59.01; H, 9.17; N, 5.92; S, 3.08

Example 23

Production of (2R,6R)-2-amino-6,7-bis(PamO)-4-THT-Gly-Gly-OH (Compound 18)

In substantially the same manner as in Example 6, (2R,6R)-2-Fmoc-amino-6,7-bis(PamO)-4-THT-Gly-Gly-O$^t$Bu (18a), (2R,6R)-2-amino-6,7-bis(PamO)-4-THT-Gly-Gly-O$^t$Bu (18b) and (2R,6R)-2-amino-6,7-bis(PamO)-4-THT-Gly-Gly-OH (Compound 18) were produced.

| Materials (g) | Reaction Conditions | Products (g) |
|---|---|---|
| a GC-2 | H—Gly—Gly—O$^t$Bu | 580 mg 18a |
| (2.50) | HONB | 552 mg (2.42) |
| | DIC | 482 μl |
| | DMF | 20 ml |
| | 20° C. | 13 h |
| b) 18a | piperidine | 2.2 ml 18b |
| (2.20) | DCM | 22 ml (1.59) |
| | 20° C. | 1.5 h |
| | silica-gel | |
| | (chloroform-methanol) | |
| | 20:1 | |
| c) 18b | TFA | 6.0 ml 18 |
| (0.60) | 20° C. | 1 h (0.56) |

Compound 18a: $[\alpha]_D^{24} -7.6°$ (C=0.52 in chloroform) Elemental Analysis for $C_{61}H_{97}N_3O_{10}S$: Calcd.: C, 68.83; H, 9.18; N, 3.95; S, 3.01 Found : C, 69.06; H, 9.28; N, 4.09; S, 2.88

Compound 18b: $[\alpha]_D^{24} -13.4°$ (c=0.52, in chloroform) Elemental Analysis for $C_{46}H_{87}N_3O_8S.0.5H_2O$: Calcd.: C, 64.90; H, 10.42; N, 4.94; S, 3.77 Found : C, 64.99; H, 10.45; N, 4.82; S, 3.49

Compound 18: $[\alpha]_D^{25} +10.7°$ (c=0.51 in 5% TFA-chloroform) Elemental Analysis for $C_{42}H_{79}N_3O_8S.1.5H_2O$: Calcd.: C, 62.03; H, 10.16; N, 5.17; S, 3.94 Found : C, 61.80; H, 9.97; N, 4.85; S, 4.04

Example 24

Production of (2R,6R)-2-amino-6,7-bis(PamO)-4-THT-Gly-D-Glu-OH (Compound 19)

In substantially the same manner as in Example 6, (2R,6R)-2-Fmoc-amino-6,7-bis(PamO)-4-THT-Gly-D-Glu O$^t$Bu)-O$^t$Bu (19a), (2R,6R)-2-amino-6,7-bis(PamO)-4-THT-Gly-D-Glu (O$^t$Bu)-O$^t$Bu (19b) and (2R,6R)-2-amino-6,7-bis (PamO)-4-THT-Gly-D-Glu-OH (Compound 19) were produced.

| Materials (g) | Reaction Conditions | Products (g) |
|---|---|---|
| a) GC-2 | P-10 | 830 mg 19a |
| (2.12) | HONB | 471 mg (218) |
| | DIC | 412 μl |
| | DMF | 21 ml |
| | 20° C. | 16 h |
| b) 19a | piperidine | 2.0 ml 19b |
| (2.00) | DCM | 18 ml (1.72) |
| | 20° C. | 1 h |
| | silica-gel | |
| | (chloroform-methanol) | |
| | 97:3 | |
| c) 19b | TFA | 10 ml 19 |
| (1.00) | 20° C. | 3 h (0.70) |

Compound 19a: $[\alpha]_D^{24} -12.5°$ (c=0.55 in chloroform) Elemental Analysis for $C_{68}H_{109}N_3O_{12}S$: Calcd.: C, 68.43; H, 9.21; N, 3.52; S, 2.69 Found : C, 68.31; H, 9.25; N, 3.72; S, 2.48

Compound 19b: $[\alpha]_D^{24} -16.4°$ (c=0.53, in chloroform) Elemental Analysis for $C_{53}H_{99}N_3O_{10}S.0.8H_2O$: Calcd.: C, 64.64; H, 10.30; N, 4.27; S, 3.26 Found : C, 64.62; H, 10.25; N, 4.08; S, 3.22

Compound 19: $[\alpha]_D^{24} +14.2°$ (c=0.52 in 5% TFA-chloroform) Elemental Analysis for $C_{45}H_{83}N_3O_{10}S.2.2H_2O$: Calcd.: C, 60.19; H, 9.81; N, 4.68; S, 3.57 Found : C, 60.05; H, 9.44; N, 4.35; S, 3.61

Example 25

Production of (2R,6R)-2-amino-6,7-bis(PamO)-4-THT-D-Glu-OH (Compound 20)

In substantially the same manner as in Example 6, (2R,6R)-2-Fmoc-amino-6,7-bis(PamO)-4-THT-D-Glu(O$^t$Bu)-O$^t$Bu (20a), (2R,6R)-2-amino-6,7-bis(PamO)-4-THT-D-Glu (O$^t$Bu)-O$^t$Bu (20b) and (2R,6R)-2-amino-6,7-bis(PamO)-4-THT-D-Glu-OH (Compound 20) were produced.

| Materials (g) | Reaction Conditions | Products (g) |
|---|---|---|
| a) GC-2 | H-D-Glu(O$^t$Bu)-O$^t$Bu | 0.75 g | 20a |
| (2.35) | HONB | 518 mg | (2.35) |
| | DIC | 0.45 ml | |
| | DMF | 20 ml | |
| | 20° C. | 17 h | |
| b) 20a | piperidine | 2.0 ml | 20b |
| (2.23) | DCM | 20 ml | (1.76) |
| | 20° C. | | |
| | silica-gel | | |
| | (hexane-ethylacetate) | | |
| | 4:1, 3:2 | | |
| c) 20b | TFA | 10 ml | 20 |
| (0.77) | 20° C. | 2 h | (0.64) |

Compound 20a: $[\alpha]_D^{22}$ –7.4° (C=0.60 22 in chloroform) Elemental Analysis for $C_{66}H_{106}N_2O_{11}S$: Calcd.: C, 69.8.1; H, 9.41; N, 2.47; S, 2.82 Found : C, 69.66; H, 9.52; N, 2.85; S, 2.53

Compound 20b: $[\alpha]_D^{22}$ –15.9° (c=0.66, in chloroform) Elemental Analysis for $C_{51}H_{96}N_2O_9S \cdot 0.5H_2O$: Calcd.: C, 66.41; H, 10.60; N, 3.04; S, 3.48 Found : C, 66.42; H, 10.42; N, 3.25; S, 3.21

Compound 20: $[\alpha]_D^{25}$ –1.5° (c=0.55 in 5% TFA-chloroform) Elemental Analysis for $C_{43}H_{80}N_2O_9S$: Calcd.: C, 64.46; H, 10.06; N, 3.50; S, 4.00 Found: C, 64.56; H, 9.92; N, 3.42; S, 3.90

Example 26

Production of (2R,6R)-2-amino-6,7-bis(PamO)-4-THT-Asp-OH (Compound 21)

In substantially the same manner as in Example 6, (2R, 6R)-2-Fmoc-amino-6,7-bis(PamO)-4-THT-Asp(O$^t$Bu)-O$^t$Bu (21a), (2R,6R)-2-amino-6,7-bis(PamO)-4-THT-Asp(O$^t$Bu)-O$^t$Bu (21b) and (2R,6R)-2-amino-6,7-bis(PamO)-4-THT-Asp-OH (Compound 21) were produced.

| Materials (g) | | Reaction Conditions | | Products (g) |
|---|---|---|---|---|
| a) GC-2 | | H-Asp(O$^t$Bu)-O$^t$Bu | 0.69 g | 21a |
| (2.30) | | HONB | 507 mg | (2.67) |
| | | DIC | 0.44 ml | |
| | | DMF | 20 ml | |
| | | 20° C. | 17 h | |
| b) 21a | | piperidine | 2.5 ml | 21b |
| (2.56) | | DCM | 25 ml | (1.80) |
| | | 20° C. | 1 h | |
| | | silica-gel | | |
| | | (hexane-ethyl acetate) | | |
| | | 4:1, 3:2 | | |
| c) 21b | | TFA | 10 ml | 21 |
| (0.86) | | 20° C. | 2 h | (0.73) |

Compound 21a: $[\alpha]_D^{22}$ +5.20° (c=0.65 in chloroform) Elemental Analysis for $C_{65}H_{104}N_2O_{11}S$: Calcd.: C, 69.61; H, 9.35; N, 2.50; S, 2.86 Found : C, 69.38; H, 9.49; N, 2.77; S, 2.69

Compound 21b: $[\alpha]_D^{22}$ –1.1° (c=0.70, in chloroform) Elemental Analysis for $C_{50}H_{94}N_2O_9S$: Calcd.: C, 66.76; H, 10.54; N, 3.11; S, 3.57 Found : C, 66.87; H, 10.55; N, 3.36; S, 3.30

Compound 21: $[\alpha]_D^{25}$ +5.5° (C=0.63 in 5% TFA-chloroform) Elemental Analysis for $C_{42}H_{78}N_2O_9S$: Calcd.: C, 64.09; H, 9.99; N, 3.56; S, 4.07 Found : C, 64.23; H, 9.74; N, 3.44; S, 4.02

Example 27

Production of (2R,6R)-2-amino-6,7-bis(PamO)-4-THT-D-Asp-OH (Compound 22)

In substantially the same manner as in Example 6, (2R, 6R)-2-Fmoc-amino-6,7-bis(PamO)-4-THT-D-Asp(O$^t$Bu)-O$^t$Bu (22a), (2R,6R)-2-amino-6,7-bis(PamO)-4-THT-D-Asp(O$^t$Bu) O$^t$Bu (22b) and (2R,6R)-2-amino-6,7-bis(PamO)-4-THT-D-Asp-OH (Compound 22) were produced.

| Materials (g) | | Reaction Conditions | | Products (g) |
|---|---|---|---|---|
| a) GC-2 | | H-D-Asp(O$^t$Bu)-O$^t$Bu | 0.70 g | 22a |
| (2.32) | | HONB | 511 mg | (2.84) |
| | | DIC | 0.45 ml | |
| | | DMF | 20 ml | |
| | | 20° C. | 17 h | |
| b) 22a | | piperidine | 2.5 ml | 22b |
| (2.64) | | DCM | 25 ml | (1.87) |
| | | 20° C. | 1 h | |
| | | silica-gel | | |
| | | (hexane-ethylacetate) | | |
| | | 4:1, 3:2 | | |
| c) 22b | | TFA | 10 ml | 22 |
| (0.95) | | 20° C. | 2 h | (0.82) |

Compound 22a: $[\alpha]_D^{22}$ –12.7° (C=0.51 in chloroform) Elemental Analysis for $C_{65}H_{104}N_2O_{11}S$: Calcd.: C, 69.61; H, 9.35; N, 2.50; S, 2.86 Found : C, 69.82; H, 9.48; N, 2.98; S, 2.53

Compound 22b: $[\alpha]_D^{22}$ –22.7° (C=0.67, in chloroform) Elemental Analysis for $C_{50}H_{94}N_2O_9S \cdot 0.5H_2O$: Calcd.: C, 66.11; H, 10.54; N, 3.08; S, 3.53 Found : C, 65.83; H, 10.38; N, 2.93; S, 3.40

Compound 22: $[\alpha]_D^{25}$ –10.8° (C=0.62 in 5% TFA-chloroform) Elemental Analysis for $C_{42}H_{78}N_2O_9S$: Calcd.: C, 64.09; H, 9.99; N, 3.56; S, 4.07 Found : C, 64.13; H, 9.60; N, 3.47; S, 4.06

Example 28

Production of (2R,6R)-2-amino-6,7-bis(PamO)-4-THT-Gly-Glu-Glu-OH (Compound 23)

In substantially the same manner as in Example 6, (2R, 6R)-2-Fmoc-amino-6,7-bis(PamO)-4-THT-Gly-Glu(O$^t$Bu)-Glu(O$^t$Bu)-O$^t$Bu (23a), (2R,6R)-2-amino-6,7-bis(PamO)-4-THT-Gly-Glu (O$^t$Bu)-Glu(O$^t$Bu)-O$^t$Bu (23b) and (2R,6R)-2-amino-6,7-bis(PamO)-4-THT-Gly-Glu-Glu-OH (Compound 23) were produced.

| Materials (g) | | Reaction Conditions | | Products (g) |
|---|---|---|---|---|
| a) GC-2 | | P-11 | 590 mg | 23a |
| (0.95) | | HONB | 210 mg | (1.22) |
| | | DIC | 185 μl | |
| | | DMF | 9.5 ml | |
| | | 20° C. | 16 h | |
| b) 23a | | piperidine | 1.1 ml | 23b |
| (1.10) | | DCM | 9.9 ml | (0.97) |
| | | 20° C. | 1 h | |
| | | silica-gel | | |
| | | (chloroform-methanol) | | |
| | | 97:3 | | |
| c) 23b | | TFA | 4.8 ml | 23 |
| (0.48) | | 20° C. | 3 h | (0.36) |

Compound 23a: $[\alpha]_D^{24}$ –7.0° (C=0.50 in chloroform) Elemental Analysis for $C_{77}H_{124}N_4O_{15}S$: Calcd.: C, 67.12; H, 9.07; N, 4.07; S, 2.33 Found : C, 67.16; H, 9.05; N, 4.10; S, 2.40

Compound 23b: $[\alpha]_D^{24}$ –10.6° (c=0.50, in chloroform) Elemental Analysis for $C_{62}H_{114}N_4O_{13}S \cdot 0.5H_2O$: Calcd.: C, 63.94; H, 9.95; N, 4.81; S, 2.75 Found : C, 63.91; H, 9.80; N, 4.74; S, 2.71

Compound 23: $[\alpha]_D^{21}$ +13.0° (C=0.52 in 5% TFA-chloroform) Elemental Analysis for $C_{50}H_{90}N_4O_{13}S \cdot 1.5H_2O$: Calcd.: C, 59.20; H, 9.24; N, 5.52; S, 3.16 Found : C, 59.15; H, 9.09; N, 5.50; S, 3.41

Example 29

Production of (2R,6R)-2-amino-6,7-bis(PamO)-4-THT-Gly-Glu-D-Glu-OH (Compound 24)

In substantially the same manner as in Example 6, (2R,6R)-2-Fmoc-amino-6,7-bis(PamO)-4-THT-Gly-Glu(O$^t$Bu)-D-Glu (O$^t$Bu)-O$^t$Bu (24a), (2R,6R)-2-amino-6,7-bis(PamO)-4-THT-Gly-Glu(O$^t$Bu)-D-Glu(O$^t$Bu)-O$^t$Bu (24b) and (2R,6R)-2-amino-6,7-bis(PamO)-4-THT-Gly-Glu-D-Glu-OH (Compound 24) were produced.

| Materials (g) | Reaction Conditions | | Products (g) |
|---|---|---|---|
| a) GC-2 (0.81) | P-12 HONB DIC DMF 20° C. | 500 mg 178 mg 157 µl 8.0 ml 16 h | 24a (0.98) |
| b) 24a (0.90) | piperidine DCM 20° C. silica-gel (chloroform-methanol) 97:3 | 0.9 ml 8.1 ml 1 h | 24b (0.80) |
| c) 24b (0.40) | TFA 20° C. | 4.0 ml 3 h | 24 (0.29) |

Compound 24a: $[\alpha]_D^{24}$ –1.23° (C=0.52 in chloroform) Elemental Analysis for $C_{77}H_{124}N_4O_{15}S \cdot 0.5H_2O$: Calcd.: C, 66.68; H, 9.08; N, 4.04; S, 2.31 Found : C, 66.82; H, 8.83; N, 4.34; S, 2.33

Compound 24b: $[\alpha]_D^{24}$ –15.9° (c=0.49, in chloroform) Elemental Analysis for $C_{62}H_{114}N_4O_{13}S \cdot 0.5H_2O$: Calcd.: C, 63.94; H, 9.95; N, 4.81; S, 2.75 Found : C, 64.04; H, 9.84; N, 4.86; S, 2.76

Compound 24: $[\alpha]_D^{24}$ +5.0° (c=0.47 in 5% TFA-chloroform) Elemental Analysis for $C_{50}H_{90}N_4O_{13}S \cdot H_2O$: Calcd.: C, 59.73; H, 9.22; N, 5.57; S, 3.19 Found : C, 59.73; H, 9.25; N, 5.48; S, 3.18

Example 30

Production of (2R,6R)-2-amino-6,7-bis(PamO)-4-THT-Glu-Gly-Glu-OH (Compound 25)

In substantially the same manner as in Example 6, (2R,6R)-2-Fmoc-amino-6,7-bis(PamO)-4-THT-Glu(O$^t$Bu)-Gly-Glu (O$^t$Bu)-O$^t$Bu (25a), (2R,6R)-2-amino-6,7-bis(PamO)-4-THT-Glu (O$^t$Bu)-Gly-Glu(O$^t$Bu)-O$^t$Bu (25b) and (2R,6R)-2-amino- 6,7-bis(PamO)-4-THT-Glu-Gly-Glu-OH (Compound 25) were produced.

| Materials (g) | Reaction Conditions | | Products (g) |
|---|---|---|---|
| a) GC-2 (1.24) | P-13 HONB DIC DMF 20° C. | 770 mg 274 mg 241 µl 12.0 ml 16 h | 25a (1.63) |
| b) 25a (1.50) | piperidine DCM 20° C. silica-gel (chloroform-methanol) 97:3 | 1.5 ml 13.5 ml 1 h | 25b (1.34) |
| c) 25b (0.67) | TFA 20° C. | 6.7 ml 3 h | 25 (0.50) |

Compound 25a: $[\alpha]_D^{24}$ –1.7° (C=0.51 in chloroform) Elemental Analysis for $C_{77}H_{124}N_4O_{15}S$: Calcd.: C, 67.12; H, 9.07; N, 4.07; S, 2.33 Found : C, 66.97; H, 9.12; N, 4.06; S, 2.25

Compound 25b: $[\alpha]_D^{24}$ –9.6° (C=0.53, in chloroform) Elemental Analysis for $C_{62}H_{114}N_4O_{13}S \cdot H_2O$: Calcd.: C, 63.45; H, 9.96; N, 4.77; S, 2.73 Found : C, 63.31; H, 9.81; N, 4.82; S, 2.65

Compound 25: $[\alpha]_D^{24}$ +8.7° (c=0.52 in 5% TFA-chloroform) Elemental Analysis for $C_{50}H_{90}N_4O_{13}S \cdot 1.5H_2O$: Calcd.: C, 59.20; H, 9.24; N, 5.52; S, 3.16 Found : C, 59.34; H, 9.13; N, 5.53; S, 3.21

Example 31

Production of (2R,6R)-2-amino-6,7-bis(PamO)-4-THT-Glu-Glu-OH (Compound 26)

In substantially the same manner as in Example 6, (2R,6R)-2-Fmoc-amino-6,7-bis(PamO)-4-THT-Glu(O$^t$Bu)-Glu (O$^t$Bu)-O$^t$Bu (26a), (2R,6R)-2-amino-6,7-bis(PamO)-4-THT-Glu (O$^t$Bu)-Glu(O$^t$Bu)-O$^t$Bu (26b) and (2R,6R)-2-amino-6,7-bis(PamO)-4-THT-Glu-Glu-OH (Compound 26) were produced.

| Materials (g) | Reaction Conditions | | Products (g) |
|---|---|---|---|
| a) GC-2 (1.20) | H-Glu(O$^t$Bu)-Glu(O$^t$Bu)-O$^t$Bu HONB DIC DMF 20° C. | 660 mg 265 mg 233 µl 12.0 ml 16 h | 26a (1.63) |
| b) 26a (1.50) | piperidine DCM 20° C. silica-gel (chloroform-methanol) 97:3 | 1.5 ml 13.5 ml 1 h | 26b (1.32) |
| c) 26b (0.66) | TFA 20° C. | 6.6 ml 3 h | 26 (0.47) |

Compound 26a: $[\alpha]_D^{24}$ –7.4° (C=0.51 in chloroform) Elemental Analysis for $C_{75}H_{121}N_3O_{14}S$: Calcd.: C, 68.20; H, 9.23; N, 3.18; S, 2.43 Found : C, 68.26; H, 9.09; N, 2.95; S, 2.57

Compound 26b: $[\alpha]_D^{24}$ –17.7° (c=0.53, in chloroform) Elemental Analysis for $C_{60}H_{111}N_3O_{12}S \cdot 0.5H_2O$: Calcd.: C, 65.06; H, 10.19; N, 3.79; S, 2.89 Found : C, 64.88; H, 10.29; N, 3.81; S, 2.95

Compound 26: $[\alpha]_D^{24}$ –0.9° (c=0.52 in 5% TFA-chloroform) Elemental Analysis for $C_{48}H_{87}N_3O_{12}S \cdot H_2O$: Calcd.: C, 60.79; H, 9.46; N, 4.43; S, 3.38 Found: C, 60.89; H, 9.40; N, 4.41; S, 3.38

Example 32

Production of (2R,6R)-2-amino-6,7-bis(PamO)-4-THT-Glu-D-Glu-OH (Compound 27)

In substantially the same manner as in Example 6, (2R, 6R)-2-Fmoc-amino-6,7-bis(PamO)-4-THT-Glu(O$^t$Bu)-D-Glu (O$^t$Bu)-O$^t$Bu (27a), (2R,6R)-2-amino-6,7-bis(PamO)-4-THT-Glu (O$^t$Bu)-D-Glu(O$^t$Bu)-O$^t$(27b) and (2R,6R)-2-amino- 6,7-bis(PamO)-4-THT-Glu-D-Glu-OH (Compound 27) were produced.

| Materials (g) | Reaction Conditions | | Products (g) |
|---|---|---|---|
| a) GC-2 (1.27) | P-14 HONB DIC DMF 20° C. | 700 mg 282 mg 247 µl 12.7 ml 16 h | 27a (1.45) |
| b) 27a (1.33) | piperidine DCM 20° C. silica-gel (chloroform-methanol) 97:3 | 1.4 ml 12.6 ml 1 h | 27b (1.12) |
| c) 27b (0.55) | TFA 20° C. | 5.5 ml 3 h | 27 (0.45) |

Compound 27a: $[\alpha]_D^{24}$ –12.6° (C=0.52 in chloroform) Elemental Analysis for C$_{75}$H$_{121}$N$_3$O$_{14}$S: Calcd.: C, 68.20; H, 9.23; N, 3.18; S, 2.43 Found : C, 68.27; H, 9.46; N, 3.14; S, 2.30

Compound 27b: $[\alpha]_D^{24}$ –21.3° (C=0.51, in chloroform) Elemental Analysis for C$_{60}$H$_{111}$N$_3$O$_{12}$S.0.5H$_2$O: Calcd.: C, 65.06; H, 10.19; N, 3.79; S, 2.89 Found : C, 65.05; H, 10.33; N, 3.65; S, 2.88

Compound 27: $[\alpha]_D^{24}$ –5.9° (c=0.53 in 5% TFA-chloroform) Elemental Analysis for C$_{48}$H$_{87}$N$_3$O$_{12}$S.H$_2$O: Calcd.: C, 60.79; H, 9.46; N, 4.43; S, 3.38 Found : C, 60.88; H, 9.25; N, 4.43; S, 3.19

Example 33

Production of (2R,6R)-2-amino-6,7-bis(PamO)-4-THT-Glu-Glu-Glu-OH (Compound 28)

In substantially the same manner as in Example 6, (2R, 6R)-2-Fmoc-amino-6,7-bis(PamO)-4-THT-Glu(O$^t$Bu)-Glu (O$^t$Bu)-Glu(O$^t$Bu)-O$^t$Bu (28a), (2R,6R)-2-amino-6,7-bis (PamO)-4-THT-Glu(O$^t$Bu)-Glu(O$^t$Bu)-Glu(O$^t$Bu)-O$^t$Bu (28b) and (2R,6R)-2-amino-6,7-bis(PamO)-4-THT-Glu-Glu-Glu-OH (Compound 28) were produced.

| Materials (g) | Reaction Conditions | | Products (g) |
|---|---|---|---|
| a) GC-2 (0.91) | P-15 HONB DIC DMF 20° C. | 715 mg 201 mg 177 µl 9.1 ml 16 h | 28a (1.48) |
| b) 28a (1.35) | piperidine DCM 20° C. silica-gel (chloroform-methanol) 97:3 | 1.3 ml 11.7 ml 1 h | 28b (1.20) |
| c) 28b (0.60) | TFA 20° C. | 6.0 ml 3 h | 28 (0.44) |

Compound 28a: $[\alpha]_D^{24}$ –13.2° (c=0.52 in chloroform) Elemental Analysis for C$_{84}$H$_{136}$N$_4$O$_{17}$S: Calcd.: C, 66.99; H, 9.10; N, 3.72; S, 2.18 Found : C, 67.08; H, 9.14; N, 3.78; S, 2.16

Compound 28b: $[\alpha]_D^{24}$ –19.5° (c=0.53, in chloroform) Compound 28b: Elemental Analysis for C$_{69}$H$_{126}$N$_4$O$_{15}$S.0.5H$_2$O: Calcd.: C, 64.10; H, 9.90; N, 4.33; S, 2.48 Found : C, 64.28; H, 9.92; N, 4.21; S, 2.47

Compound 28: $[\alpha]_D^{24}$ –5.1° (C=0.53 in 5% TFA-chloroform) Elemental Analysis for C$_{53}$H$_{94}$N$_4$O$_{15}$S.0.5H$_2$O: Calcd.: C, 59.58; H, 8.96; N, 5.24; S, 3.00 Found : C, 59.36; H, 8.91; N, 5.20; S, 2.95

Example 34

Production of (2R,6R)-2-amino-6,7-bis(PamO)-4-THT-Glu-Glu-D-Glu-OH (Compound 29)

In substantially the same manner as in Example 6, (2R, 6R)-2-Fmoc-amino-6,7-bis(PamO)-4-THT-Glu(O$^t$Bu)-Glu (O$^t$Bu)-D-Glu(O$^t$Bu)-O$^t$Bu (29a), (2R,6R)-2-amino-6,7-bis (PamO)-4-THT-Glu(O$^t$Bu)-Glu(O$^t$Bu)-D-Glu(O$^t$Bu)-O$^t$Bu (29b) and (2R, 6R)-2-amino-6,7-bis (PamO)-4-THT-Glu-Glu-D-Glu-OH (Compound 29) were produced.

| Materials (g) | Reaction Conditions | | Products (g) |
|---|---|---|---|
| a) GC-2 (0.75) | P-16 HONB DIC DMF 20° C. | 590 mg 166 mg 146 µl 7.5 ml 16 h | 29a (1.27) |
| b) 29a (1.15) | piperidine DCM 20° C. silica-gel (chloroform-methanol) 97:3 | 1.2 ml 10.8 ml 1 h | 29b (0.99) |
| c) 29b (0.50) | TFA 20° C. | 5.0 ml 3 h | 29 (0.36) |

Compound 29a: $[\alpha]_D^{24}$ –12.7° (C=0.49 in chloroform) Elemental Analysis for C$_{84}$H$_{136}$N$_4$O$_{17}$S: Calcd.: C, 66.99; H, 9.10; N, 3.72; S, 2.13 Found : C, 66.80; H, 9.15; N, 3.65; S, 2.15

Compound 29b: $[\alpha]_D^{24}$ –20.7° (C=0.51, in chloroform) Elemental Analysis for C$_{69}$H$_{126}$N$_4$O$_{15}$S.H$_2$O: Calcd.: C, 63.66; H, 9.91; N, 4.30; S, 2.46 Found : C, 63.67; H, 9.88; N, 4.26; S, 2.48

Compound 29: $[\alpha]_D^{24}$ –16° (C=0.52 in 5% TFA-chloroform) Elemental Analysis for C$_{53}$H$_{94}$N$_4$O$_{15}$S.H$_2$O: Calcd.: C, 59.08; H, 8.98; N, 5.20; S, 2.98 Found : C, 58.85; H, 8.90; N, 5.17; S, 2.81

Example 35

Production of (2R,6R)-2-Fmoc-amino-6-hydroxy-7-PamO-4-THT-O$^t$Bu (GC-5a), (2R,6R)-2-Fmoc-amino-6-hexanoyloxy- 7-PamO-4-THT-O$^t$Bu (GC-5b) and (2R,6R)-2-Fmoc-amino-6-hexanoyloxy-7-PamO-4-THT-OH (GC-5)

In substantially the same manner as in Example 2, (2R, 6R)-2-Fmoc-amino-6-hydroxy-7-PamO-4-THT-O$^t$Bu (GC-5a), (2R,6R)-2-Fmoc-amino-6-hexanoyloxy-7-PamO-4-THT-O$^t$Bu (GC-5b) and (2R,6R)-2-Fmoc-amino-6-hexanoyloxy-7-PamO-4-THT-OH (GC-5) were prepared.

| Materials (g) | Reaction Conditions | | Products (g) |
|---|---|---|---|
| a) (Fmoc-(R)-Cys-O$^t$Bu)$_2$ (3.83) | 1) zinc acid mixt. soln. DCM 20° C. 30 min 2) (S)-O-palmitoylglycidol supplemented 50° C. | 1.25 g 13 ml 25 ml 12.0 g 8 h | GC-5a (5.07) |
| b) GC-5a (4.80) | hexanoic acid DIC | 1.96 g 2.64 ml | GC-5b (5.23) |

-continued

| Materials (g) | Reaction Conditions | | Products (g) |
|---|---|---|---|
| | DMAP | 329 mg | |
| | THF | 90 ml | |
| | 20° C. | 17 h | |
| c) GC-5b | TFA | 20 ml | GC-5 |
| (5.08) | 20° C. | 1.5 h | (4.72) |

Compound GC-5a: m.p. 57.5°–58.8° C. $[\alpha]_D^{20}$ –2.9° (C=0.55 in chloroform) Elemental Analysis for $C_{41}H_{61}NO_7S$: Calcd.: C, 69.16; H, 8.64; N, 1.97; S, 4.50 Found : C, 68.95; H, 8.67; N, 1.83; S, 4.48

Compound GC-5b: $[\alpha]_D^{20}$+1.1° (C=0.52, in chloroform) Elemental Analysis for $C_{47}H_{71}NO_8S$: Calcd.: C, 69.68; H, 8.83; N, 1.73; S, 3.96 Found : C, 69.78; H, 8.90; N, 1.78; S, 3.80

Compound GC-5: $[\alpha]_D^{20}$+14.0° (C=0.56 in chloroform) Elemental Analysis for $C_{43}H_{63}NO_8S$: Calcd.: C, 68.49; H, 8.42; N, 1.86; S, 4.25 Found : C, 68.27; H, 8.34; N, 1.83; S, 4.26

Example 36

Production of (2R,6R)-2-amino-6-hexanoyloxy-7-PamO-4-THT-Gly-Gly-Gly-Glu-OH (Compound 30)

In substantially the same manner as in Example 6, (2R, 6R)-2-Fmoc-amino-6-hexanoyloxy-7-PamO-4-THT-Gly-Gly-Gly-Glu (O$^t$Bu)-O$^t$Bu (30a), (2R,6R)-2-amino-6-hexanoyloxy- 7-PamO-4-THT-Gly-Gly-Gly-Glu(O$^t$Bu)-O$^t$Bu (30b) and (2R,6R)-2-amino-6-hexanoyloxy-7-PamO-4-THT-Gly-Gly-Gly-Glu-OH (Compound 30) were produced.

| Materials (g) | Reaction Conditions | | Products (g) |
|---|---|---|---|
| a) GC-5 | P-4 | 1.88 g | 30a |
| (3.00) | HONB | 784 mg | (3.32) |
| | DIC | 0.69 ml | |
| | DMF | 25 ml | |
| | 20° C. | 16 h | |
| b) 30a | piperidine | 3.0 ml | 30b |
| (3.20) | DCM | 30 ml | (2.26) |
| | 20° C. | 2 h | |
| | silica-gel | | |
| | (chloroform-methanol) | | |
| | 50:1, 20:1 | | |
| c) 30b | TFA | 5 ml | 30 |
| (0.53) | 20° C. | 2 h | (0.46) |

Compound 30a: $[\alpha]_D^{22}$–6.4° (c=0.53 in chloroform) Elemental Analysis for $C_{62}H_{95}N_5O_{14}S$: Calcd.: C, 63.84; H, 8.21; N, 6.00; S, 2.75 Found : C, 63.67; H, 8.09; N, 5.89; S, 2.84

Compound 30b: $[\alpha]_D^{22}$–8.2° (c=0.56, in chloroform) Elemental Analysis for $C_{47}H_{85}N_5O_{12}S$: Calcd.: C, 59.78; H, 9.07; N, 7.42; S, 3.40 Found : C, 59.64; H, 8.87; N, 7.42; S, 3.37

Compound 30: $[\alpha]_D^{22}$+9.5° (=0.57 in 5% TFA-chloroform) Elemental Analysis for $C_{39}H_{69}N_5O_{12}S \cdot 1.5H_2O$: Calcd.: C, 54.53; H, 8.45; N, 8.15; S, 3.73 Found : C, 54.56; H, 8.09; N, 8.21; S, 3.69

Example 37

Production of (2R,6R)-2-Fmoc-amino-6,7-bis(PamO)-4-THT-Glu-Gly-D-Glu-OH (Compound 31)

The compound 11a (600 mg) was dissolved in TFA (6.0 ml), and the solution was left standing for 2 hours at 20° C. The reaction mixture was concentrated, and the concentrate was suspended in acetonitrile. The suspension was subjected to filtration to collect the compound 31 as a white powdery product (517 mg, yield 98%).

$[\alpha]_D^{25}$–16.5° (c=0.58, in 5% TFA-chloroform) Elemental Analysis for $C_{65}H_{100}N_4O_{15}S \cdot H_2O$: Calcd.: C, 63.60; H, 8.38; N, 4.56; S, 2.61 Found : C, 63.83; H, 8.47; N, 4.46; S, 2.52

Example 38

Production of (2R, 6R)-2-acetylamino-6,7-bis (PamO)-4-THT-Glu-Gly-D-Glu-OH (Compound 32)

Starting from the compound 11b, (2R,6R)-2-acetylamino-6,7-bis (PamO)-4-THT-Glu-Gly-D-Glu-OH (Compound 32) was produced via (2R, 6R)-2-acetylamino- 6,7-bis(PamO)-4-THT-Glu(O$^t$Bu)-Gly-D-Glu(O$^t$Bu)-O$^t$Bu (32a).

a) The compound 11b (700 mg) was dissolved in DCM (7.0 ml ), to which was added acetic anhydride (86 μl), and the mixture was stirred for one hour at 20° C. The reaction mixture was concentrated. The concentrate was suspended in acetonitrile. The suspension was subjected to filtration to collect the compound 32a as a white powdery product (580 mg).

$[\alpha]_D^{24}$–12.8° (c=0.49, in chloroform) Elemental Analysis for $C_{64}H_{116}N_4O_{14}S \cdot 0.5H_2O$: Calcd.: C, 63.70; H, 9.77; N, 4.64; S, 2.66 Found: C, 63.80; H, 9.79; N, 4.54; S, 2.55 b) A TFA solution (5.3 ml) of the compound 32a (530 mg) was processed in substantially the same manner as in the deprotection reaction in Example 37 to give the compound 32 as a white powdery product (455 mg).

$[\alpha]_D^{25}$–16.6° (C=0.52, in 5% TFA-chloroform) Elemental Analysis for $C_{52}H_{92}N_4O_{14}S \cdot H_2O$: Calcd.: C, 59.63; H, 9.05; N, 5.35; S, 3.06 Found : C, 59.59; H, 8.99; N, 5.15; S, 2.91

Example 39

Production of(2R,6R)-2-hexanoylamino-6-hexanoyloxy-7-PamO-4-THT-Gly-Gly-Gly-Glu-OH (Compound 33)

Starting from the compound 30b, (2R,6R)-2-hexanoylamino-6-hexanoyloxy-7-PamO-4-THT-Gly-Gly-Gly-Glu-OH (Compound 33) was produced via (2R,6R)-2-hexanoylamino- 6-hexanoyloxy-7-PamO-4-THT-Gly-Gly-Gly-Glu(O$^t$Bu)-O$^t$Bu (33a).

a) The compound 30b (550 mg) was dissolved in DCM (10 ml). To the solution were added, under ice-cooling, HOBT (87 mg), WSC (123 mg) and hexanoic acid (80 μl). The mixture was stirred for 18 hours at 20° C. The reaction mixture was concentrated, and the concentrate was dissolved in ethyl acetate, followed by washing with a 10% aqueous solution of ammonium chloride, a 2% aqueous solution of sodium hydrogencarbonate and water, successively. The ethyl acetate layer was dried over anhydrous sodium sulfate, which was then concentrate. The concentrate was suspended in acetonitrile, and the suspension was subjected to filtration to collect (2R,6R)-2-hexanoylamino-6-hexanoyloxy-7-PamO-4-THT-Gly-Gly-Gly-Glu (O$^t$Bu)-O$^t$Bu (33a) as a white powdery product (534 mg, yield 88%).

The compound 33a: $[\alpha]_D^{22}$ −8.0° (C=0.56, in chloroform) Elemental Analysis for $C_{53}H_{95}N_5O_{13}S$: Calcd.: C, 61.07; H, 9.19; N, 6.72; S, 3.08 Found : C, 61.02; H, 9.10; N, 6.71; S, 3.05 b) The compound 33a (480 mg) was dissolved in TFA (5.0 ml), and the solution was stirred for 2 hours at 20° C. The reaction mixture was concentrated, and the concentrate was suspended in acetonitrile. The suspension was subjected to filtration to collect the compound 33 (408 mg, yield 95%).

The compound 33: $[\alpha]_D^{22}$ −12.7° (c=0.64, in 5% TFA-chloroform) Elemental Analysis for $C_{45}H_{79}N_5O_{13}S \cdot 0.5H_2O$: Calcd.: C, 57.55; H, 8.59; N, 7.46; S, 3.41 Found : C, 57.74; H, 8.54; N, 7.41; S, 3.43

Example 40

Production of (2R,6R)-2-Fmoc-amino-6,7-bis(SteO)-4-THT-O$^t$Bu (GC-6a), and (2R,6R)-2-Fmoc-amino-6,7-bis(SteO)-4-THT-OH (GC-6)

In substantially the same manner as in Example 2, (2R, 6R)-2-Fmoc-amino-6,7-bis(SteO)-4-THT-O$^t$Bu (GC-6a), and (2R,6R)-2-Fmoc-amino-6,7-bis(SteO)-4-THT-OH (GC-6) were produced.

| Materials | Reaction Conditions | | Products |
|---|---|---|---|
| a) GC-2a (2.65 g) | Stearic acid DIC DMAP THF 20° C. | 5.58 g 3.07 ml 275 mg 45 ml 14 h | GC-6a (3.20 g) |
| b) GC-6a (3.00 g) | TFA 20° C. | 15 ml 2.0 h | GC-6 (2.75 g) |

Compound GC-6a: m.p. 64.2°–65.9° C. $[\alpha]_D^{24}$+0.2° (c=0.92, in chloroform) Elemental Analysis for $C_{61}H_{99}NO_8S$: Calcd.: C, 72.79; H, 9.91; N, 1.39; S, 3.19 Found : C, 72.60, H, 10.10; N, 1.66; S, 3.37

Compound GC-6: m.p. 92.0°–92.8° C. $[\alpha]_D^{24}$+11.0° (c=0.67, in chloroform) Elemental Analysis for $C_{57}H_{91}NO_8S$: Calcd.: C, 72.03; H, 9.65; N, 1.47; S, 3.37 Found : C, 72.21; H, 10.05; N, 1.57; S, 3.24

Example 41

Production of (2R,6R)-2-Fmoc-amino-6,7-bis(MyrO)-4-THT-O$^t$Bu (GC-7a) and (2R,6R)-2-Fmoc-amino-6,7-bis(MyrO)-4-THT-OH (GC-7)

In substantially the same manner as in Example 2, (2R, 6R)-2-Fmoc-amino-6,7-bis(MyrO)-4-THT-O$^t$Bu (GC-7a) and (2R,6R)-2-Fmoc-amino-6,7-bis(MyrO)-4-THT-OH (GC-7) were produced.

| Materials | Reaction Conditions | | Products |
|---|---|---|---|
| a) GC-2a (2.50 g) | myristic acid DIC DMAP THF 20° C. | 4.22 g 2.89 ml 258 mg 45 ml 14 h | GC-7a (2.58 g) |
| b) GC-7a (3.00 g) | TFA 20° C. | 20 ml 2.0 h | GC-7 (1.93 g) |

Compound GC-7a: m.p. 49.2°–50.9° C. $[\alpha]_D^{22}$+0.5° (c=0.83, in chloroform) Elemental Analysis for $C_{53}H_{83}NO_8S$: Calcd.: C, 71.18; H, 9.35; N, 1.57; S, 3.59 Found : C, 70.97, H, 9.24; N, 1.62, S, 3.52

Compound GC-7: m.p. 82.8°–83.5° C. $[\alpha]_D^{22}$+12.7° (c=0.58, in chloroform) Elemental Analysis for $C_{49}H_{75}NO_8S \cdot 0.25H_2O$: Calcd.: C, 69.84; H, 9.03; N, 1.66; S, 3.81 Found: C, 69.85, H, 9.09; N, 1.62, S, 3.78

Example 42

Production of (2R,6R)-2-amino-6,7-bis(SteO)-4-THT-Gly-Glu-Glu-OH (Compound 34)

In substantially the same manner as in Example 6, (2R, 6R)-2-Fmoc-amino-6,7-bis(SteO)-4-THT-Gly-Glu(O$^t$Bu)-Glu (O$^t$Bu)-O$^t$Bu (34a), (2R,6R)-2-amino-6,7-bis(SteO)-4-THT-Gly-Glu (O$^t$Bu)-Glu(O$^t$Bu)-O$^t$Bu(34b) and (2R,6R)-2-amino-6,7-bis(SteO)-4-THT-Gly-Glu-Glu-OH (Compound 34) were produced.

| Materials | Reaction Conditions | | Products |
|---|---|---|---|
| a) GC-6 (2.53 g) | P-11 HONB DIC DMF 20° C. | 1.47 g 525 mg 459 µl 20 ml 16 h | 34a (3.75 g) |
| b) 34a (3.56 g) | piperidine DCM 20° C. silica-gel (chroloform-methanol) 20:1 | 3.6 ml 30 ml 2.0 h | 34b (2.78 g) |
| c) 34b (0.59 g) | TFA 20° C. | 6.0 ml 2.0 h | 34 (0.51 g) |

Compound 34a: $[\alpha]_D^{24}$−6.6° (c=0.62, in chloroform) Elemental Analysis for $C_{81}H_{132}N_4O_{15}S$: Calcd.: C, 67.84; H, 9.28; N, 3.91; S, 2.24 Found : C, 67.59, H, 9.54; N, 4.27; S, 2.46

Compound 34b: $[\alpha]_D^{24}$−10.7° (C=0.75, in chloroform) Elemental Analysis for $C_{66}H_{122}N_4O_{13}S \cdot H_2O$: Calcd.: C, 64.46; H, 10.16; N, 4.56; S, 2.61 Found : C, 64.46, H, 10.07; N, 4.83, S, 2.64

Compound 34: $[\alpha]_D^{24}$+10.8° (C=0.65, 5% in TFA-chloroform) Elemental Analysis for $C_{54}H_{98}N_4O_{13}S \cdot 4H_2O$: Calcd.: C, 58.14; H, 9.58; N, 5.02; S, 2.87 Found : C, 58.48, H, 9.20; N, 5.20, S, 2.72

Example 43

Production of (2R,6R)-2-amino-6,7-bis(MyrO)-4-THT-Gly-Glu-Glu-OH (Compound 35)

In substantially the same manner as in Example 6, (2R, 6R)-2-Fmoc-amino-6,7-bis(MyrO)-4-THT-Gly-Glu(O$^t$Bu)-Glu (O$^t$Bu)-O$^t$Bu (35a), (2R,6R)-2-amino-6,7-bis(MyrO)-4-THT-Gly-Glu (O$^t$Bu)-Glu(O$^t$Bu)-O$^t$Bu (35b) and (2R,6R)-2-amino- 6,7-bis(MyrO)-4-THT-Gly-Glu-Glu-OH (Compound 35) were produced.

| Materials | Reaction Conditions | | Products |
|---|---|---|---|
| a) GC-7 (1.83 g) | P-11 HONB DIC DMF 20° C. | 1.21 g 432 mg 378 µg 20 ml 18 h | 35a (2.22 g) |
| b) 35a (2.10 g) | piperidine DCM 20° C. silica-gel (chroloform- | 3.6 ml 30 ml 2.0 h | 35b (1.58 g) |

|   | Materials | Reaction Conditions | Products |
|---|---|---|---|
|   |   | methanol) 20:1 |   |
| c) 35b | | TFA | 10 ml | 35 |
| (1.00 g) | | 20° C. | 2.0 h | (0.85 g) |

Compound 35a: $[\alpha]_D^{22}$ –7.6° (c=0.71, in chloroform) Elemental Analysis for $C_{73}H_{116}N_4O_{15}S$: Calcd.: C, 66.33; H, 8.85; N, 4.24; S, 2.43 Found : C, 66.30, H, 8.97; N, 4.38; S, 2.42

Compound 35b: $[\alpha]_D^{22}$ –12.0° (c=1.11, in chloroform) Elemental Analysis for $C_{58}H_{106}N_4O_{13}S$: Calcd.: C, 63.36; H, 9.02; N, 5.10; S, 2.92 Found : C, 63.14, H, 9.69; N, 5.21, S, 2.81

Compound 35: $[\alpha]_D^{22}$ +10.9° (c=0.86, in 5% TFA-chloroform) Elemental Analysis for $C_{46}H_{82}N_4O_{13}S4H_2O$: Calcd.: C, 55.07; H, 9.04; N, 5.58; S, 3.20 Found : C, 54.96, H, 9.12; N, 5.25, S, 2.94

Example 44

Production of (2R,6R)-2-amino-6,7-bis(PamO)-4-THT-NH(CH$_2$)$_7$CO-Glu-OH hydrochloride (Compound 36)

a) To a solution of GC-2 (179 mg) synthesized in Example 3 and P-17 (80 mg) synthesized in Reference Example 17 in DMF (4 ml) were added TEA (0.033 ml) and DEPC (49 mg). The mixture was stirred for 90 minutes at 20° C. To the reaction mixture was added water, which was subjected to extraction with ethyl acetate. The extract solution was washed with a 5% aqueous solution of citric acid, a saturated aqueous solution of sodium hydrogencarbonate and a saturated aqueous saline solution, followed by drying over anhydrous sodium sulfate. The solvent was distilled off, and the residue was purified by means of a silica gel column chromatography (hexane:ethyl acetate=1:1) to give (2R, 6R)-2-Fmoc-amino-6,7-bis(PamO)-4-THT-NH(CH$_2$)$_7$CO-Glu (O$^t$Bu)-O$^t$Bu (36a) (105 mg, yield 41%) as a colorless waxy compound.

IR (KBr) v: 3300, 1730, 1685, 1660, 1645 cm$^{-1}$ $^1$H-NMR (CDCl$_3$) δ:0.88 (6H,t,J=7.0 Hz), 1.03–1.38 (56H,m), 1.44 (9H,s), 1.47 (9H,s), 1.49–2.40 (12H,m), 2.79 (2H,d,J=5.2 Hz), 2.93 (2H,d,J=7.0 Hz), 3.17–3.32 (2H,m), 4.00–4.56 (7H,m), 5.17–5.32 (1H,m), 5.78–5.90 (1H,m), 6.19 (1H,d, J=8.0 Hz), 6.44–6.56 (1H,m), 7.26–7.46 (4H,m), 7.61 (2H, d,J=7.4 Hz), 7.78 (2H,d,J=7.4 Hz)

b) To the compound 36a (104 mg) obtained thus above was added piperidine (2 ml), and the mixture was stirred for 30 minutes at room temperature. The reaction mixture was then concentrated. The concentrate was purified by means of a silica gel column chroamtography (hexane:ethyl acetate= 1.1~ chloroform:methanol=19:1) to give (2R,6R)-2-amino-6,7-bis (PamO)-4-THT-NH(CH$_2$)$_7$CO-Glu(O$^t$Bu)-O$^t$Bu (36b) (80 mg, yield 93%) as a colorless waxy compound.

IR (KBr) v: 3320, 1735, 1650 cm$^{-1}$ $^1$H-NMR (CDCl$_3$) δ: 0.88 (6H,t,J=6.8 Hz), 1.03–1.38 (52H,m), 1.44 (9H,s), 1.47 (9H,s), 1.49–2.43 (12H,m), 2.20 (2H,t,H=7.8 Hz), 2.31 (2H,t,J=7.8 Hz), 2.33 (2H,t,J=7.4 Hz) , 2.72 (1H,dd,J=8.8, 13.6 Hz), 2.75 (2H,d,J=6.0 Hz), 3.12 (1H,dd,J=3.8, 13.6 Hz), 3.15–3,29 (2H,m), 3.48 (1H,dd,J=3.8, 8.8 Hz), 4.14 (1H,dd,J=6.0, 11.8 Hz), 4.35 (1H,dd,J=3.6, 11.8 Hz), 4.41–4.55 (1H,m), 5.09–5.22 (1H,m), 6.15 (1H,d,J=8.0 Hz)), 7.40 (1H,t,J=5.8 Hz).

c) To the compound 36b (80 mg) obtained as above was added a 4N HCl ethyl acetate solution (4 ml), which was stirred for 4 hours at 20° C. The solvent was distilled off to give (2R,6R)-2-amino-6,7-bis(PamO)-4-THT-NH(CH 2)$_7$CO-Glu-OH hydrochloride (36) (74 mg, yield 100%) as a white powdery product, m.p. 53°–56° C.

$[\alpha]_D^{23}$+6.0° (c=0.50, in chloroform); Elemental Analysis for $C_{52}H_{89}N_4O_{11}SC1:2.H_2O$: Calcd.: C, 59.49; H, 8.93; N, 5.34; S, 3.05 Found : C, 59.62, H, 8.77; N, 5.37, S, 3.14 IR (KBr) v: 3250, 1740, 1715, 1640 cm$^{-1}$ $^1$H-NMR (CDCl$_3$) δ: 0.88 (6H,t,J=6.8 Hz), 1.03–1.50 (56H,m), 1.50–1.80 (6H, m), 1.80–3.55 (16H,m), 4.03–4.70 (4H,m), 5.10–5.35 (1H, m)

Example 45

Production of (2R,6R)-2-amino-6,7-bis(PamO)-4-THT-NH (CH$_2$)$_{11}$CO-Glu-OH hydrochloride (Compound 37)

In substantially the same manner as in Example 44, (2R,6R)-2-Fmoc-amino-6,7-bis(PamO)-4-THT-NH(CH²)$_{11}$CO-Glu(O $^t$Bu)-O$^t$Bu (37a), (2R,6R)-2-amino-6, 7-bis(PamO)-4-THT-NH (CH$_2$)$_{11}$CO-Glu(O$^t$Bu)-O$^t$Bu (37b) and (2R,6R)-2-amino- 6,7-bis(PamO)-4-THT-NH(CH$_2$)$_{11}$CO-Glu-OH hydrochloride (Compound 37) were produced.

|   | Materials | Reaction Conditions | Products |
|---|---|---|---|
| a) GC-2 (179 mg) | P-18 91 mg DEPC 49 mg TEA 33 μl DMF 4 ml 20° C. 90 min | | 37a (52 mg) |
| b) 37a (104 mg) | piperidine 2 ml 20° C. 30 min | | 37b (31 mg) |
| c) 37b (31 mg) | 4N HCl ethyl acetate 4 ml 20° C. 4.0 h | | 37 (29 mg) |

Compound 37a: IR (KBr) v: 3280, 1730, 1685, 1645 cm$^{-1}$ ıH-NMR (CDCl$_3$) δ: 0.88 (6H,t,J=7.0 Hz), 0.95–1.38 (64H, m), 1.44 (9H,s), 1.47 (9H,s), 1.50–2.40 (12H,m), 2.79 (2H,d,J=5.2 Hz), 2.86–2.96 (1H,m), 3.18–3.32 (2H,m), 4.08–4.55 (6H,m), 5.18–5.33 (1H,m), 5.73–5.85 (1H,m), 6.14 (1H,d,J=7.8 Hz), 6.40–6.53 (1H,m), 7.25– 7.45 (4H,m), 7.61 (2H,d,J=7.4 Hz), 7.78 (2H,d,J=7.0 Hz)

Compound 37b: IR (KBr) v: 3360, 3310, 1730, 1650 cm$^{-1}$ ıH-NMR (CDCl$_3$) δ: 0.88 (6H,t,J=6.4 Hz), 1.03–1.39 (56H, m), 1.44 (9H,s), 1.47 (9H,s), 1.52–1.72 (12H,m), 1.72–2.43 (2H,m), 2.20 (2H,t,J=8.0 Hz), 2.31 (2H,t,J=7.8 Hz), 2.33 (2H,t,J=7.6 Hz), 2.73 (1H,dd,J=8.7, 13.0 Hz), 2.75 (2H,d, J=7.4 Hz), 3.11 (1H,dd,J=3.7, 13.0 Hz), 3.23 (2H,dt,J=7.4, 7.4 Hz), 3.48 (1H,dd,J=3.7, 8.7 Hz), 4.14 (1H,dd,J=6.2, 12.0 Hz), 4.35 (1H,dd,J=3.2, 2.0 Hz), 4.42–4.56 (1H,m), 5.08–5.22 (1H,m), 6.15 (1H,d,J=7.8 Hz), 7.39 (1H,t,J=7.4 Hz)

Compound 37: m.p. 61°–64° C. $[\alpha]_D^{23}$+4.2° (c=0.50, in chloroform); Elemental Analysis for $C_{55}H_{104}N_3O_{10}SC1.2H_2O$: Calcd.: C, 61.68; H, 10.16; N, 3.92; S, 2.99 Found : C, 62.02, H, 9.33; N, 3.73, S, 2.64 IR (KBr) v: 3250, 1740, 1720, 1640 cm$^{-1}$ $^1$H-NMR (CDCl$_3$) δ: 0.88 (6H,t,J=6.8 Hz), 1.03–1.50 (64H,m), 1.50–1.80 (6H, m), 1.80–3.55 (16H,m), 4.03–4.70 (4H,m), 5.10–5.35 (1H, m)

Example 46

Production of (2R,6R)-4-(2-amino-6,7-bis(PamO)-4-THT-amino) benzoyl-Glu-OH hydrochloride (Compound 38)

a) To a solution of the compound P-19 (85 mg) in pyridine (1.5 ml) was added phosphorus trichloride (0.01 ml). The mixture was stirred for 2 hours at 20° C., to which was added the compound GC-2 (100 mg), followed by stirring for 3 hours at 20° C. To the reaction mixture was added water, which was subjected to extraction with ethyl acetate. The extract was washed with a 5% aqueous solution of citric acid, a saturated aqueous solution of sodium hydrogencarbonate and a saturated aqueous saline solution, followed by drying over anhydrous sodium sulfate. The solvent was the distilled off, and the residue was purified by means of a silica gel column chromatography (chloroform:hexane=7:1) to give (2R,6R)-4-(2-Fmoc-amino- 6,7-bis(PamO)-4-THT-amino)benzoyl-Glu(O$^t$Bu)-O$^t$Bu (38a) (107 mg, yield 84%) as a colorless waxy compound.

IR (KBr) ν: 3300, 1730, 1685, 1660, 1640, 1600 cm$^{-1}$ $^1$H-NMR (CDCl$_3$) δ: 0.88 (6H,t,J=7.0 Hz), 1.10–1.38 (48H, m), 1.42 (9H,s), 1.49 (9H,s), 1.55–1.83 (4H,m), 1.90–2.58 (8H,m), 2.75–2.86 (2H,m), 3.02 (2H,d,J=6.6 Hz), 4.21–4.72 (8H,m), 5.24–5.49 (1H,m), 5.74–5.86 (1H,m), 7.01 (2H,d, J=7.6 Hz), 7.32 (2H,d,J=7.6 Hz), 7.35–7.87 (8H,m), 8.70 (1H,br s)

b) To the compound 38a (107 mg) obtained as above was added piperidine (2 ml). The mixture was stirred for 3 hours at 20° C., then the reaction mixture was concentrated. The concentrate was purified by means of a silica gel column chromatography (hexane:ethyl acete=1:7) to give (2R, 6R)-4-(2-amino-6,7-bis(PamO)-4-THT-amino) benzoyl-Glu-(O$^t$Bu)-O$^t$Bu (38b) (66 mg, yield 68%) as a colorless waxy product IR (KBr) ν: 3430, 3380, 1735, 1640 cm$^{-1}$ $^1$H-NMR (CDCl$_3$) δ:0.88 (6H,t,J=6.6 Hz), 1.05–1.37 (48H,m), 1.42 (9H,s), 1.49 (9H,s), 1.52–1.82 (4H,m), 1.93–2.53 (8H,m), 2.70–4.00 (5H,m), 4.05–4.72 (3H,m), 5.10–5.24 (1H,m), 7.23–7.95 (4H,m), 9.71 (1H,br s)

c) To the compound 38b (66 mg) obtained as above was added 4N HCl ethyl acetate solution (3 ml), which was stirred for 4 hours at 20° C. The solvent was distilled off to give compound 38 (61 mg, yield 100%) as a colorless powdery product, m.p. 94.0°–96.0° C. [α]$_D^{23}$+6.2° (c=0.50, in chloroform); Elemental Analysis for C$_{50}$H$_{86}$N$_3$O$_{10}$SC1.2H$_2$O: Calcd.: C, 60.49; H, 9.14; N, 4.23; S, 3.23 Found : C, 60.39, H, 8.98; N, 4.19, S, 3.18 IR (KBr) ν: 3400, 1750, 1630, 1610 cm$^{-1}$ $^1$H-NMR (CDCl$_3$) δ:0.88 (6H,t,J=6.8Hz), 1.02–1.48 (48H,m), 1.48–1.68 (4H,m), 2.00–2.85 (13H,m), 4.05–5.32 (4H,m), 7.40–8.00 (4H,m)

Example 47

Production of (2R,6R)-4-(2-amino-6,7-bis(PamO)-4-THT-Gly-amino) benzoyl-Glu-OH hydrochloride (Compound 39)

In substantially the same manner as in Example 44, (2R,6R)-4-(2-Fmoc-amino-6,7-bis(PamO)-4-THT-Gly-amino) benzoyl-Glu(O$^t$Bu)-O$^t$Bu (39a), (2R,6R)-4-(2-amino- 6,7-bis(PamO)-4-THT-Gly-amino)benzoyl-Glu-(O$^t$Bu)-O$^t$Bu (39b) and (2R,6R)-4-(2-amino-6,7-bis(PamO)-4-THT-Gly-amino) benzoyl-Glu-OH hydrochloride (Compound 39) were produced.

| Materials | Reaction Conditions | | Products |
|---|---|---|---|
| a) GC-2 (179 mg) | P-20 DEPC TEA DMF 20° C. | 87 mg 49 mg 33 μl 4 ml 90 min | 39a (146 mg) |
| b) 39a (146 mg) | piperidine 20° C. | 3 ml 4.5 h | 39b (87 mg) |
| c) 39b (87 mg) | 4N HCl ethyl acetate 20° C. | 4 ml 4.0 h | 39 (78 mg) |

Compound 39a: IR (KBr) ν: 3300, 1735, 1730, 1700, 1655, 1640 cm$^{-1}$ $^1$H-NMR (CDCl$_3$) δ: :0.88 (6H,t,J=6.6 Hz), 1.02–1.84 (64H,m), 1.42 (9H,s), 1.49 (9H,s), 1.84–3.15 (13H,m), 4.00–4.73 (9H, m), 5.15–5.28 (1H,m), 5.80–5.92 (1H,m), 6.92–7.13 (2H, m), 7.26–7.83 (12H,m), 8.53 (1H,br s)

Compound 39b: IR (KBr) ν: 3350, 1735, 1650, 1600 cm$^{-1}$ $^1$H-NMR (CDCl$_3$) δ: 0.88 (6H,t,J=7.0 Hz), 1.52–1.76 (4H, m), 1.95–2.53 (8H,m), 2.75 (2H,d,J=6.6 Hz), 2.92 (1H,dd, J=7.8, 13.6 Hz), 3.11 (1H,dd,J=4.2, 13.6 Hz), 3.66 (1H,dd, J=4.2, 7.8 Hz), 4.01–4.24 (3H,m), 4.37 (1H,dd,J=3.4, 11.8 Hz), 4.57–4.62 (1H,m), 5.08–5.22 (1H,m), 7.00 (1H,d,J=7.6 Hz), 7.59 (2H,d,J=8.8 Hz), 7.79 (2H,d,J=8.8 Hz), 8.19 (1H,t,J=5.6 Hz), 8.63 (1H,s)

Compound 39: m.p. 100°–101° C. IR (KBr) ν: 3400, 1735 cm$^{-1}$ Elemental Analysis for C$_{51}$H$_{96}$N$_3$O$_{10}$SC1.H$_2$O: Calcd.: C, 61.44; H, 9.91; N, 4.41; S, 3.22 Found : C, 61.17, H, 9.81; N, 4.26, S, 3.21 $^1$H-NMR (CDCl$_3$) δ: :0.88 (6H,t, J=6.8 Hz), 0.93–1.47 (48H,m), 1.47–1.70 (4H,m), 1.70–3.32 (16H,m), 3.70–4.60 (4H,m), 4.60–4.78 (1H,m), 5.17–5.32 (1H,m), 7.47–7.90 (4H,m)

Example 48

Production of (2R,6R)-2-amino-6,7-bis(PamO)-4-THT-NH(CH$_2$)$_5$CO-Glu-OH TFA salt (Compound 40)

In substantially the same manner as in Example 44, (2R,6R)-2-Fmoc-amino-6,7-bis(PamO)-4-THT-NH(CH$_2$)$_5$CO-Glu(O$^t$Bu)-O$^t$Bu (40a) was synthesized. Then, (2R,6R)-2-amino-6,7-bis(PamO)-4-THT-NH(CH$_2$)$_5$CO-Glu(O$^t$Bu)-O$^t$Bu (40b) and (2R,6R)-2-amino-6,7-bis(PamO)-4-THT-NH(CH$_2$)$_5$CO-Glu-OH TFA salt (Compound 40) were produced.

| Materials | Reaction Conditions | | Products |
|---|---|---|---|
| a) GC-2 (150 mg) | P-21 DEPC TEA DMF 0° C. | 64 mg 35 mg 44 mg 3 ml 1 h | 40a (112 mg) |

Compound 40a: $^1$H-NMR (CDCl$_3$) δ: 0.878 (6H,t,J=6.0 Hz), 1.247 (52H,s), 1.433 (9H,s), 1.463 (9H,s), 1.465–1.720 (6H,m), 1.72–2.15 (2H,m), 2.15–2.40 (16H,m), 2.785 (2H, d,J=5.8 Hz), 2.927 (2H,d,J=6.2 Hz), 3.265 (2H,m), 4.05–4.55 (7H ,m), 5.232 (1H,br s), 5.825 (1H,d,J=8.2 Hz) 6.236 (1H,d,J=8.2 Hz), 6.595 (1H,br s), 7.366 (4H,m), 7.600 (2H,d,J=7.0 Hz), 7.766 (2H,d,J=7.0 Hz) IR (neat) ν: 3300, 2920, 2850, 1735, 1650, 1530, 1440, 1370, 1255, 1245, 1225, 1155 cm$^{-1}$ b) The compound 40a (112 mg) was dissolved in DCM (0.2 ml). To the solution was added piperidine (2 ml), and the mixture was stirred for 2 hours at 20° C. The reaction mixture was concentrated under reduced pressure. The concentrate was allowed to be adsorbed on a silica gel column (5 g) processed with ammonia. Elution was conducted with chloroform to give the compound 40b as a colorless oily product (83 mg, yield 89.8%), ¹H-NMR (CDCl₃) δ: 0.878 (6H,t,J=6.0 Hz), 1.254 (52H, s), 1.467 (9H,s), 1.499 (9H,s), 1.47–1.75 (6H,m), 1.72–2.15 (2H,m), 2.15–2.40 (10H,m), 2.60–2.80 (3H,m), 3.107 (1H, dd,J=3.8 Hz,13.6 Hz), 3.242 (2H,q,J=6.2 Hz), 3.475 (1H, dd,J=4.0 Hz,6.8 Hz), 4.142 (1H,dd,J=6.0 Hz,12.0 Hz), 4.358 (1H,dd,J=3.4 Hz, 11.8 Hz), 4.472 (2H,m), 5.154 (1H,m), 6.90 (1H,d,J=7.6 Hz), 7.424 (1H,t,J=7.2 Hz) IR (neat) ν: 3300, 2920, 2850, 1735, 1650, 1530, 1440, 1370, 1255, 1245, 1225, 1155 cm⁻¹ c) The compound 40b (83 mg) was dissolved in DCM (0.2 ml). To the solution was added TFA (1 ml), and the mixture was stirred for 2 hours at 20° C. To the reaction mixture was added toluene (1 ml), and the mixture was concentrated under reduced pressure. This process was repeated again to give the compound 40 as a white powdery product (83 mg, yield 100%), m.p. 62°–63° C.

$[\alpha]_D^{23}$+3.4° (c=0.16, in chloroform); ¹H-NMR (CDCl₃-TFA) δ: 0.879 (6H,t,J=6.6 Hz), 1.256 (52H,s), 1.567 (6H,m), 1.90–2.20 (2H,m), 2.374 (8H,m), 2.597 (2H,t,J=6.4 Hz), 2.744 (2H,d,J=7.0 Hz), 3.100 (2H,m), 4.130 (1H,dd,J=6.0 Hz,12.0 Hz), 4.28–4.50 (2H,m), 4.650 (1H,m), 5.170 (1H, m), 7.080 (1H,d,J=7.5 Hz), 7.420 (1H,br s) IR (KBr) ν: 3320, 3100, 2920, 2850, 1740, 1665, 1550, 1465, 1200 cm⁻¹ Elemental Analysis for $C_{51}H_{92}N_3O_{12}SF_3 \cdot H_2O$: Calcd.: C, 58.54; H, 9.05; N, 4.02; S, 3.06 Found : C, 58.35, H, 8.91; N, 4.06, S, 2.76

Example 49

Production of (2R,6R)-2-amino-6,7-bis(PamO)-4-THT-NH(CH₂)₆NHCO-Glu-OH TFA salt (Compound 41)

In substantially the same procedure as in Example 48, (2R,6R)-2-Fmoc-amino-6,7-bis(PamO)-4-THT-NH(CH₂)₆NHCO-Glu(O'Bu)-O'Bu (41a), (2R,6R)-2-amino-6,7-bis (PamO)-4-THT-NH(CH₂)₆NHCO-Glu-(O'Bu)-O'Bu (41b), and (2R,6R)-2-amino-6,7-bis(PamO)-4-THT-NH(CH₂)₆NHCO-Glu-OH TFA salt (Compound 41) were produced.

| Materials | Reaction Conditions | | Products |
|---|---|---|---|
| a) GC-2 | P-22 | 83 mg | 41a |
| (150 mg) | DEPC | 35 mg | (203 mg) |
| | TEA | 44 mg | |
| | DMF | 3 ml | |
| | 0° C. | 1 h | |
| b) 41a | piperidine | 2 ml | 41b |
| (203 mg) | DCM | 0.2 ml | (137 mg) |
| | 20° C. | 1.5 h | |
| c) 41b | TFA | 1 ml | 41 |
| (137 mg) | 20° C. | 2 h | (136 mg) |

Compound 41a: ¹H-NMR (CDCl₃) δ: 0.879 (6H,t,J=7.0 Hz), 1.254 (52H,s), 1.430 (9H,s), 1.448 (9H,s), 1.727 (8H, m), 1.75–2.20 (2H,m), 2.325 (6H,m), 2.780 (2H,d,J=5.0 Hz), 2.944 (2H,d,J=5.2 Hz), 3.05–3.50 (4H,m), 4.00–4.50 (9H,m), 4.860 (1H,t,J=6.0 Hz), 5.249 (2H,d,J=8.2 Hz), 6.08 (1H,br s), 6.710 (1H,br s), 7.260–7.55 (4H,m), 7.612 (2H, d,J=8.0 Hz), 7.767 (2H,d,J=8.0 Hz) IR (neat) ν: 3300, 2920, 2850, 1730, 1685, 1640, 1560, 1550, 1530, 1460, 1445, 1360, 1250, 1150, 1100, 1030 cm⁻¹

Compound 41b: ¹H-NMR (CDCl₃) δ: 0.879 (6H,t,J=6.2 Hz), 1.254 (52H,s), 1.439 (9H,s), 1.461 (9H,s), 1.597 (8H, m), 1.75–2.20 (2H,m), 2.311 (6H,m), 2.745 (2H,m), 3.00–3.45 (4H,m), 3.483 (1H,m), 4.136 (1H,dd,J=6.4 Hz,12.4 Hz), 4.353 (2H,m), 4.700 (1H,t,J=5.2 Hz), 5.078 (1H,d,J=7.6 Hz), 5.162 (1H,br s), 7.440 (1H,br s) IR (neat) ν: 3350, 2920, 2850, 1730, 1640, 1560, 1460, 1450, 1390, 1360, 1250, 1260, 1150, 1100, 750, 730 cm⁻¹

Compound 41: m.p. 44°–46° C. $[\alpha]_D^{23}$–2.9° (c=0.415, in chloroform); ¹H-NMR (CDCl₃) δ: 0.880 (6H,t,J=6.2 Hz), 1.255 (52H,s), 1.591 (8H,m), 2.0–2.20 (2H,m), 2.302 (6H, m), 2,779 (2H,m), 3.00–3.45 (3H,m), 3.516 (2H,m), 3.80–4.25 (6H,m), 4.340 (2H,m), 5.200 (1H,br s), 7.57 (1H,br s), 7.710 (1H,br s) IR (KBr) ν: 3400, 2920, 2850, 1740(sh.), 1700, 1670(sh.), 1460, 1420, 1280, 1260, 1240, 1200, 1175, 1130 cm⁻¹ Elemental Analysis for $C_{50}H_{95}N_4O_{12}SF_3$: Calcd.: C, 58.11; H, 9.27; N, 5.42; S, 3.10 Found : C, 58.19, H, 8.77; N, 5.24, S, 2.78

Example 50

Production of (2R,6R)-4-(2-amino-6,7-bis(PamO)-4-THT-aminomethyl)benzoyl-Glu-OH hydrochloride (Compound 42)

In substantially the same manner as in Example 44, (2R,6R)-4-(2-Fmoc-amino-6,7-bis(PamO)-4-THT-aminomethyl)benzoyl-Glu(O'Bu)-O'Bu (42a), (2R,6R)-4-(2-amino-6,7-bis (PamO)-4-THT-aminomethyl)benzoyl-Glu-(O'Bu)-O'Bu (42b) and (2R,6R)-4-(2-amino-6,7-bis(PamO)-4-THT-aminomethyl)benzoyl-Glu-OH hydrochloride (Compound 42) were produced.

| Materials | Reaction Conditions | | Products |
|---|---|---|---|
| a) GC-2 | P-23 | 106 mg | 42a |
| (200 mg) | DEPC | 55 mg | (247 mg) |
| | TEA | 70 mg | |
| | DMF | 10 ml | |
| | 20° C. | 30 min | |
| b) 42a | piperidine | 2 ml | 42b |
| (243 mg) | DCM | 0.5 ml | (195 mg) |
| | 20° C. | 30 min | |
| c) 42b | 4N HCl ethyl acetate | 4 ml | 42 |
| (112 mg) | 20° C. | 2 h | (88 mg) |

Compound 42a: IR (neat) ν: 3300, 2920, 2850, 1730, 1660, 1530, 1500, 1445, 1360, 1240, 1150 cm⁻¹ ¹H-NMR (CDCl₃) δ: 0.88 (6H,t,J=6.8 Hz), 1.25 (48H,s), 1.42 (9H,s), 1.49 (9H,s), 1.40–1.65 (4H,m), 1.95–2.50 (8H,m), 2.77 (2H,d,J=6.6 Hz), 2.90–3.00 (2H,m), 4.05–4.55 (8H,m), 4.66 (1H,m), 5.24 (1H,m), 5.78 (1H,br), 6.98 (1H,br), 7.02 (1H, d,J=7.4 Hz), 7.25–7.45 (6H,m), 7.58 (2H,d,J=7.4 Hz), 7.76 (2H,d,J=7.2 Hz), 7.78 (2H,d,J=8.4 Hz)

Compound 42b: IR (neat) ν: 3350, 2920, 2850, 1730, 1650, 1535, 1520, 1500, 1460, 1450, 1360, 1250, 1150 cm⁻¹ ¹H-NMR (CDCl₃) δ: 0.88 (6H,t,J=6.8 Hz), 1.25 (48H,s), 1.42 (9H,s), 1.49 (9H,s), 1.45–1.65 (4H,m), 1.73 (2H,br s), 1.90–2.50 (8H,m), 2.75 (2H,d,J=6.4 Hz), 2.81 (1H,dd,J=13.4, 8.4 Hz), 3.14 (1H,dd,J=13.4,3.8 Hz), 3.57 (1H,dd,J=8.4,4.0 Hz), 4.14 (1H,dd,J=12.0,6.2 Hz), 4.36 (1H,dd,J=12.0,3.2 Hz), 4.49 (2H,d,J=6.2 Hz), 4.66 (1H,m), 5.16 (1H,m), 7.02 (1H,d,J=7.4 Hz), 7.35 (2H,d,J=8.2 Hz), 7.79 (2H,d,J=8.2 Hz), 7.83 (1H,br)

Compound 42: m.p. 79°–80° C. $[\alpha]_D^{20}$+15.1° (c=0.305, in chloroform); IR (KBr) ν: 3450, 2920, 2850, 1730, 1710, 1690, 1670, 1640, 1630, 1620, 1560, 1540, 1500, 1460 cm⁻¹ ¹H-NMR (CDCl₃-TFA) δ: 0.88 (6H,t,J=6.8 Hz), 1.25 (48H, s), 1.40–1.65 (4H,m), 2.00–3.30 (12H,m), 4.00–4.80 (6H, m), 5.22 (1H,m), 7.00–8.10 (6H,m). Elemental Analysis for $C_{51}H_{87}N_3O_{10}S \cdot HCl \cdot H_2O$: Calcd.: C, 61.95; H, 9.17; N, 4.25; S, 3.24, Cl, 3.59 Found: C, 61.66, H, 8.93; N, 4.24, S, 3.44, Cl, 3.79

Example 51

Production of (2R,6R)-4-(N-(2-Fmoc-amino-6,7-bis-(PamO)-4-THT)-N-(carboxymethyl)aminomethyl)benzoyl-Glu-OH (Compound 43)

In substantially the same manner as in Example 44, (2R,6R)-4-(N-(2-Fmoc-amino-6,7-bis(PamO)-4-THT)-N-(t-butyloxycarbonylmethyl)aminomethyl)benzoyl-Glu(O$^t$-Bu)O$^t$Bu (43a), and (2R,6R)-4-(N-(2-Fmoc-amino-6,7-bis-(PamO)-4-THT)-N-(carboxymethyl)aminomethyl)benzoyl-Glu-OH (Compound 43) were produced.

| Materials | Reaction Conditions | | Products |
|---|---|---|---|
| a) GC-2 (100 mg) | P-24 DEPC TEA DMF 20° C. | 62 mg 30 mg 48 mg 6 ml 1 h | 43a (134 mg) |
| b) 43a (110 mg) | TFA DCM 20° C. | 1 ml 0.5 ml | 43 (70 mg) |

Compound 43a: IR (neat) ν: 2920, 2850, 1730, 1650, 1360, 1250, 1150 cm$^{-1}$ $^1$H-NMR (CDCl$_3$) δ: 0.88 (6H,t,J=6.8 Hz), 1.25 (48H,s), 1.40 (1/2×9H,s), 1.42 (9H,s), 1.44 (1/2×9H,s), 1.49 (9H,s), 1.45–1.70 (4H,m), 2.00–2.50 (8H, m), 2.65–3.20 (4H,m), 3.70–4.50 (8H,m), 4.60–4.80 (3H, m), 5.17 (1H,m), 5.70–5.80 (1H,m), 7.00–7.10 (1H,m), 7.25–7.45 (6H,m), 7.61 (2H,d,J=7.4 Hz), 7.75–7.90 (4H,m)

Compound 43: m.p. 58°–59° C. $[α]_D^{20}$ –12.6° (c=0.25, in chloroform); IR (KBr) ν: 2921, 2852, 1739, 1640, 1540, 1465, 1450, 1250, 1220, 1160 cm$^{-1}$ $^1$H-NMR (CDCl$_3$) δ: 0.87 (6H,t,J=6.6 Hz), 1.25 (48H,s), 1.40–1.70 (4H,m), 2.00–2.50 (8H,m), 2.60–3.00 (4H,m), 3.90–4.50 (8H,m), 5.17 (1H,m), 6.27 (1H,m), 7.15–7.45 (6H,m), 7.50–7.85 (6H,m) Elemental Analysis for C$_{68}$H$_{100}$N$_3$O$_{14}$S.H$_2$O: Calcd.: C, 66.21; H, 8.33; N, 3.41; S, 2.60 Found : C, 66.44, H, 8.32; N, 3.21, S, 2.66

Example 52

Production of (2R,6R)-2-amino-6,7-bis(PamO)-4-THT-Gly-Lys-Gly-OH 2 TFA salt (compound 44)

In substantially the same manner as in Example 6, (2R, 6R)-2-Fmoc-amino-6,7-bis(PamO)-4-THT-Gly-Lys(Boc)-Gly-O$^t$Bu (44a), (2R,6R)-2-amino-6,7-bis(PamO)-4-THT-Gly-Lys(Boc)-Gly-O$^t$Bu (44b) and (2R,6R)-2-amino-6,7-bis (PamO)-4-THT-Gly-Lys-Gly-OH 2 TFA salt (compound 44) were produced.

| Materials (g) | Reaction Conditions | | Products (g) |
|---|---|---|---|
| a) GC-2 (1.97) | P-25 HONB DIC DMF 20° C. | 1.01 mg 435 mg 380 μl 30 ml 13 h | 44a (2.24) |
| b) 44a (2.00) | piperidine DCM 20° C. silica-gel (chloroform-methanol) 50:1 | 2.0 ml 20 ml 2 h | 44b (1.23) |
| c) 44b (0.25) | TFA 20° C. | 6.0 ml 2 h | 44 (0.23) |

Compound 44a: $[α]_D^{25}$ –10.0° (c=0.66 in chloroform) Elemental Analysis for C$_{72}$H$_{117}$N$_5$O$_{13}$S: Calcd.: C, 66.89; H, 9.12; N, 5.42; S, 2.48 Found : C, 67.10; H, 9.37; N, 5.18; S, 2.49

Compound 44b: $[α]_D^{25}$ –15.2° (c=0.56 in chloroform) Elemental Analysis for C$_{57}$H$_{107}$N$_5$O$_{11}$S: Calcd.: C, 63.95; H, 10.07; N, 6.54; S, 3.00 Found : C, 63.70; H, 10.20; N, 6.50; S, 2.99

Compound 44: $[α]_D^{25}$ +5.5° (c=0.62 in 5% TFA-chloroform) Elemental Analysis for C$_{48}$H$_{91}$N$_5$O$_9$S.2TFA: Calcd.: C, 54.67; H, 8.21; N, 6.13; S, 2.81 Found : C, 54.29; H, 8.19; N, 6.47; S, 3.06

Example 53

Preparation of sodium salt

1) Compound 12 (5.0 g) was dissolved in 20% (v/v) acetonitrile-0.5% (w/v) sodium hydrogen carbonate aqueous solution (5 L) at 40° C. After adjusting pH of the solution at 9.5, the solution was subjected to a chromatography on Diaion HP-20 (1.0 L, Mitsubishi Kasei Corp. Japan) which was previously swollen with 20% (v/v) aqueous acetonitrile. The resin was washed with 20% (v/v) aqueous acetonitrile (5 L), followed by development with 40% (v/v) aqueous acetonitrile (4 L) and 60% (v/v) aqueous acetonitrile (5 L). Eluate was concentrated and then freeze-dried to give a powdery product. The powdery product was suspended in acetone (150 ml). Insolubles were collected by filtration to give disodium salt of compound 12 (4.5 g) as a white powder.

FAB-Mass spectrum (M+H)=959 Elemental Analysis for C$_{47}$H$_{84}$N$_4$O$_{11}$SNa$_2$.3H$_2$O: Calcd.: C, 55.71; H, 8.95; N, 5.53; S, 3.16; Na, 4.54 Found : C, 55.90; H, 9.39; N, 5.34; S, 3.16; Na, 4.78

2) Compound 19 (11.0 g) was dissolved in 15% (v/v) acetonitrile-0.5% (w/v) sodium hydrogen carbonate aqueous solution (5 L) at 40° C. After adjusting pH of the solution at 9.5, the solution was subjected to a chromatography on Diaion HP-20 (1.0 L, Mitsubishi Kasei Corp. Japan) which was previously swollen with 15% (v/v) aqueous acetonitrile. The resin was washed with 15% (v/v) aqueous acetonitrile (5 L), followed by development with 40% (v/v) aqueous acetonitrile (12 L). Eluate was concentrated and then freeze-dried to give a powdery product. The powdery product was suspended in acetone (200 ml). Insolubles were collected by filtration to give disodium salt of compound 23 (9.9 g) as a white powder.

FAB-Mass spectrum (M+H)=902 Elemental Analysis for C$_{45}$H$_{81}$N$_3$O$_{10}$SNa$_2$.3H$_2$O: Calcd.: C, 56.52; H, 9.17; N, 4.39; S, 3.35; Na, 4.81 Found : C, 56.61; H, 9.14; N, 4.26; S, 3.35; Na, 5.25

3) Compound 23 (14.0 g) was dissolved in 5% (v/v) acetonitrile-0.5% (w/v) sodium hydrogen carbonate aqueous solution (7 L) at 40° C. After adjusting pH of the solution at 9.5, the solution was subjected to a chromatography on Diaion HP-20 (1.4 L, Mitsubishi Kasei Corp. Japan) which was previously swollen with 5% (v/v) aqueous acetonitrile. The resin was washed with 5% (v/v) aqueous acetonitrile (7 L), followed by development with 40% (v/v) aqueous acetonitrile (8.5 L). Eluate was concentrated and then freeze-dried to give a powdery product. The powdery product was suspended in acetone (600 ml). Insolubles were collected by filtration to give trisodium salt of compound 23 (11.5 g) as a white powder.

FAB-Mass spectrum (M+H)=1053 Elemental Analysis for C$_{50}$H$_{87}$N$_4$O$_{13}$SNa$_3$.4H$_2$O: Calcd.: C, 53.37; H, 8.51; N, 4.98; S, 2.85; Na, 6.13 Found : C, 53.48; H, 8.81; N, 4.89; S, 3.03; Na, 6.0

4) Compound 25 (8.0 g) was dissolved in 5% (v/v) acetonitrile-0.5% (w/v) sodium hydrogen carbonate aqueous solution (4 L) at 40° C. After adjusting pH of the solution at 9.5, the solution was subjected to a chromatography on Diaion HP-20 (1.5 L, Mitsubishi Kasei Corp. Japan) which was previously swollen with 5% (v/v) aqueous acetonitrile. The resin was washed with 5% (v/v) aqueous acetonitrile (7.5 L), followed by development with 40% (v/v) aqueous acetonitrile (6 L). Eluate was concentrated and then freeze-dried to give a powdery product. The powdery product was suspended in acetone (200 ml). Insolubles were collected by filtration to give trisodium salt of compound 25 (7.0 g) as a white powder.

FAB-Mass spectrum (M+H)=1053 Elemental Analysis for $C_{50}H_{87}N_4O_{13}SNa_3 \cdot 2.5H_2O$: Calcd.: C, 54.68; H, 8.44; N, 5.10; S, 2.92; Na, 6.28 Found : C, 54.48; H, 8.64; N, 5.09; S, 2.79; Na, 6.13

5) Compound 7 (200 mg) was dissolved in 30% (v/v) methanol-0.5% (w/v) sodium hydrogen carbonate aqueous solution (300 ml) at 40° C. After adjusting pH of the solution at 9.5, the solution was subjected to a chromatography on Diaion HP-20 (50 ml, Mitsubishi Kasei Corp. Japan) which was previously swollen with 30% (v/v) aqueous methanol. The resin was washed with 30% (v/v) aqueous methanol (200 ml) and 50% (v/v) aqueous methanol (200 ml), followed by development with 80% (v/v) aqueous methanol (600 ml). Eluate was concentrated and then freeze-dried to give a powdery product. The powdery product was suspended in acetone (8 ml). Insolubles were collected by filtration to give disodium salt of compound 7 (75 mg) as a white powder.

Elemental Analysis for $C_{49}H_{87}N_5O_{12}SNa_2 \cdot 2.5H_2O$: Calcd.: C, 55.45; H, 8.74; N, 6.60; S, 3.02 Found : C, 55.47; H, 8.55; N, 6.48; S, 3.11

Structural formulae of the compounds obtained in the above examples are shown in Table 1.

TABLE 1

| Compound No. | Example No. | Structural Formulae |
|---|---|---|
| 1 | 6 | (2R,6S)-2-amino-6,7-bis(PamO)-4-THT-Gly—Gly—Gly—Glu—Thr—Thr—OH |
| 2 | 7 | (2R,6R)-2-amino-6,7-bis(PamO)-4-THT-Gly—Gly—Gly—Glu—Thr—Thr—OH |
| 3 | 8 | (2S,6R)-2-amino-6,7-bis(PamO)-4-THT-Gly—Gly—Gly—Glu—Thr—Thr—OH |
| 4 | 9 | (2S,6S)-2-amino-6,7-bis(PamO)-4-THT-Gly—Gly—Gly—Glu—Thr—Thr—OH |
| 5 | 10 | (2R,6R)-2-amino-6,7-bis(PamO)-4-THT-Gly—Gly—Gly—Glu—Thr—OH |
| 6 | 11 | (2R,6R)-2-amino-6,7-bis(PamO)-4-THT-Glu-Gly—Glu—Gly-D-Glu—OH |
| 7 | 12 | (2R,6R)-2-amino-6,7-bis(PamO)-4-THT-Gly-Gly—Gly—Glu—OH |
| 8 | 13 | (2R,6R)-2-amino-6,7-bis(PamO)-4-THT-Gly-Gly-D-Glu—OH |
| 9 | 14 | (2R,6S)-2-amino-6,7-bis(PamO)-4-THT-Gly-Gly—Gly—Glu—OH |
| 10 | 15 | (2R,6S)-2-amino-6,7-bis(PamO)-4-THT-Gly—Gly—Gly-D-Glu—OH |
| 11 | 16 | (2R,6R)-2-amino-6,7-bis(PamO)-4-THT-Glu-Gly-D-Glu—OH |
| 12 | 17 | (2R,6R)-2-amino-6,7-bis(PamO)-4-THT-Gly—Glu—OH |
| 13 | 18 | (2R,6R)-2-amino-6,7-bis(PamO)-4-THT-Gly—Gly—OH |
| 14 | 19 | (2R,6R)-2-amino-6,7-bis(PamO)-4-THT-Gly—Glu—OH |
| 15 | 20 | (2R,6R)-2-amino-6,7-bis(PamO)-4-THT-Glu—OH |
| 16 | 21 | (2R,6R)-2-amino-6,7-bis(PamO)-4-THT-Gly—Gly—Gly—Asp—OH |
| 17 | 22 | (2R,6R)-2-amino-6,7-bis(PamO)-4-THT-Gly—Gly-D-Glu—OH |
| 18 | 23 | (2R,6R)-2-amino-6,7-bis(PamO)-4-THT-Gly—Gly—OH |
| 19 | 24 | (2R,6R)-2-amino-6,7-bis(PamO)-4-THT-Gly—D-Glu—OH |
| 20 | 25 | (2R,6R)-2-amino-6,7-bis(PamO)-4-THT-D-Glu—OH |
| 21 | 26 | (2R,6R)-2-amino-6,7-bis(PamO)-4-THT-Asp—OH |
| 22 | 27 | (2R,6R)-2-amino-6,7-bis(PamO)-4-THT-D-Asp—OH |
| 23 | 28 | (2R,6R)-2-amino-6,7-bis(PamO)-4-THT-Gly—Glu—Glu—OH |
| 24 | 29 | (2R,6R)-2-amino-6,7-bis(PamO)-4-THT-Gly—Glu-D-Glu—OH |
| 25 | 30 | (2R,6R)-2-amino-6,7-bis(PamO)-4-THT-Glu—Gly—Glu—OH |
| 26 | 31 | (2R,6R)-2-amino-6,7-bis(PamO)-4-THT-Glu—Glu—OH |
| 27 | 32 | (2R,6R)-2-amino-6,7-bis(PamO)-4-THT-Glu—D-Glu—OH |
| 28 | 33 | (2R,6R)-2-amino-6,7-bis(PamO)-4-THT-Glu—Glu—Glu—OH |
| 29 | 34 | (2R,6R)-2-amino-6,7-bis(PamO)-4-THT-Glu—Glu-D-Glu—OH |
| 30 | 36 | (2R,6R)-2-amino-6-hexanoyloxy-7-PamO-4-THT-Gly—Gly—Gly—Glu—OH |
| 31 | 37 | (2R,6R)-2-Fmoc-amino-6,7-bis(PamO)-4-THT-Glu—Gly-D-Glu—OH |
| 32 | 38 | (2R,6R)-2-acetylamino-6,7-bis(PamO)-4-THT-Glu—Gly-D-Glu—OH |
| 33 | 39 | (2R,6R)-2-hexanoylamino-6-hexanoyloxy-7-PamO-4-THT-Gly—Gly—Gly—Glu—OH |
| 34 | 42 | (2R,6R)-2-amino-6,7-bis(SteO)-4-THT-Gly—Glu—Glu—OH |
| 35 | 43 | (2R,6R)-2-amino-6,7-bis(MyrO)-4-THT-Gly—Glu—Glu—OH |
| 36 | 44 | (2R,6R)-2-amino-6,7-bis(PamO)-4-THT-NH(CH$_2$)$_2$CO—Glu—OH hydrochloride |
| 37 | 45 | (2R,6R)-2-amino-6,7-bis(PamO)-4-THT-NH(CH$_2$)$_{11}$CO—Glu—OH hydrochloride |
| 38 | 46 | (2R,6R)-4-(2-amino-6,7-bis(PamO)-4-THT-amino)benzoyl-Glu—OH hydrochloride |
| 39 | 47 | (2R,6R)-4-(2-amino-6,7-bis(PamO)-4-THT-Gly-amino)benzoyl-Glu—OH hydrochloride |
| 40 | 48 | (2R,6R)-2-amino-6,7-bis(PamO)-4-THT-NH(CH$_2$)$_5$CO—Glu—OH TFA salt |
| 41 | 49 | (2R,6R)-2-amino-6,7-bis(PamO)-4-THT-NH(CH$_2$)$_6$NHCO—Glu—OH TFA salt |
| 42 | 50 | (2R,6R)-4-(2-amino-6,7-bis(PamO)-4-THT-aminomethyl)benzoyl-Glu—OH hydrochloride |
| 43 | 51 | (2R,6R)-4-(N-(2-Fmoc-amino-6,7-bis(PamO)-4-THT)-N-(carboxymethyl)aminomethyl)benzoyl-Glu—OH |
| 44 | 52 | (2R,6R)-2-amino-6,7-bis(PamO)-4-THT-Gly—Lys—Gly—OH 2TFA salt |

Retention time of Compounds 1 to 15 in high performance liquid chromatography is shown as follows:

Column: YMC-Pack A-602 $NH_2$ (Yamamura Chemical Laboratories, Japan)

Mobile phase: 85% methanol/0.02M phosphate buffer (pH 4.8)

Flow rate: 1.0 ml/min.

Detecting method: UV, 214 nm

Retention time (minute): Compound 1, 17.3; Compound 2, 17.1; Compound 3, 15.9; Compound 4, 15.8; Compound 5, 1.85; Compound 7, 20.7; Compound 8, 19.7; Compound 9, 20.7; Compound 10, 19.8; Compound 12, 19.4; Compound 14, 9.4; Compound 15, 18.4

Biological activities of the compound (I) are describes as follows.

Experimental Example 1

Actions of compound (I) produced in the foregoing Examples on enhancing proliferation of bone marrow cells of mice are shown in Table 2.

TABLE 2

Actions on enhancing proliferation of bone marrow cells of mice

| Compound No. | Minimal Effective Concentration (MEC, ng/ml)*[1] |
| --- | --- |
| 1 | 0.625 |
| 2 | <0.156 |
| 8 | <0.156 |
| 12 | <0.156 |
| 14 | 0.156 |
| 36 | <0.156 |
| 44 | <0.156 |

*[1]Assuming that proliferation in the group, to which no test compound was added, was 1, concentrations at which 1.3 or more times as much proliferation was observed were taken.

Method of determination:

To an RPMI 1640 culture medium [Bio-Wittaker Inc. (hereinafter abbreviated as BW), USA] containing $2 \times 10^6$/ml of bone marrow cells of BALB/c mice, 2 mM of L-glutamine, 20 ug/ml of gentamicin (Flow Laboratories, Inc., Scotland), 10% fetal calf serum (BW, USA) was added a test compound in an adequate concentration, which was incubated at 37° C. for 3 days in 5% carbon dioxide in air followed by determination of proliferation of the bone marrow cells by the MTT reduction method [Tada et al., Journal of Immunological Methods, Vol. 93, p.157, 1986].

Experimental Example 2

Actions of compound (I) on enhancing the number of spleen cells of mice are shown in Table 3.

TABLE 3

Actions on enhancing the number of spleen cells

| Drug | Dosage (mg/kg/day) | Number of spleen cells (%)*[1] |
| --- | --- | --- |
| Cyclophosphamide singly | | 33.4 |
| Cyclophosphamide + compound 8 | 0.1 | 78.6 |

*[1]Number of cells in the mouse administered intraperitoneally with physiological saline solution containing 2% gum arabic is assumed as 100%.

Method of Determination:

A BALB/c mouse was injected intraperitoneally with cyclophosphamide dissolved in physiological saline solution at a dose of 200 mg/kg. From the day after next, the animal was administered intraperitoneally for 4 consecutive days with the test compound suspended in physiological saline solution containing 2% gun arabic. On the day following completion of the administration, number of trypan blue chromophobic cells of spleen was counted.

Experimental Example 3

Actions of compound (I) on enhancing the number of leukocytes in mice are shown in Table 4.

TABLE 4

Actions on enhancing the number of leukocytes

| Compound No. | Dosage (mg/kg/day) | Number of leukocytes*[1] |
| --- | --- | --- |
| 2 | 0.063 | 102 |
| 7 | 0.031 | 129 |
| 14 | 0.13 | 118 |

*[1]The value is shown by percentage relative to the number of leukocytes (assumed as 100%) of the mouse orally administered with physiological saline solution, in place of cyclophosphamide, at a dose of 0.2 ml relative to 20 g of body weight, then subcutaneously administered, from the next day of the oral administration, with 5% glucose once a day for 5 days. Incidentally, the average value and standard deviation of leukocyte numbers of mice orally administered with cyclophospha mide at a dose of 150 mg/kg, then from the next day, subcutaneously administered with 0.2 ml of 5% glucose relative to 20 g of body weight once a day for 5 days were 41 ± 11% throughout the experiment.

Method of Determination:

Six week old female CDF1/Crj mice (5 animals/group) were subjected to the experiment. Each animal was orally administered with cyclophosphamide dissolved in physiological saline solution at a dose of 150 mg/kg. From the next day, each animal was administered subcutaneously with the compound suspended in 5% glucose at the following dosages for five days once a day. On the next day after completion of the administration, about 100 µl of peripheral blood was collected from orbital vein using an EDTA-treated glass capillary. Then, the number of lekocytes was counted using a automatic cell analyzer (Sysmex K-2000, Toa Medical Electronics, Japan)

Experimental Example 4

Actions of compound (I) produced in the foregoing Examples on enhancing development of megakaryocyte colonies are shown in Table 5.

TABLE 5

| Test Compound No. | Concentration (ng/ml) | Degree of megakaryocyte colony formation *[1] |
| --- | --- | --- |
| 12 | 0.4 | 1.82 |
| | 4 | 2.01 |

*[1]Number of megakaryocyte colonies in the group to which compound (I) is not added is shown as 1.

Method of determination:

The production of megakaryocyte colonies was studied according to a plasma clot method [Mizoguti et al., Experimental Hematology, Vol. 7, pp.345 to 351, 1979].

To a NCTC-109 culture medium (Gibco BRL Inc, USA) containing $5 \times 10^6$/ml of bone marrow cells of BALB/c mice, 20% fetal calf serum (BW, USA), 1% serum albumin, 0.026 mg/ml $CaCl_2$, 0.02 mg/ml L-asparagine, 10% bovine sodium citrated plasma was added a test compound in an adequate concentration and then thoroughly mixed. A 0.4 ml aliquot thereof was placed in the center of plastic dish 35×10 mm (A/S Nunc, Denmark) and allowed to clot. To the culture dish was added 0.6 ml of α-MEM culture medium (BW, USA) containing 10% fetal calf serum and then the culture was incubated at 37° C. in 5% $CO_2$ in air during 7 days. After incubation, culture medium surrounding the plasma clot was removed and the plasma clot was dehydrated by placing a piece of filter paper on its surface. Then 1 to 2 drops of 5% glutaraldehyde were dropped on the remaining filter paper over the clot. After ten minutes, the piece of filter paper was removed and then the clot was washed with 0.1M phosphate buffer (pH 6.0). The clot was subjected to acetylcholinesterase (hereinafter abbreviated as AchE) dyeing. To 0.1M phosphate buffers (45 ml) containing acetylthio choline iodide (30 mg) was added 30 mM copper sulfate aqueous solution (6 ml) and 0.1M sodium citrate aqueous solution (3 ml) and 5 mM potassium ferricyanide aqueous solution (6 ml) in order. Two ml of each of the resulting solution was added to the plate. After standing at 33° C. for 4 to 6 hours, counted the number of the megakaryocte colonies.

Experimental Example 5

Actions of compound (I) produced in the foregoing Examples on enhancing development of AchE positive cells are shown in Table 6.

TABLE 6

| Test Compound No. | Concentration (ng/ml) | Degree of AchE positive cell *1 |
| --- | --- | --- |
| 7 | 0.1 | 1.51 |
| 12 | 0.1 | 1.43 |
| 23 | 0.1 | 1.67 |

*1 AchE activity in the group to which compound (I) is not added is shown as 1.

Method of determination:

The AchE activity was studied according to a fluorescence method (Ishibashi et al., Proceedings of the National Academy of Science USA, Vol. 86, pp. 5953 to 5957, 1989).

Nonadherent bone marrow cells of BALB/c mice ($1 \times 10^6$ cells/ml) were suspended in Iscove's modification of Dulbecco's medium (Gibco BRL Inc, USA) containing 1% Neutridoma-SP (Boheringer Mannhaim, Germany). Twenty-five µl of a test compound solution in an adequate concentration was inoculated in a 96-well plate. To each of this solution in the well was added 100 µl of the nonadherent bone marrow cells suspension. After incubation at 37° C. for 5 days, 25 µl of 6% glutalaldehyde aqueous solution was added to the well. After standing at 4° C. for 30 minutes the mixture was centrifuged (850×g) at 5° C. and the supernatant was removed. After washing the deposit in the well with 100 µl of phosphate buffered saline, to the deposit was added 100 µl of buffer (pH 7.5) containing 0.2% polyoxyethylene-10-octylphenyl etherd (POPE), 1 mM ethylenediaminetetraacetate (EDTA), 0.12M sodium chloride and 50 mM N-2-hydroxyethylpiperadine-N'-2-ethansulfonic acid (HEPES). To this was added 10 µl of acetylthiocholine iodide aqueous solution (concentration: 1.6 mg/ml). After incubation at 33° C. for 3 hours 10 µl of the resulting solution was separated. To this was added 10 µl of 0.4 mM 7-diethylamino-3-(4'-maleimidylphenyl)-4-methylcoumrin aqueous solution and 100 µl of buffer (pH 5.0) containing 0.2% POPE, 1 mM EDTA and 50 mM sodium acetate and fluorescence emission was determined on a fluorometer (excitation wave length: 365 nm, fluorescence wave length: 450 nm).

Experimental Example 6

Toxicity test

No mouse administered intraperitoneally with Compound 3 at a dose of 100 mg/kg was found dead.

Experimental Example 7

Toxicity test

No mouse administered subcutaneously with disodium salt of Compound 7 at a dose of 100 mg/kg was found dead.

Compound (I) or a salt thereof is low in toxicity and can be used safely.

As is clear from the foregoing experimental Examples, Compound (I) or a salt thereof has an activity of remarkably improving hematopoietic disorder, which can be utilized as a therapeutic or prophylactic agent of leukocytopenia caused by radiotherapy or chemotherapy of cancers in mammals (e.g. dog, cat, cow, horse, monkey, man, etc.), as an hematopoietic-stimulating agent in the case of bone marrow transplantation, as an immunological enhancing agent having an action of increasing leukocytes, and, further as a therapeutic agent of thrombocytopenia.

Formulation Example 1

The compound 2 (4 g) obtained in Example 8 and mannitol (50 g) were dissolved in sterilized distilled water (1 liter) containing polyethylene glycol 400 (30% w/w). The solution was subjected to filtration under sterilization, and 1 ml each of which was then distributed in one ampoule to prepare intravenous injection containing 4 mg of the compound 2 per ampoule.

Formulation Example 2

The trisodium salt of compound 23 (40 mg) obtained in Example 53 and mannitol (50 g) were dissolved in sterilized distilled water (1 liter) containing polyethylene glycol 400 (30% w/w). The solution was subjected to filtration under sterilization, and 1 ml each of which was then distributed in one ampoule to prepare intravenous injection containing 40 µg of the trisodium salt of compound 23 per ampoule.

What is claimed is:

1. A compound having the formula:

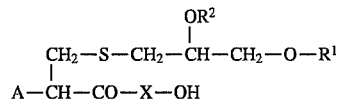

wherein each of $R^1$ and $R^2$ is hydrogen or aliphatic acyl, A is amino which may be protected by a protective group selected from the group consisting of formyl, $C_{6-14}$ arylcarbonyl, substituted oxycarbonyl, $C_{7-19}$ aralkyl-carbonyl, trityl and phthaloyl, X is an amino acid sequence consisting of 1 to 10 amino acid residues which contain at least one acidic amino acid residue, or a salt thereof.

2. The compound according to claim 1, wherein X is an amino acid sequence consisting of 1 to 6 amino acid residues.

3. The compound according to claim 1, wherein A is amino which may be substituted with substituted oxycarbonyl selected from the group consisting of $C_{1-6}$ alkyloxycarbonyl, $C_{6-14}$ aryloxycarbonyl, 9-fluorenylmethyloxycarbonyl, $C_{7-19}$ aralkyloxy-carbonyl and adamantyloxy-carbonyl.

4. The compound according to claim 1, wherein the aliphatic acyl is $C_{2-30}$ aliphatic acyl.

5. The compound according to claim 1, wherein at least one of $R^1$ and $R^2$ is aliphatic acyl.

6. The compound according to claim 1, wherein $R^1$ is aliphatic acyl.

7. The compound according to claim 1, wherein $R^2$ is aliphatic acyl.

8. (2R,6R)-2-amino-6,7-bis(hexadecanoyloxy)-4-thiaheptanoyl-glycyl-glutamyl-glutamic acid or a salt thereof.

9. (2R,6R)-2-amino-6,7-bis(hexadecanoyloxy)- 4-thiaheptanoyl-glycyl-glutamic acid or a salt thereof.

10. (2R,6R)-2-amino-6,7-bis(hexadecanoyloxy)- 4-thiaheptanoyl-glutamyl-glycyl-glutamic acid or a salt thereof.

11. (2R,6R)-2-amino-6,7-bis(hexadecanoyloxy)- 4-thiaheptanoyl-glycyl-D-glutamic acid or a salt thereof.

12. An immuno-stimulating composition having a leukocyte-increasing action, which comprises a compound or a salt thereof as claimed in claim 1 and a pharmaceutically acceptable carrier, excipient or diluent.

13. The immuno-stimulating composition according to claim 14, wherein at least one of $R^1$ and $R^2$ is aliphatic acyl.

14. A composition for treating thrombocytopenia, which comprises a compound or a salt thereof as claimed in claim 1 and a pharmaceutically acceptable carrier, excipient or diluent.

15. A method of producing the compound or a salt thereof as claimed in claim 1, which comprises subjecting a compound of the formula:

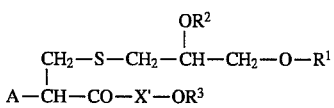

wherein each of $R^1$ and $R^2$ is hydrogen or aliphatic acyl, $R^3$ is a protecting group, A is amino which may be protected by a protective group selected from the group consisting of formyl $C_{7-10}$ aryl carbonyl, substituted oxycarbonyl, $C_{7-10}$ aralkylcarbonyl and phthaloyl, X' is an amino acid sequence consisting of 1 to 10 optionally protected amino acid residues which contain at least one optionally protected acidic amino acid residue, or its salt, to a deprotection reaction.

16. The compound according to claim 1, wherein X is an amino acid sequence consisting of 1 to 6 amino acid residues which contain one to three glutamyl amino acid residues.

17. (2R,6S)-2-amino- 6,7-bis(hexadecanoyloxy)-4-thiaheptanoyl-glycyl-glycyl-glycyl-glutamyl-threonyl-threonine or a salt thereof.

18. (2R,6R)-2-amino- 6,7-bis(hexadecanoyloxy)-4-thiaheptanoyl-glycyl-glycyl-glycyl-glutamyl-threonyl-threonine or a salt thereof.

19. (2R,6R)-2-amino- 6,7-bis(hexadecanoyloxy)-4-thiaheptanoyl-glycyl-glycyl-glycyl-glutamyl-threonine or a salt thereof.

20. (2R,6R)-2-amino- 6,7-bis(hexadecanoyloxy)-4-thiaheptanoyl-glycyl-glycyl-glycyl-glutamic acid or a salt thereof.

21. (2R,6R)-2-amino- 6,7-bis(hexadecanoyloxy)-4-thiaheptanoyl-glycyl-glycyl-glycyl-D-glutamic acid or a salt thereof.

22. (2R,6S)-2-amino- 6,7-bis(hexadecanoyloxy)-4-thiaheptanoyl-glycyl-glycyl-glycyl-glutamic acid or a salt thereof.

23. (2R,6S)-2-amino- 6,7-bis(hexadecanoyloxy)-4-thiaheptanoyl-glycyl-glycyl-glycyl-D-glutamic acid or a salt thereof.

24. (2R,6R)-2-amino- 6,7-bis(hexadecanoyloxy)-4-thiaheptanoyl-glutamic acid or a salt thereof.

25. (2R,6R)-2-amino- 6,7-bis(hexadecanoyloxy)-4-thiaheptanoyl-glutamyl-glycyl-D-glutamic acid or a salt thereof.

26. (2R,6R)-2-amino- 6,7-bis(hexadecanoyloxy)-4-thiaheptanoyl-glutamyl-glycyl-glutamyl-glycyl-D-glutamic acid or a salt thereof.

27. (2R,6R)-2-amino- 6,7-bis(hexadecanoyloxy)-4-thiaheptanoyl-glycyl-glycyl-D-glutamic acid or a salt thereof.

28. (2R,6R)-2-amino- 6,7-bis(hexadecanoyloxy)- 4-thiaheptanoyl-glutamyl-D-glutamic acid or a salt thereof.

29. (2R,6R)-2-amino- 6,7-bis(hexadecanoyloxy)-4-thiaheptanoyl-glutamyl-glutamyl-D-glutamic acid or a salt thereof.

30. (2R,6R)-2-amino- 6,7-bis(hexadecanoyloxy)-4-thiaheptanoyl-glycyl-glutamyl-D-glutamic acid or a salt thereof.

31. (2R,6R)-2-amino- 6,7-bis(hexadecanoyloxy)-4-thiaheptanoyl-glutamyl-glutamic acid or a salt thereof.

32. (2R,6R)-2-amino- 6,7-bis(hexadecanoyloxy)-4-thiaheptanoyl-glutamyl-glutamyl-glutamic acid or a salt thereof.

33. (2R,6R)-2-amino- 6,7-bis(hexadecanoyloxy)-4-thiaheptanoyl-glycyl-glycyl-glutamic acid or a salt thereof.

34. (2R,6R)-2-amino- 6,7-bis(hexadecanoyloxy)-4-thiaheptanoyl-glycyl-D-glutamic acid or a salt thereof.

35. (2R,6R)-2-amino- 6,7-bis(hexadecanoyloxy)-4-thiaheptanoyl-glycyl-glycyl-glycyl-aspartic acid or a salt thereof.

36. (2R,6R)-2-( 9-fluorenylmethyloxycarbonylamino)-6,7-bis(hexadecanoyloxy)-4-thiaheptanoyl-glutamyl-glycyl-D-glutamic acid or a salt thereof.

37. (2R,6R)-2-amino- 6,7-bis(hexadecanoyloxy)-4-thiaheptanoyl-glutamyl-glycyl-glutamic acid or a salt thereof.

38. (2R,6R)-2-amino- 6,7-bis(octadecanoyloxy)-4-thiaheptanoyl-glutamyl-glutamyl-glutamic acid or a salt thereof.

39. (2R,6R)-2-amino- 6,7-bis(tetradecanoyloxy)-4-thiaheptanoyl-glycyl-glutamyl-glutamic acid or a salt thereof.

* * * * *